US008686008B2

(12) United States Patent
McCurdy et al.

(10) Patent No.: US 8,686,008 B2
(45) Date of Patent: Apr. 1, 2014

(54) HIGHLY SELECTIVE SIGMA RECEPTOR LIGANDS

(75) Inventors: Christopher R. McCurdy, Oxford, MS (US); Christophe Mesangeau, Oxford, MS (US); Rae Reiko Matsumoto, Morgantown, WV (US); Jacques Henri Poupaert, Brussels (BE); Bonnie Ann Avery, Oxford, MS (US); Ahmed Hassan Amin Abdelazeem, Oxford, MS (US)

(73) Assignees: The University of Mississippi, University, MI (US); L'Universite Catholique de Louvain, Louvain-la-Neuve (BE)

( * ) Notice: Subject to any disclaimer, the term of this patent is extended or adjusted under 35 U.S.C. 154(b) by 540 days.

(21) Appl. No.: 12/785,217

(22) Filed: May 21, 2010

(65) Prior Publication Data
US 2010/0329978 A1  Dec. 30, 2010

Related U.S. Application Data

(63) Continuation-in-part of application No. 12/673,486, filed as application No. PCT/US2008/073478 on Aug. 18, 2008.

(60) Provisional application No. 60/956,249, filed on Aug. 16, 2007.

(51) Int. Cl.
*A01N 43/78* (2006.01)
*A61K 31/425* (2006.01)
*A61K 31/497* (2006.01)
*C07D 417/00* (2006.01)
*C07D 241/04* (2006.01)
*C07D 295/00* (2006.01)
*C07D 413/00* (2006.01)

(52) U.S. Cl.
USPC ............... 514/367; 514/252.12; 546/270.1; 544/358; 544/369

(58) Field of Classification Search
USPC ........... 514/367, 252.12; 546/240.1; 544/358, 544/369
See application file for complete search history.

(56) References Cited

U.S. PATENT DOCUMENTS 4,215,119 A    7/1980   Mentrup et al.
4,791,104 A   12/1988   Picciola et al.
(Continued)

FOREIGN PATENT DOCUMENTS

EP       1043319 A1     10/2000
WO    WO 87-02359 A1    4/1987
WO    WO 9743282 A2 *  11/1997

OTHER PUBLICATIONS

Sheridan, R.P. "The Most Common Chemical Replacements in Drug-Like Compounds" J. Chem. Inf. Comput. Sci., 2002, vol. 42, pp. 103-108.*

(Continued)

*Primary Examiner* — Kendra D Carter
(74) *Attorney, Agent, or Firm* — Hershkovitz & Associates, PLLC; Abraham Hershkovitz; Eugene Rzucidlo

(57) ABSTRACT

Compounds having the general formula II, III, or IV

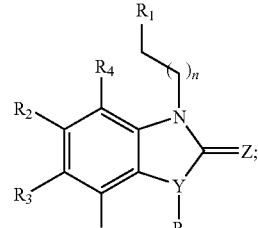

II

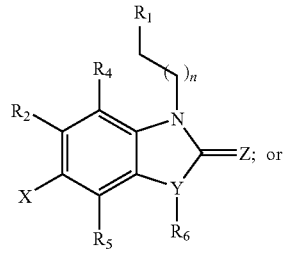

III

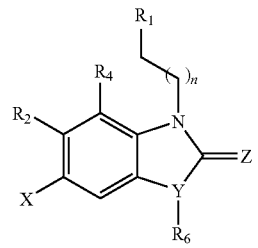

IV wherein $R_1$ can be a radical of an optionally substituted C-4 to C-7 N-containing heterocycle or a radical of an optionally substituted cyclic or acyclic tertiary amine or isoindoline-1, 3-dione: $R_{2,3,4,5,6}$ can each independently be any one or combinations of the following moieties, cyano, nitro, acyl, alkyl, amido, azido, isothiocyanate, isocyanate, optionally substituted anilino, halogens, ethers, sulfonamides, thioacyl, nitro, aromatic, heterocyclic, olefinic, acetylene, deuterium, or tritium; Y can be either CH, $CH_2$, O, S, $OCH_2$, N—R, N—Ar, C—R, C—Ar; Z can be either H, O, S, S—R or NR. R groups can be either H, aryls, alkyls, or cycloalkyls; "n" can be 1 to 5 carbons in length and stereoisomers, functional analogs, and pharmaceutically acceptable salts thereof and wherein the moiety bridging $R_1$ and N can be a substituted alkylene, optionally substituted alkenylene or optionally substituted alkynylene and where the alkylene group can include an inserted $C_3$-$C_5$ cycloalkyl group, aromatic, and hetercocyclic group; wherein X' is halogen, or $C_1$-$C_4$ haloalyl; wherein the $R_x$ is a $C_1$-$C_5$ straight chain or branched chain alkyl or a $C_1$-$C_4$ straight chain or branched chain haloalkyl.

2 Claims, 6 Drawing Sheets

(56) References Cited

U.S. PATENT DOCUMENTS 4,797,399 A * 1/1989 Ueda et al. ............ 514/253.04
5,473,066 A * 12/1995 Yamamori et al. ............ 540/491

OTHER PUBLICATIONS

Baillie, T.A. "The Use of Stable Isotopes in Pharmacological Research" Pharmacological Reviews, 1981, vol. 33, No. 2, pp. 81-132.*

Tonn et al. "Simulataneous Analysis of Diphenhydramine and a Stable Isotope Analog (2H10)Diphenhydramine Using Capillary Gass Chromatography with Mass Selective Detection in Biological Fluids from Chronically Instrumented Pregnant Ewes" Biological Mass Spectrometry, 1993, vol. 22, pp. 633-642.*

Wolen, R.L. "The Application of Stable Isotopes to Studies of Drug Bioavailability and Bioequivalence", J Clin Pharmacol, 1986, vol. 26, pp. 419-424.*

Haskins, N.J. "The Application of Stable Isotopes in Biomedical Research" biomedical mass Spectrometry, 1982, vol. 9, No. 7, pp. 269-277.*

Gouyette, A. "Synethesis of Deuterium-labelled Elliptinium and its Use in Metabolic Studies" biomedical and Environmental Mass Spectrometry, 1988, vol. 15, pp. 243-247.*

Browne, T.R. "Stable Isotope Techniques in Early Drug Development: An Economic Evaluation" J Clin Pharmacol, 1998, vol. 38, pp. 213-220.*

Yous, Said et al,, "Novel 2(3H)-benzothiazolones as highly potent and selective sigma-1 receptor ligands" Medicinal Chemistry Research, 2005, vol. 14, No. 3, pp. 158-1683.

Ucar, Huseyin et al., "Synthesis and Anticonvulsant Activity of 2(3H)-benzoxazolone and 2(3H)-benzothiazolone derivatives" Journal of Medicinal Chemistry, 1998, vol. 41, No. 7, pp. 1138-1145.

Ucar, Huseyin et al., "2(3H)-benzoxazolone and 2(3H)-benzothiazolone derivatives: Novel, potent and selective sigma 1 receptor ligands" European journal of Pharmacology, 1997, vol. 335, No. 2/3, pp. 267-273.

International Search Report issued Feb. 9, 2009 corresponding to PCT/US2008/073478.

Matsumoto, R.R. et. al. Eur. J. Pharmacol. 2001, 411, 261-273.

Maurice, T. et. al. Prog. Neuropsychopharmacol. Biol. Psychiatry 1997, 21, 69-102.

Sigma receptors: chemistry, cell biology and clinical implications. Edited by Rae R. Matsumoto, Wayne D. Bowen and Tsung Ping Su. New York, Springer 2007.

Hanner, M. et. al. Proc. Natl. Acad. Sci. USA. 1996, 93, 8072-8077.

Kekuda, R. Y., et. al. Biochem. Biophys. Res. Commun. 1996, 229, 553-558.

Seth, P. et. al. Biochem. Biophys. Res. Commun. 1997, 41, 535-540.

Seth, P. et. al. J. Neurochem. 1998, 70, 922-931.

Mei, J and Pasternak GW. Biochem Pharmacol. 2001, 62, 349-355.

Perrine, DM (1996) The Chemistry of Mind-Altering Drugs. American Chemical Society. Washington, DC.

National Survey on Drug Use and Health—http://www.samhsa.gov, Jun. 8, 2011.

Carroll FI., Howell LL, Kuhar MJ (1999) Pharmacotherapies for treatment of cocaine abuse: preclinical aspects. J. Med. Chem. 42: 2721-2736.

Sharkey J,Glen KA, Wolfe S, Kuhar MJ. Cocaine binding at sigma receptors. Eur.J.Pharmacol. 1988, 149:171-174.

Mittleman R, Wetli CV. Death caused by recreational cocaine use: an update. J. Am. Med. Assoc. 1984, 252:1889-1893.

* cited by examiner

Metabolic stability of AZ_66 by Rat liver microsomes (1mg/ml)

| Time(min) | Percent Remaining | Percent Loss |
|---|---|---|
| 0 | 100 | 0 |
| 5 | 95.51694 | 4.48306 |
| 15 | 88.64231 | 11.35845 |
| 30 | 82.70131 | 17.29879 |
| 60 | 75.09347 | 24.3653 |

In vitro Half-life and Intrinsic clearance

| k(min$^{-1}$) | t$_{1/2}$(min) | CLint(ml/min/mg) | CLint (whole liver) (L/min) |
|---|---|---|---|
| 0.006 | 115.56±15 | 0.006 | 0.002434 |

Incubation of CM_156 (10µM) with rat liver microsomes (1mg/ml)

| Time (min) | Percent Remaining |
|---|---|
| 0 | 100 |
| 15 | 16.4605 |
| 30 | 9.2356 |

HIGHLY SELECTIVE SIGMA RECEPTOR LIGANDS

CROSS-REFERENCE TO RELATED APPLICATIONS

This is a Continuation-in-part application of U.S. application Ser. No. 12/673,486, filed on Feb. 12, 2010, entitled "HIGHLY SELECTIVE SIGMA RECEPTOR LIGANDS", which claims priority of PCT/US08/73478 filed Aug. 18, 2008 which claims priority to U.S. Provisional Applciation No. 60/956,249 filed Aug. 16, 2007, the disclosure of all of which is expressly incorporated by reference herein in its entirety.

The subject invention ws made with government support under a research project supported by the United States Government in NIDA Grant Numbers DA023205, DA011979, DA013978 and NCRR P20 RR021929 and the government has certain rights in this invention.

FIELD OF INVENTION

The present invention relates to the field of compounds which are sigma receptor ligands and methods of use thereof as sigma receptor ligands.

BACKGROUND OF THE INVENTION

Sigma receptors (a) have received much attention from the drug discovery field due to their possible involvement in schizophrenia, regulation of motor behavior, convulsions, anxiety, and the psychostimulant effects of drugs of abuse including cocaine, methamphetamine and 3,4-methylenedioxymethamphetamine (MDMA).[1,2] In addition to a host of neurological and psychiatric areas of interest, sigma receptors are promising drug development targets for, oncological, immunological, cardiovascular, opthalmological, developmental, gastrointestinal and metabolic disorders as well as those affecting the endocrine system. They are structurally unique proteins that are distinct from classical G protein-coupled receptors, ionotropic receptors, or receptor tyrosine kinases. With two subtypes currently known, they modulate cell survival and excitability, and subserve many critical functions in the body. Endogenous ligands for these receptors are unknown, though current clues point to neurosteroids.[3]

The two subtypes, σ-1 and σ-2, were delineated by studies examining their respective molecular weights, distribution in tissue and drug selectivity profiles. The 223 amino acid σ-1 protein with two transmembrane spanning regions has been purified and cloned from several animal species including mouse, rat, guinea pig, and human.[4-8] To date, the σ-1 receptor is well studied and known because of the receptor sequence information and availability of selective σ-1 ligands. But, the protein corresponding to σ-2 sites has not yet been cloned. Also, σ-2 receptor-selective ligands are less common, with tritiated DTG (1,3-di(2-tolyl)guanidine) being accepted as a radioligand in the presence of (+)-pentazocine (to block binding to σ-1 sites). Due to the lack of availability of detailed protein structural information and truly selective σ-2 ligands, the pharmacological characterization of the σ-2 subtype has been very limited. There is clearly a need for a selective σ-2 ligand which can not only act as a probe to explore unknown biochemical mechanisms, but also be used as a radioligand in σ-2 receptor binding assays.

The abuse of drugs is a serious social, economic and health problem worldwide. Some of the opiates, cocaine, amphetamines and phencyclidine (PCP) are the drugs of abuse with significant affinities for a receptors. Current treatments for drugs of abuse are limited and there is a need to develop novel and effective agents to combat this problem.

Cocaine use and abuse has been reported as early as the late 1500s.[9] The historical use has been associated with the chewing of leaves from the Erythroxylon coca bush, from which cocaine was isolated in 1860,[10] to eliminate fatigue in workers. Indeed, cocaine is a powerful and addictive psychostimulant. Cocaine abuse is widespread and is responsible for more serious intoxications and deaths than any other illicit drug. However, the invigorating effects of cocaine have caused it to become a major recreational drug of abuse throughout the world with an estimated 13 million people using the drug. In 2004, 34.2 million Americans aged 12 and over reported lifetime use of cocaine with approximately 5.6 million reporting annual use and an estimated 2 million reporting current use of the drug. In 2004 alone, there were an estimated 1 million new users of cocaine amounting to ~2,700 per day. Despite a decline between 2002 and 2003 which is thought to potentially be due to increases in usage of other stimulants such as methamphetamine, data from the National Survey on Drug Use and Health showed near a 70% increase in the number of people receiving treatment for cocaine addiction from 276,000 in 2003 to 466,000 in 2004.[11]

Currently, there are no approved medications to treat cocaine abuse or addiction. An effective strategy used to develop an anti-cocaine agent was the development of antagonists that compete with cocaine for its target proteins. For years, treatment approaches have targeted the dopaminergic system which is known to be involved in the actions and rewards of cocaine use. Many compounds were generated and tested that targeted the dopamine transporter which was identified as a primary site of action of cocaine. These compounds were met with very limited success as many of them just substituted for cocaine.[12] After many years of investigation at the dopamine transporter as well as the dopamine receptors, researchers have been challenged to envision novel mechanisms that may afford new therapeutic interventions for cocaine addiction.

Although many other mechanisms are under investigation, the a receptor system has been demonstrated and validated as a legitimate target for the attenuation of cocaine effects. The ability of cocaine to bind to the sigma receptors was discovered and first documented in 1988.[13] It was reported that cocaine had micromolar affinity to the sigma receptor, and this interaction corresponded to micromolar levels that were achievable by cocaine in the body.[14] Additional studies have indicated that reducing brain sigma receptor levels with anti-sense oligonucleotides attenuates the convulsive and locomotor stimulant actions of cocaine. Synthetic small molecule antagonists for sigma receptors have also been shown to mitigate the actions of cocaine in animal models. From prior work, the role of the σ-1 subtype has been clearly linked to the actions of cocaine. However, the role of the σ-2 receptor has been suggested, but is less clear due to the lack of truly selective ligands for this subtype.

BRIEF DESCRIPTION OF THE INVENTION

The present invention relates to compounds useful as sigma receptors of the following formula I:

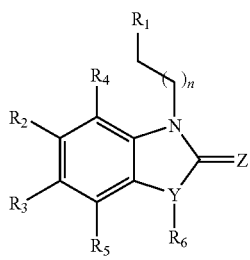

Wherein $R_1$ can be an optionally substituted nitrogen-containing heterocycle radical such as, for example, radicals of optionally substituted piperidines, optionally substituted piperazines, optionally substituted tetrahydropyridines, optionally substituted azepanes, tertiary amines (cyclic or acyclic), isoindoline-1,3-dione, or optionally substituted tetrahydroisoquinolones (aromatically substituted): $R_{2,3,4,5,6}$ can each independently be any one or combinations of the following moieties, such as, for example, cyano, nitro, acyl, alkyl, amido, azido, isothiocyanate, isocyanate anilino (unsubstituted or substituted), halogens (such as fluorine, chlorine, bromide and iodine), ethers, sulfonamides, thioacyl, nitro, aromatic, heterocyclic, olefinic, acetylenic, deuterium, or tritium; Y can be either CH, $CH_2$, O, S, $OCH_2$, N—R, N—Ar, C—R, C—Ar where Ar is an optionally substituted aryl. Z can be either H, O, S, S—R or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The moiety bridging $R_1$ and N in the formula I can be an optionally substituted $C_1$-$C_6$ alkylene, $C_1$-$C_6$ alkenylene or $C_1$-$C_6$ alkynylene group wherein the alkylene group can have inserted into its chain a $C_3$-$C_5$ cycloalkyl group, aromatic, and heterocyclic group.

The present invention further relates to compounds useful as sigma receptors of the following formula II:

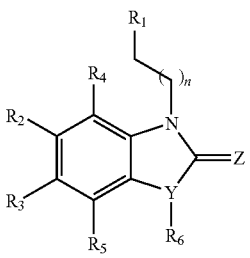

Wherein $R_1$ can be an optionally substituted nitrogen-containing heterocycle radical such as, for example, radicals of optionally substituted piperidines, optionally substituted piperazines, optionally substituted tetrahydropyridines, optionally substituted azepanes, tertiary amines (cyclic or acyclic), isoindoline-1,3-dione, or optionally substituted tetrahydroisoquinolones (aromatically substituted): $R_{2,4,5,6}$ can each independently be any one or combinations of the following moieties, such as, for example, cyano, nitro, acyl, alkyl, amido, azido, isothiocyanate, isocyanate anilino (unsubstituted or substituted), halogens (such as fluorine, chlorine, bromide and iodine), ethers, sulfonamides, thioacyl, nitro, aromatic, heterocyclic, olefinic, acetylenic, deuterium, or tritium; Y can be either CH, $CH_2$, O, S, $OCH_2$, N—R, N—Ar, C—R, C—Ar where Ar is an optionally substituted aryl. Z can be either H, O, S, S—R or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The moiety bridging $R_1$ and N in the formula II can be a substituted $C_1$-$C_6$ alkylene, $C_1$-$C_6$ alkenylene wherein the alkylene group can have inserted into its chain a $C_3$-$C_5$ cycloalkyl group, aromatic, and heterocyclic group.

The present invention relates to still yet further compounds useful as sigma receptors of the following formula III:

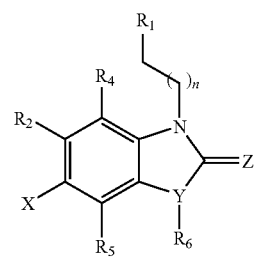

Wherein $R_1$, $R_{2,4,5,6}$ and "n" can be the options provided for formula II, above and wherein $X_1$ is halogen, or $C_1$-$C_4$ haloalyl.

The present invention relates to a still yet further series of compounds useful as sigma receptors of the following formula IV:

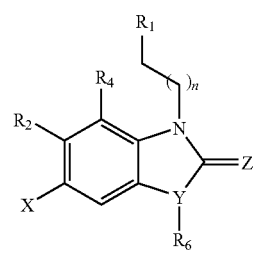

Wherein $R_1$ can be an optionally substituted nitrogen-containing heterocycle radical such as, for example, radicals of optionally substituted piperidines, optionally substituted piperazines, optionally substituted tetrahydropyridines, optionally substituted azepanes, tertiary amines (cyclic or acyclic), isoindoline-1,3-dione, or optionally substituted tetrahydroisoquinolones (aromatically substituted): $R_{2,4,6}$ can each independently be any one or combinations of the following moieties, such as, for example, cyano, nitro, acyl, alkyl, amido, azido, isothiocyanate, isocyanate anilino (unsubstituted or substituted), halogens (such as fluorine, chlorine, bromide and iodine), ethers, sulfonamides, thioacyl, nitro, aromatic, heterocyclic, olefinic, acetylenic, deuterium, or tritium; Y can be either CH, $CH_2$, O, S, $OCH_2$, N—R, N—Ar, C—R, C—Ar where Ar is an optionally substituted aryl. Z can be either H, O, S, S—R or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The moiety bridging R$_1$ and N in the formula IV can be a substituted C$_1$-C$_6$ alkylene having the formula —(CHR$_x$—(CH$_2$)—CH$_2$)— wherein the —CHR$_x$— moiety is attached to R$_1$ and the alkylene group can have inserted into its chain a C$_3$-C$_5$ cycloalkyl group, aromatic, and heterocyclic group and wherein the R$_x$ is a C$_1$-C$_5$ straight chain or branched chain alkyl or a C$_1$-C$_4$ straight chain or branched chain haloalkyl.

The present invention relates to compounds useful as sigma receptors of the following formula V:

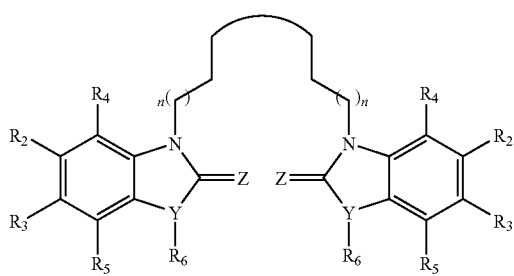

V

Wherein R$_{2,3,4,5,6}$ can each independently be any one or combinations of the following moieties, such as, for example, cyano, nitro, acyl, alkyl, amido, azido, isothiocyanate, isocyanate anilino (unsubstituted or substituted), halogens (such as fluorine, chlorine, bromide and iodine), ethers, sulfonamides, thioacyl, nitro, aromatic, heterocyclic, olefinic, acetylenic, deuterium, or tritium; Y can be either CH, CH$_2$, O, S, OCH$_2$, N—R, N—Ar, C—R, C—Ar where Ar is an optionally substituted aryl. Z can be either H, O, S, S—R or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The R$_1$ bridging moiety in the formula V can be an optionally substituted C$_1$-C$_6$ alkylene, C$_1$-C$_6$ alkenylene or C$_1$-C$_6$ alkynylene group wherein the alkylene group can have inserted into its chain a C$_3$-C$_5$ cycloalkyl group, aromatic, and heterocyclic group.

DETAILED DESCRIPTION OF THE INVENTION

Figure 1:
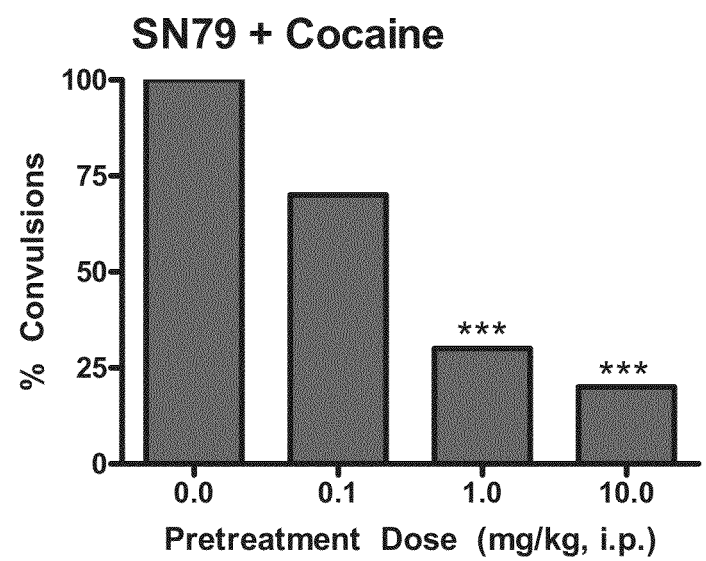
FIG. 1—SN79 attenuates the convulsive effects of cocaine (***P<0.005)
Figure 2:
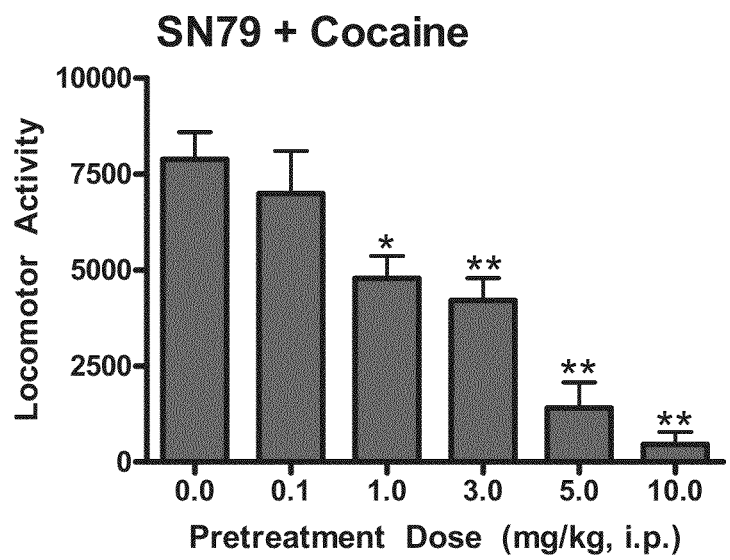
FIG. 2—SN79 pretreatment attenuates cocaine-induced locomotor activity (*P<0.05, **P<0.01)
Figure 3:
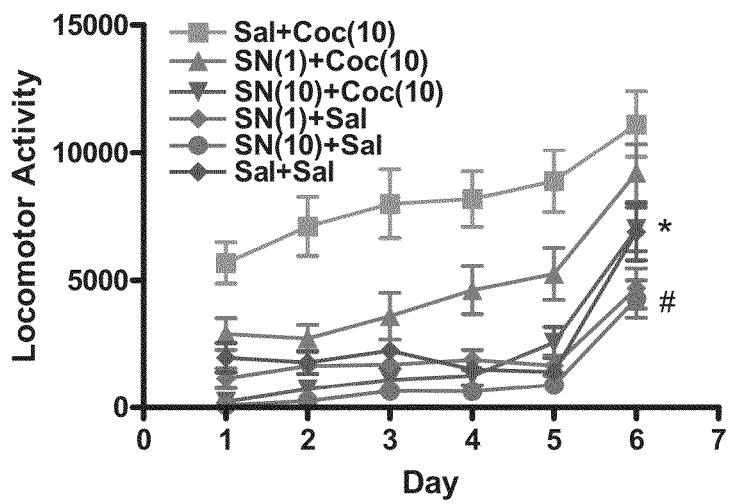
FIG. 3—SN79 pretreatment attenuates the development of cocaine-induced sensitization (*P<0.05, #P<0.05)
Figure 4:
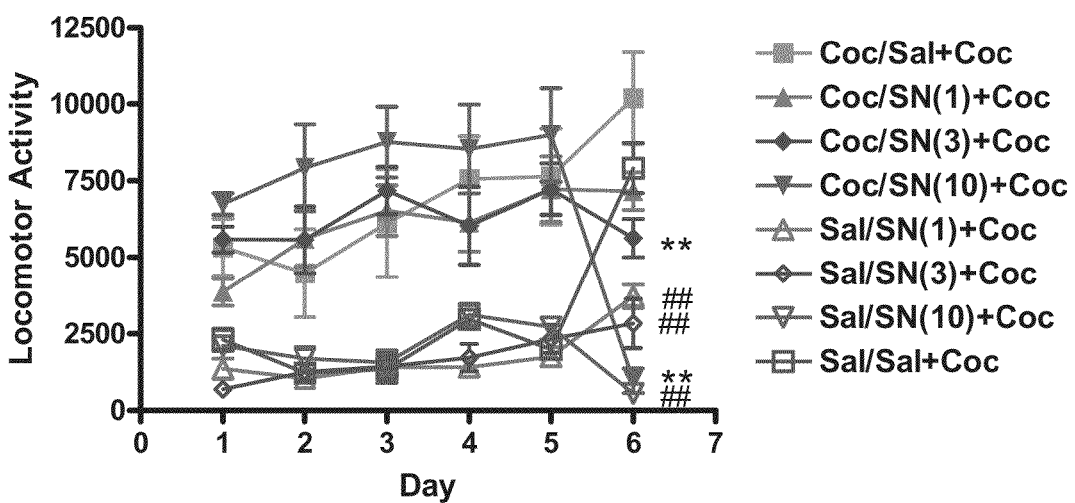
FIG. 4—SN79 pretreatment attenuates the expression of cocaine-induced sensitization (**P<0.05 vs sensitized, ##P<0.05 vs acute cocaine)

The generic structures of Formulae I, II, III, IV and V encompasses a diverse range of heterocycles. Embodiments within this genus, for example, include 2(3H)-benzoxazolone (Y=O, Z=O) and 2(3H)-benzothiazolone (Y=S, Z=O) compounds and the sigma receptor affinity shown by these heterocycles. The 2(3H)-benzoxazolone (BOA) and its bioisosteric surrogate 2(3H)-benzothiazolone (BTA) heterocycle is a bicyclic ring system which promotes high versatility in organic synthesis involving N-substitution (either N-alkylation or N-acylation) and aromatic ring electrophilic substitution reactions.

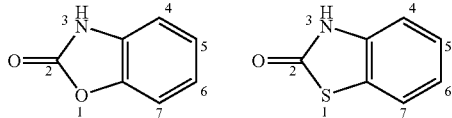

2(3H)-Benzoxazolone (BOA)    2(3H)-Benzothiazolone (BTA)

Chemical Structures of BOA and BTA

The present invention relates to compounds having the general formula I

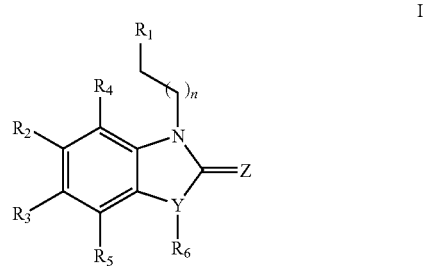

I wherein R$_1$ can be a radical of an optionally substituted C-4 to C-7 N-containing heterocycle or a radical of an optionally substituted cyclic or acyclic tertiary amine, or isoindoline-1,3-dioneR$_{2,3,4,5,6}$ can each independently be any one or combinations of the following moieties, cyano, nitro, acyl, alkyl, amido, azido, isothiocyanates, isocyanates, optionally substituted anilino, halogens, ethers, sulfonamides, thioacyl, nitro, aromatic, heterocyclic, olefinic, acetylene, deuterium, or tritium; Y can be either CH, CH$_2$, O, S, OCH$_2$, N—R, N—Ar, C—R, C—Ar; Z can be either H, O, S, S—R or NR. R groups can be either H, aryls, alkyls, or cycloalkyls; "n" can be 1 to 5 carbons in length and stereoisomers, functional analogs, and pharmaceutically acceptable salts thereof and wherein the moiety bridging R$_1$ and N can be optionally substituted alkylene, optionally substituted alkenylene or optionally substituted alkynylene and where the alkylene group can include an inserted C$_3$-C$_5$ cycloalkyl group, aromatic and heterocycle group.

The optionally substituted N-containing heterocyclic radical can be for example optionally substituted piperidine, optionally substituted tetrahydropiperidine, optionally substituted piperazine, optionally substituted tetrahydropyridine, optionally substituted azepanes or optionally substituted tetrahydroisoquinoline in which the optional substituents are on the aromatic moiety.

The present invention further relates to compounds useful as sigma receptors of the following formula II:

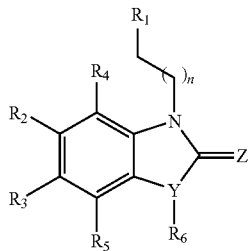

II

Wherein $R_1$ can be an optionally substituted nitrogen-containing heterocycle radical such as, for example, radicals of optionally substituted piperidines, optionally substituted piperazines, optionally substituted tetrahydropyridines, optionally substituted azepanes, tertiary amines (cyclic or acyclic), isoindoline-1,3-dione, or optionally substituted tetrahydroisoquinolones (aromatically substituted): $R_{1,4,5,6}$ can each independently be any one or combinations of the following moieties, such as, for example, cyano, nitro, acyl, alkyl, amido, azido, isothiocyanate, isocyanate anilino (unsubstituted or substituted), halogens (such as fluorine, chlorine, bromide and iodine), ethers, sulfonamides, thioacyl, nitro, aromatic, heterocyclic, olefinic, acetylenic, deuterium, or tritium; Y can be either CH, $CH_2$, O, S, $OCH_2$, N—R, N—Ar, C—R, C—Ar where Ar is an optionally substituted aryl. Z can be either H, O, S, S—R or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The moiety bridging $R_1$ and N in the formula II can be a substituted $C_1$-$C_6$ alkylene, $C_1$-$C_6$ alkenylene wherein the alkylene group can have inserted into its chain a $C_3$-$C_5$ cycloalkyl group, aromatic, and heterocyclic group.

Formulae I and II differ from each other only in the definition of the moiety bridging R1 and N.

The present invention relates to still yet further compounds useful as sigma receptors of the following formula III:

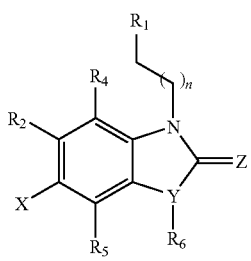

III

Wherein $R_1$, $R^{2,4,5,6}$ and "n" can be the options provided for formula II, above and wherein $X_1$ is halogen, or $C_1$-$C_4$ haloalyl.

The present invention relates to a still yet further series of compounds useful as sigma receptors of the following formula IV:

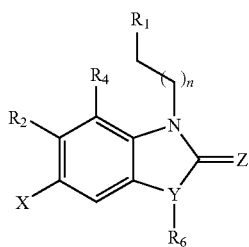

IV

Wherein $R_1$ can be an optionally substituted nitrogen-containing heterocycle radical such as, for example, radicals of optionally substituted piperidines, optionally substituted piperazines, optionally substituted tetrahydropyridines, optionally substituted azepanes, tertiary amines (cyclic or acyclic), isoindoline-1,3-dione, or optionally substituted tetrahydroisoquinolones (aromatically substituted): $R_{2,4,6}$ can each independently be any one or combinations of the following moieties, such as, for example, cyano, nitro, acyl, alkyl, amido, azido, isothiocyanate, isocyanate anilino (unsubstituted or substituted), halogens (such as fluorine, chlorine, bromide and iodine), ethers, sulfonamides, thioacyl, nitro, aromatic, heterocyclic, olefinic, acetylenic, deuterium, or tritium; Y can be either CH, $CH_2$, O, S, $OCH_2$, N—R, N—Ar, C—R, C—Ar where Ar is an optionally substituted aryl. Z can be either H, O, S, S—R or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The moiety bridging $R_1$ and N in the formula IV can be a substituted $C_1$-$C_6$ alkylene having the formula —($CHR_x$—($CH_2$)—$CH_2$)— wherein the —$CHR_x$— moiety is attached to $R_1$ and the alkylene group can have inserted into its chain a $C_3$-$C_5$ cycloalkyl group, aromatic, and heterocyclic group and wherein the $R_x$ is a $C_1$-$C_4$ straight chain or branched chain alkyl or a $C_1$-$C_4$ straight chain or branched chain haloalkyl.

The present invention relates to compounds useful as sigma receptors of the following formula V:

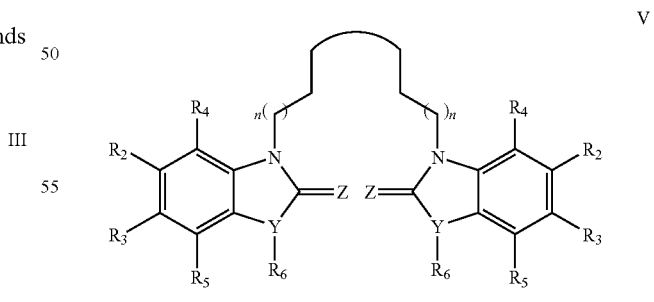

V

Wherein $R_{2,3,4,5,6}$ can each independently be any one or combinations of the following moieties, such as, for example, cyano, nitro, acyl, alkyl, amido, azido, isothiocyanate, isocyanate anilino (unsubstituted or substituted), halogens (such as fluorine, chlorine, bromide and iodine), ethers, sulfonamides, thioacyl, nitro, aromatic, heterocyclic, olefinic, acetylenic, deuterium, or tritium; Y can be either CH, $CH_2$, O, S, $OCH_2$, N—R, N—Ar, C—R, C—Ar where Ar is an optionally substituted aryl. Z can be either H, O, S, S—R or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The $R_1$ bridging moiety in the formula V can be an optionally substituted $C_1$-$C_6$ alkylene, $C_1$-$C_6$ alkenylene or $C_1$-$C_6$ alkynylene group wherein the alkylene group can have inserted into its chain a $C_3$-$C_5$ cycloalkyl group, aromatic, and heterocyclic group.

Exemplary compounds of the invention can be of the general formulae shown below in which n=1-5:

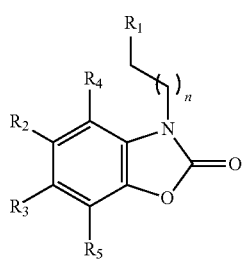

IIA

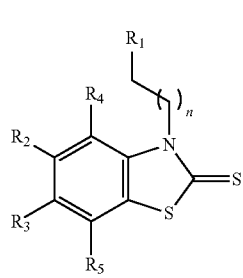

IIB

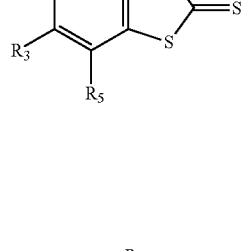

IIC

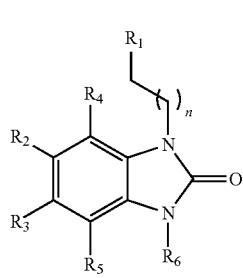

IID

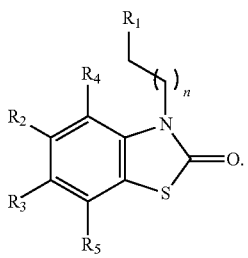

IIE

Further exemplary compounds of the invention can be of the general formulae shown below in which n=1-5:

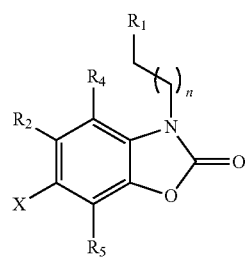

IIIA

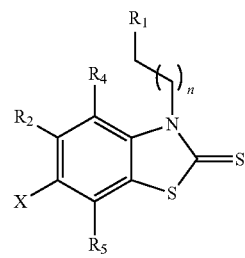

IIIB

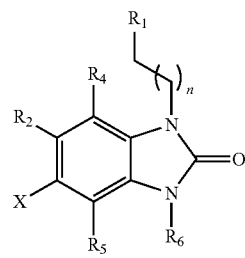

IIIC

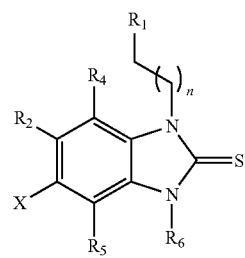

IIID

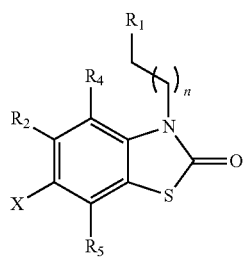
IIIE
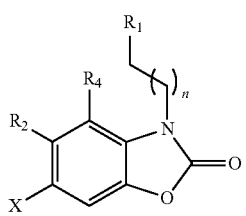
IVA
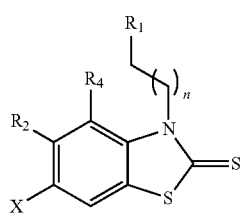
IVB
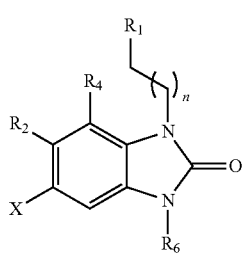
IVC
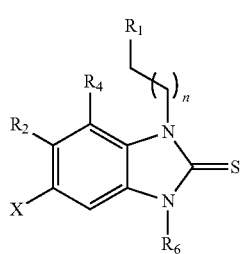
IVD
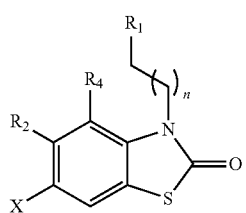
IVE
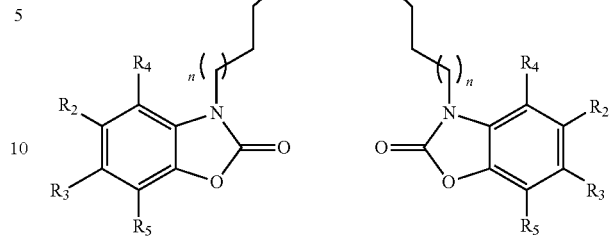
VA
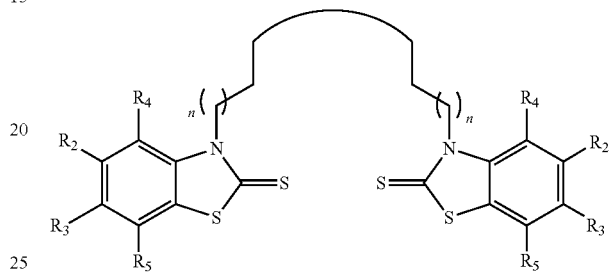
VB
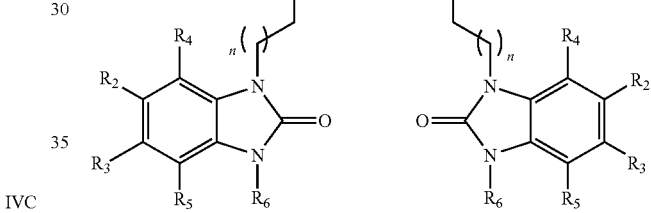
VC
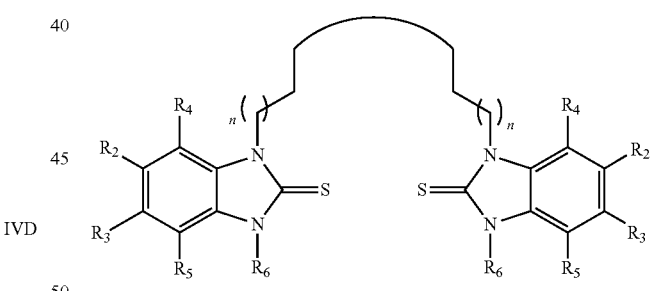
VD
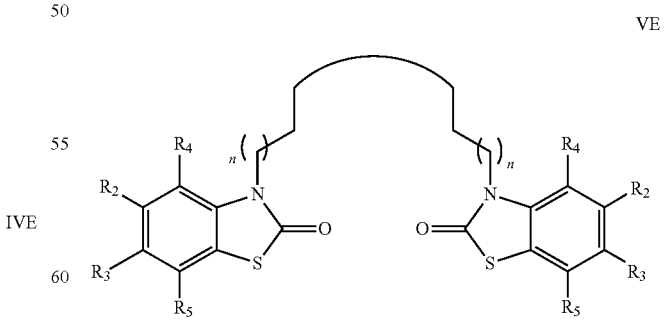
VE
Other exemplary compounds of the invention are compounds where Y=O and Z=O; or Y=S and Z=S; or where Y=CH$_2$ or Y=CH.

$R_1$ for example is optionally substituted

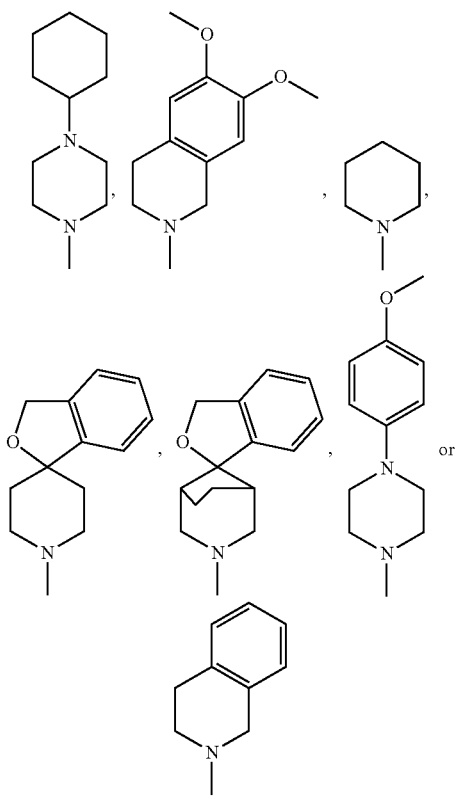

DEFINITIONS OF TERMS

As used herein, the term "lower" refers to a group having between one and six carbons.

As used herein, the term "alkyl" refers to a straight or branched chain hydrocarbon having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, azido, isothiocyanate, isocyanate, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkyl" group may contain one or more O, S, S(O), or S(O)$_2$ atoms. Examples of "alkyl" as used herein include, but are not limited to, methyl, n-butyl, t-butyl, n-pentyl, isobutyl, and isopropyl, and the like.

As used herein, the term haloalkyl refers to a straight or branched chain alkyl having one to four carbon atoms in which at least one H up to all of the H's of the alkyl is substituted with a halo moiety wherein halo includes fluoro, chloro, bromo or iodo.

As used herein, the term "alkylene" refers to a straight or branched chain divalent hydrocarbon radical having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkylene" group may contain one or more O, S, S(O), or S(O)$_2$ atoms. Examples of "alkylene" as used herein include, but are not limited to, methylene, ethylene, and the like.

As used herein, the term "alkenyl" refers to a hydrocarbon radical having from two to ten carbons and at least one carbon-carbon double bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenyl" group may contain one or more O, S, S(O), or S(O)$_2$ atoms.

As used herein, the term "alkenylene" refers to a straight or branched chain divalent hydrocarbon radical having from two to ten carbon atoms and one or more carbon-carbon double bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenylene" group may contain one or more O, S, S(O), or S(O)$_2$ atoms. Examples of "alkenylene" as used herein include, but are not limited to, ethene-1,2-diyl, propene-1,3-diyl, methylene-1,1-diyl, and the like.

As used herein, the term "alkynyl" refers to a hydrocarbon radical having from two to ten carbons and at least one carbon-carbon triple bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynyl" group may contain one or more O, S, S(O), or S(O)$_2$ atoms.

As used herein, the term "alkynylene" refers to a straight or branched chain 5 divalent hydrocarbon radical having from two to ten carbon atoms and one or more carbon-carbon triple bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynylene" group may contain one or more O, S, S(O), or S(O)$_2$ atoms. Examples of "alkynylene" as used herein include, but are not limited to, ethyne-1,2-diyl, propyne-1,3-diyl, and the like.

As used herein, "cycloalkyl" refers to an alicyclic hydrocarbon group optionally possessing one or more degrees of unsaturation, having from three to twelve carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like.

As used herein, the term "cycloalkylene" refers to a non-aromatic alicyclic divalent hydrocarbon radical having from three to twelve carbon atoms and optionally possessing one or more degrees of unsaturation, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl 1,3-diyl, cyclohexyl-1,4-diyl, cycloheptyl-1,4-diyl, or cyclooctyl-1,5-diyl, and the like.

As used herein, the term 'heterocyclic" or the term "heterocyclyl" refers to a three to twelve-membered heterocyclic ring optionally possessing one or more degrees of unsaturation, containing one or more heteroatomic substitutions selected from S, SO, SO$_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, 1,4-dioxane, 1,3-dioxane, piperidine, pyrrolidine, morpholine, piperazine, tetrahydropyridine, hexagydroazepine and the like.

As used herein, the term 'heterocyclyl containing at least one basic nitrogen atom" refers to a "heterocyclic" or "heterocyclyl" group as defined above, wherein said heterocyclyl group contains at least one nitrogen atom flanked by 20 hydrogen, alkyl, alkylene, or alkylyne groups, wherein said alkyl and/or alkylene groups are not substituted by oxo. Examples of "heterocyclyl containing at least one basic nitrogen atom" include, but are not limited to, piperazine-2-yl, pyrrolidine-2-yl, azepine-4-yl,

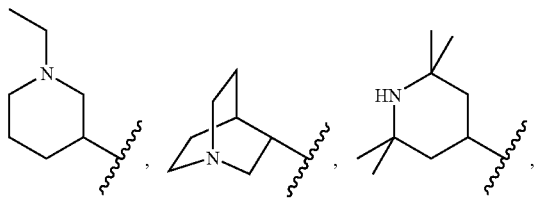

-continued

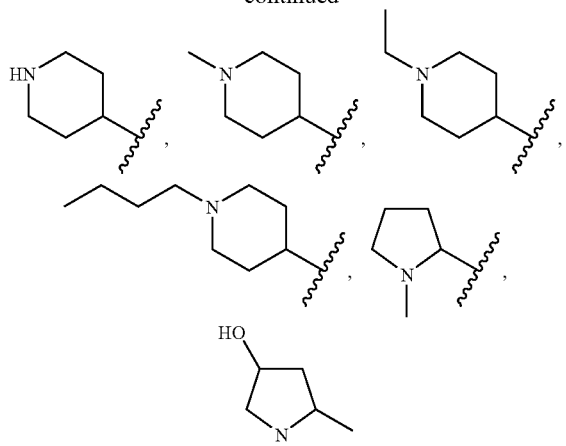

and the like.

As used herein, the term "heterocyclylene" refers to a three to twelve-membered heterocyclic ring diradical optionally having one or more degrees of unsaturation containing one or more heteroatoms selected from S, SO, SO$_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, piperazine-1,4-diyl, and the like.

As used herein, the term "aryl" refers to a benzene ring or to an optionally substituted benzene ring system fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy optionally substituted by acyl, mercapto, azido, isothiocyanate, isocyanate, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower periluoroalkyl, multiple degrees of substitution being allowed. Examples of aryl include, but are not limited to, phenyl, 2-naphthyl, 1-naphthyl, 1-anthracenyl, and the like.

As used herein, the term "arylene" refers to a benzene ring diradical or to a benzene ring system diradical fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "arylene" include, but are not limited to, benzene-1,4-diyl, naphthalene-1,8-diyl, and the like.

As used herein, the term "heteroaryl" refers to a five- to seven-membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, quinazoline, benzofuran, benzothiophene, indole, and indazole, and the like.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, halo includes fluoro, bromo and iodo.

Initial efforts were focused on incorporating a good directionality by implying side-chains on a rigid template using conventional simple synthetic methodology. Exploring the effects of linker length between two hydrophobic regions for sigma receptor affinity led to the synthesis of 2 to 6 carbon linkers of 2(3H)-benzoxazolones ligands and 2(3H)-benzothiazolones compounds.

The in vitro receptor binding affinities of the initial series of compounds of formulae II and III investigated in rat brain homogenates at σ-1 and σ-2 subtypes are summarized in tables 1 and 2.

TABLE 1

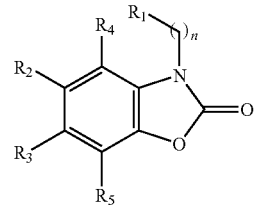

Initial series 2(3H)-benzoxazolones to explore the effects of linker length on sigma receptor affinity

| Compd. | $R_1$ | $R_2$-$R_5$ | n | σ-1 ($K_i$, nM) | σ-2 ($K_i$, nM) | σ-1/σ-2 |
|---|---|---|---|---|---|---|
| CM-129 | | H | 2 | 6.90 ± 0.37 | 5.43 ± 0.78 | 1.3 |
| CM-124 | | H | 3 | 5.22 ± 1.11 | 8.74 ± 2.30 | 0.6 |
| CM-121 | | H | 4 | 11.3 ± 1.25 | 1.83 ± 0.17 | 6.2 |
| CM-126 | | H | 5 | 10.6 ± 2.52 | 5.89 ± 1.31 | 1.8 |

TABLE 1-continued

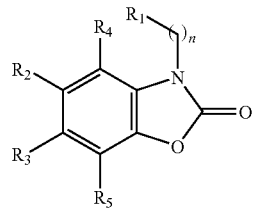

Initial series 2(3H)-benzoxazolones to explore the effects of linker length on sigma receptor affinity

| Compd. | $R_1$ | $R_2$-$R_5$ | n | σ-1 ($K_i$, nM) | σ-2 ($K_i$, nM) | σ-1/σ-2 |
|---|---|---|---|---|---|---|
| SN-48 | —N(piperazine)N-cyclohexyl | H | 6 | 4.60 ± 1.08 | 3.06 ± 0.45 | 1.5 |

TABLE 2

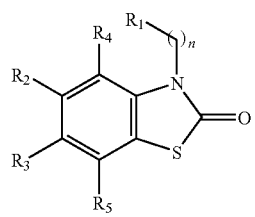

Initial series 2(3H)-benzothiazolones to explore the effects of linker length on sigma receptor affinity

| Compd. | $R_1$ | $R_2$-$R_5$ | n | σ-1 ($K_i$, nM) | σ-2 ($K_i$, nM) | σ-1/σ-2 |
|---|---|---|---|---|---|---|
| SN-97 | —N(piperazine)N-cyclohexyl | H | 2 | 4.66 ± 0.74 | 2.25 ± 0.37 | 2.1 |
| SN-98 | —N(piperazine)N-cyclohexyl | H | 3 | 5.61 ± 0.74 | 3.05 ± 0.41 | 1.84 |
| CM-145 | —N(piperazine)N-cyclohexyl | H | 4 | 4.17 ± 0.62 | 0.39 ± 0.06 | 10.69 |
| SN-99 | —N(piperazine)N-cyclohexyl | H | 5 | 4.98 ± 0.42 | 2.44 ± 0.26 | 2.04 |
| SN-102 | —N(piperazine)N-cyclohexyl | H | 6 | 6.55 ± 0.25 | 1.49 ± 0.18 | 4.40 |

CM121 showed a six fold preference for the σ-2 subtype, suggesting that a four methylene spacer between the piperazine ring and the heterocycle may favor σ-2 affinity (Table 1, Scheme 1). During further SAR studies, compound CM170 was found to have an 11 fold preference for the σ-2 subtype, suggesting a 4-fluoropiperazine moiety may favor σ-2 affinity (Scheme 1). Additionally, CM142 having a 6-acetyl group in the 2(3H)-benzoxazolone heterocycle increased the preference for σ-2 receptors by 7 fold (Scheme 1).

Scheme 1: Sigma-2 selective ligands

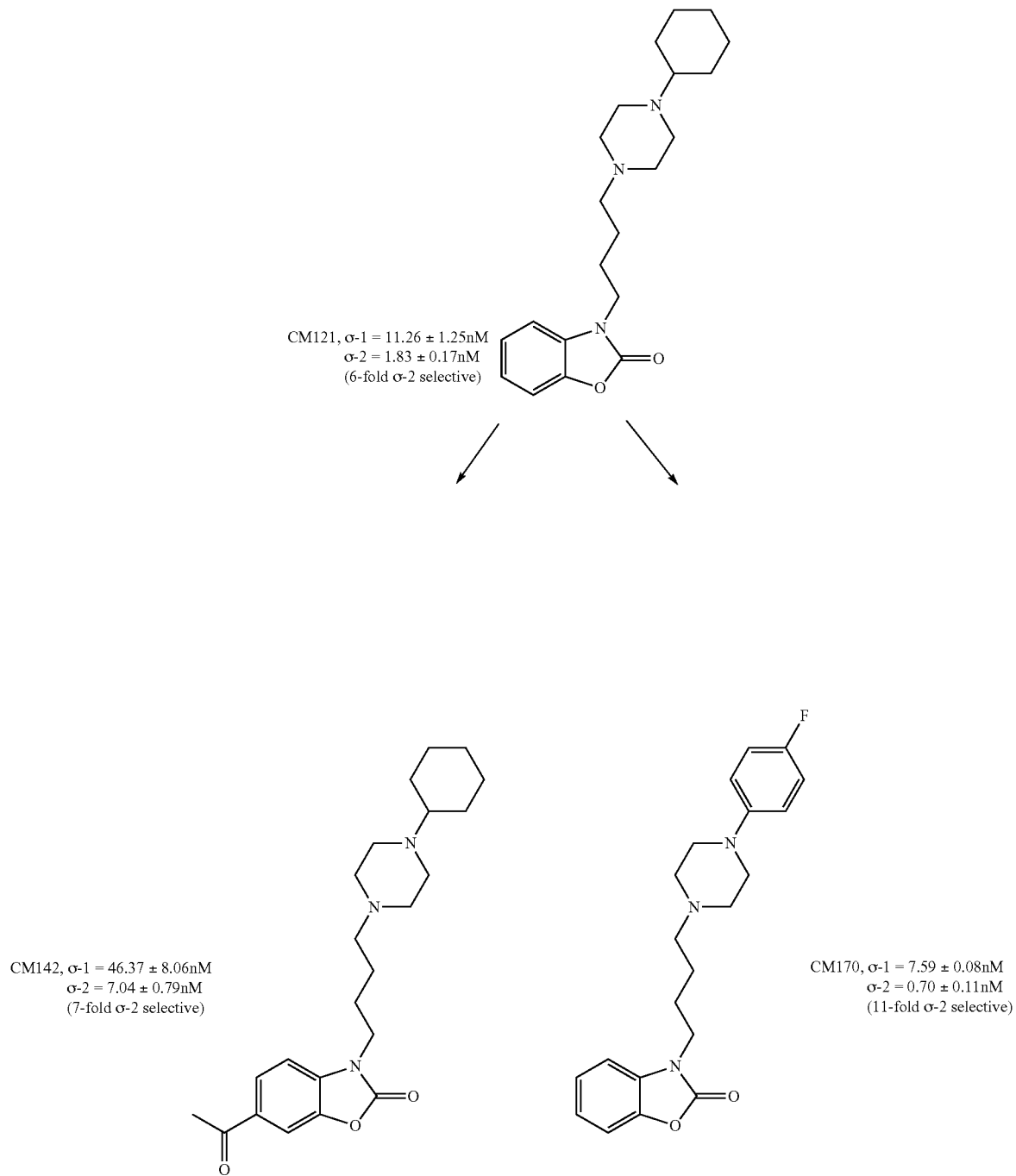

Interestingly, SN79 (Scheme 2) showed the high selectivity (>16,500 fold) for the σ-2 subtype suggesting that a four methylene linker, a 6-acetyl group in the 2(3H)-benzoxazolone heterocycle and a 4-fluoropiperazine moiety favor σ-2 affinity over the σ-1 subtype.

Scheme 2: Compound SN79

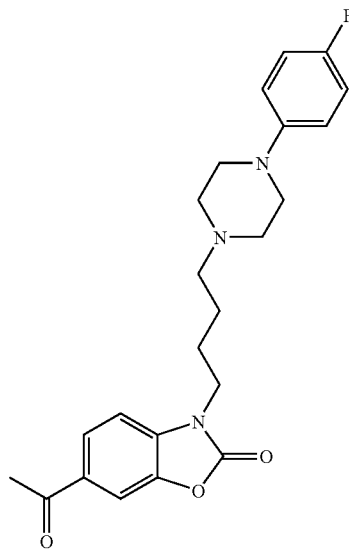

SN79, σ-1 = > 100,000 nM
σ-2 = 6.06 ± 0.74 nM
( > 16500 fold σ-2 selective)

When tested on select non-sigma binding sites in rat brain homogenates (Table 3), compound SN79 exhibited weaker interactions, confirming preferential affinity for sigma receptors.

TABLE 3

Non-sigma binding affinity of SN79

| Monoamine transporters | $K_i$, nM | Other Receptors | $K_i$, nM |
| --- | --- | --- | --- |
| DAT | 2615 ± 62 | Opioid | >10,000 |
| SERT | 159 ± 15 | NMDA | >10,000 |
| NET | 177 ± 14 | Dopamine ($D_2$) | >10,000 |
|  |  | 5-$HT_2$ | 320 ± 16 |

Compound SN79 was investigated for in vivo antagonizing effects in cocaine treated mice. Pretreatment of mice with SN79 led to a significant attenuation of cocaine-induced convulsions, locomotor activity and behavioral sensitization as seen in FIGS. 1-4. These data further demonstrate that compound SN79, acting through σ-2 receptors is able to significantly attenuate both the acute effects of cocaine as well as its chronic effects.

In addition to compounds exhibiting selectivity for the σ-2 receptor, compounds from this same series have demonstrated high affinity for both subtypes. Compound CM156 (Scheme 3), where the 2-oxo is replaced with a sulfur, demonstrated the highest affinity for both subtypes and was therefore examined in several non-sigma binding assays as shown in table 4. CM 156 had much weaker affinity for other proteins of interest, confirming preferential affinity for sigma receptors.

Scheme 3: Compound CM156

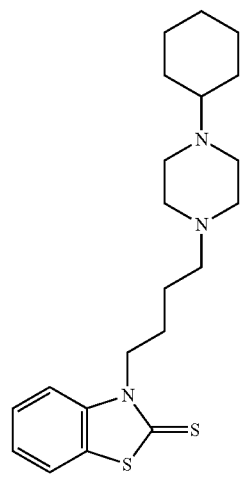

CM 156 σ-1 = 1.28 ± 0.38nM
σ-2 = 0.55 ± 0.08nM

TABLE 4

Non-sigma binding affinity of CM156

| Monoamine transporters | $K_i$, nM | Other Receptors | $K_i$, nM |
| --- | --- | --- | --- |
| DAT | 1175 ± 10 | Opioid | >10,000 |
| SERT | 1402 ± 152 | NMDA | >10,000 |
| NET | >10,000 | Dopamine ($D_2$) | 1041 ± 9 |
|  |  | 5-$HT_2$ | 1326 ± 159 |

Figure 5:
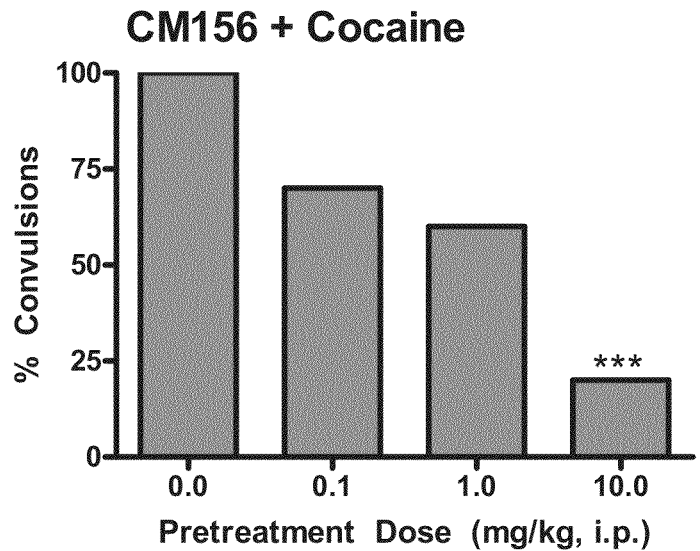
FIG. 5—CM156 attenuates the convulsive effects of cocaine (***P<0.005)
Figure 6:
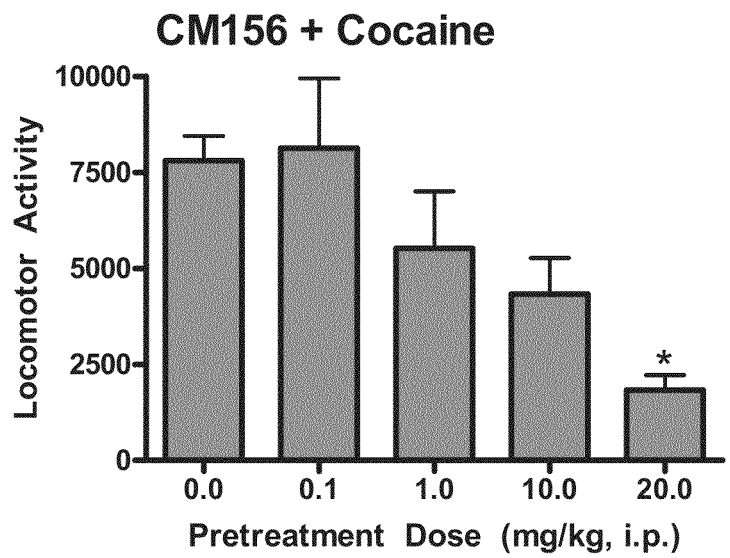
FIG. 6—CM156 pretreatment attenuates cocaine-induced locomotor activity (*P<0.05)
Figure 7:
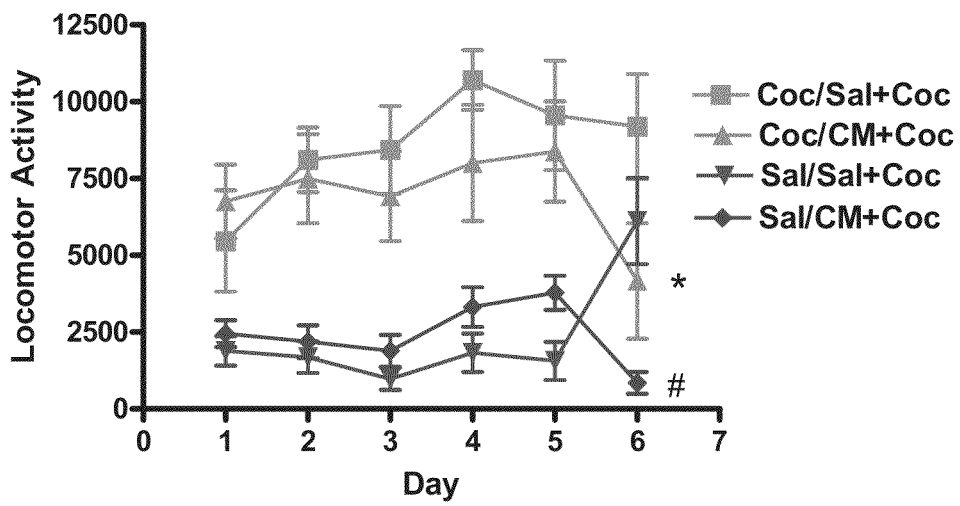
FIG. 7—CM156 pretreatment attenuates the expression of cocaine-induced sensitization (*P<0.05 vs sensitized, #P<0.05 vs acute cocaine)
Figure 8:
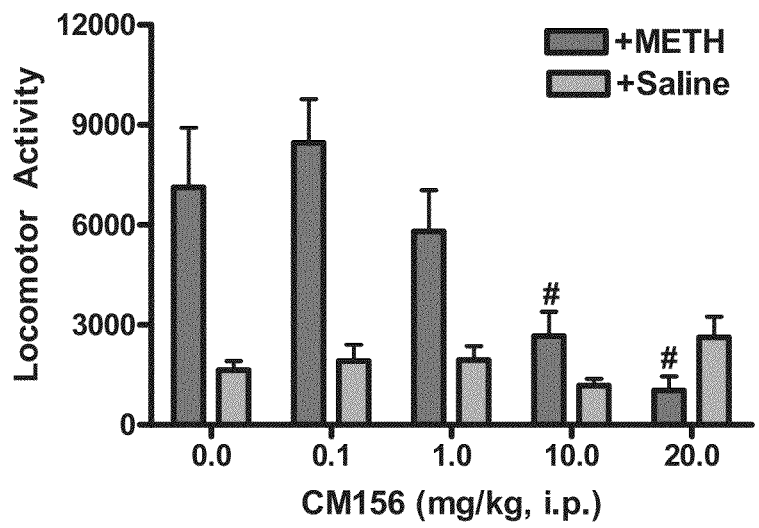
FIG. 8—CM156 pretreatment attenuates methamphetamine-induced locomotor activity (#P<0.05)
Figures 9, 10:
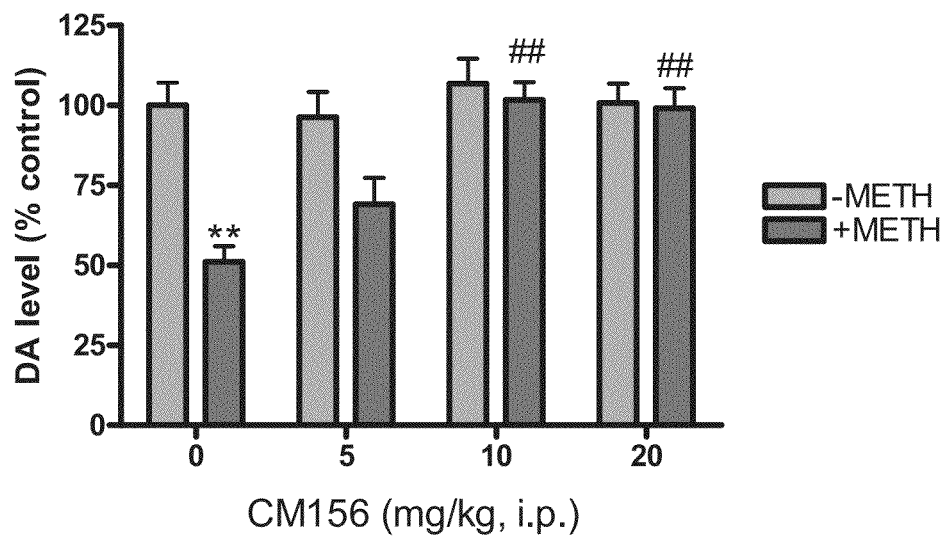
FIG. 9—CM156 pretreatment attenuates methamphetamine-induced dopamine depletions (**P<0.05, ##P<0.05)
FIG. 10—Table 1: Metabolic stability of AZ_66 by Rat liver microsomes (1 mg/ml)
Figures 11, 12, 13:
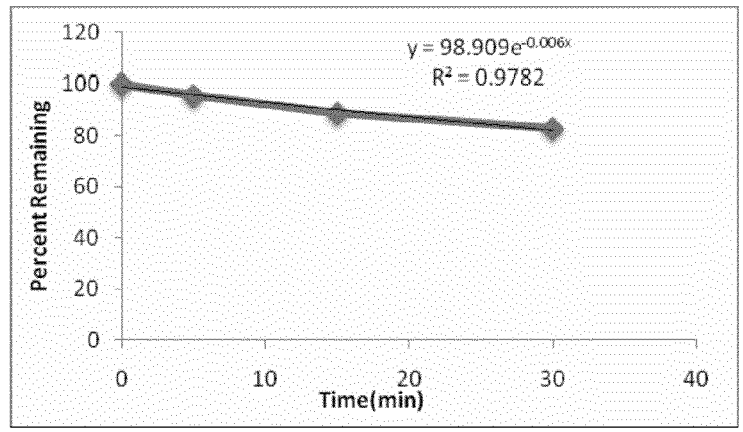
FIG. 11—Metabolic stability of AZ_66 by Rat liver microsomes (1 mg/ml)
FIG. 12—Table 2: In vitro Half-life and Intrinsic clearance
FIG. 13—Table 3: Incubation of CM_156 (10 μM) with rat liver microsomes (1 mg/ml)

Compound CM156 was further investigated in vivo for antagonizing effects in cocaine treated mice. Pretreatment of mice with CM156 led to a significant attenuation of cocaine-induced convulsions, locomotor activity and behavioral sensitization as seen in FIGS. 5-7. Compound CM156 was additionally investigated for its ability to attenuate methamphetamine-induced locomotor stimulation and neurotoxicity in mice. As seen in FIGS. 8 and 9, CM156 attenuated the locomotor stimulant effects of methamphetamine as well as the neurotoxic effects resulting from methamphetamine exposures. Together, these data demonstrate that CM156 with high affinity for both a subtypes can mitigate a variety of drug-induced effects, both from cocaine and methamphetamine, in vivo.

Metabolic Stability of AZ__66 in Rat Liver Microsomes

AIM: To study the metabolic stability of AZ__66 in Rat liver microsomes.

Analytical Method Set Up

For the metabolism studies of AZ__66, an isocratic method was developed using UPLC/MS/MS.

Chromatographic Conditions

Mobile phase A: 0.3% Formic acid in water, 10 mM Ammonium Formate (50%)

Mobile phase B: 0.1% Formic acid in Methanol (50%)

Column: Atlantis dC18 (2.1×50 mm, 5 µm)

Flow rate: 0.2 mL/min

Injection volume: 10 µl

Mass Parameters

The detection of the analyte was carried out using ESI+ve mode. The MS conditions were as follows: Capillary voltage 4.88V, Cone voltage 46V, Extractor voltage 3V, RF lens voltage 0.5V. The source and Desolvation temperatures were 120° C. and 250° C. respectively, and the Desolvation and cone gas flows were 500 and 60 L/hr respectively. The selected mass-to-charge (m/z) ratio transition of AZ-66 ions [M+H]$^+$ used in the single ion reaction (SIR) was m/z: 406.2

Method

Metabolic stability of AZ_66 (1 µM) was performed in Ammonium acetate buffer (50 mM, pH 7.4) with Rat liver microsomes (0.5 mg) at 37° C. in 0.5 ml of incubation mixture. The incubation mixture composed of Ammonium acetate buffer (50 mM, pH 7.4), Magnesium chloride (3 mM), NADPH regenerating system consisting of NADP (1 mM), glucose-6-phosphate (5 mM), and glucose-6-phosphate dehydrogenase (1 Unit/mL). The Substrate and microsomes were pre incubated at 37° C. for 5 min before starting the reaction. The reactions were started by the addition of regenerating system and carried out at 37° C. in a shaking water bath for 60 min. The incubations were stopped by adding equal volume of ice cold acetonitrile at predetermined time points (0, 5, 15, 30, 60 min). The samples were centrifuged for 10 min at 4° C. and the supernatant was injected in to UPLC/MS/MS. Control incubation without NADPH was also performed and these served as 100% value. All microsomal incubations were conducted using the same lot of microsomes.

Additional Controls

Additional incubations were performed using rat liver microsomes at same experimental conditions with CM_156 (10 µM). This served as a positive control to determine if the test system used in this study were metabolically competent.

In vitro half-life and CLint: The percent of the parent compound remaining is plotted versus time. The slope of the line gives the rate constant k for the disappearance of parent compound, from which an in vitro $t_{1/2}$ can be calculated. CLint can be calculated using the following formula $$CLint = k(\text{min}^{-1}) \times \frac{[V](L)}{[P](\text{mg})} = (L/\text{mg} \times \text{min})$$

[V] is the incubation volume in µl and [P] is the amount of microsomal protein in the incubation.

Results

The metabolism of AZ_66 was investigated in vitro using rat liver microsomes for 60-min. The estimated $t_{1/2}$ for disappearance of AZ_66 in rat liver microsomes was 115.56±15 min. Linear part of the Concentration vs Time graph was selected for the half-life calculations i.e. from 0-30 min. The estimated CLint from microsomes was 0.006 ml/min/mg. The CLint whole liver of AZ_66 1 µM was 0.002434 L/min. There is no loss of substrate in the absence of cofactor indicating that the loss of AZ_66 is through metabolism by NADPH-dependent enzymes.

AZ_66 was found to be stable in rat liver microsomes even after 60 min of incubation. Microsomes metabolized about 25% of the added substrate by 60 min. The results revealed that the metabolism was slow and continued at a linear rate for 30 min with an apparent departure from linearity after 30 min. The deviation from linearity may be due to limiting amounts of substrate or known organic and inorganic cofactors.

The substantial stability of the compound may be attributed to the C—F bond and oxygen in the thiazole ring. The other possible reason for higher stability could be the presence of methyl group preventing the N-dealkylation.

It may be concluded that the rate of metabolism could be decreased by incorporation of appropriate substituents at the primary sites of metabolism. See FIGS. 10, 11, 12, and 13.

The compounds of the present invention are for use as novel radioligands and agents for treatment of drugs of abuse including cocaine- and methamphetamine-induced abuse and toxicities.

Experimental

Chemical Synthesis of Novel a Antagonists

Compounds can be modified in several positions to investigate the effects around the core structure on σ-1 and σ-2 affinities and activities. It has been demonstrated that one can substitute the template molecule through several synthetic routes. These routes which can be easily performed utilizing parallel synthesis methodology, can be easily varied to obtain multiple novel ligands. Initial studies focused on exploring the following changes to the molecules through parallel methodologies: I) varying the methylene spacer between the tertiary amine and heterocycle; 2) modifying substituents to the piperazine nitrogen above the template; 3) modifying the piperazine ring to substitute piperidines, tetrahydropyridines, azepanes and diazepines; 4) modifying the order of heteroatoms in the heterocycle portion of the molecule as well as the connectivity pattern; and 5) substitution on the benzo portion of the heterocycle to probe the space and physicochemical requirements of the σ receptors.

Compounds were analyzed after purification using standard techniques (NMR, IR, LC/MS, HPLC) and converted into hydrochloride salts for water solubility. Final purity of compounds were achieved through melting points and elemental analysis. When necessary, X-ray crystallography was performed.

Syntheses of 2(3H)-benzoxazolones and 2(3H)-benzothiazolones were accomplished by multistep solution phase synthesis as shown Scheme 4. Synthesis involved simple base-mediated alkylation and Friedel-Craft's alkylation reactions.

Scheme 4.
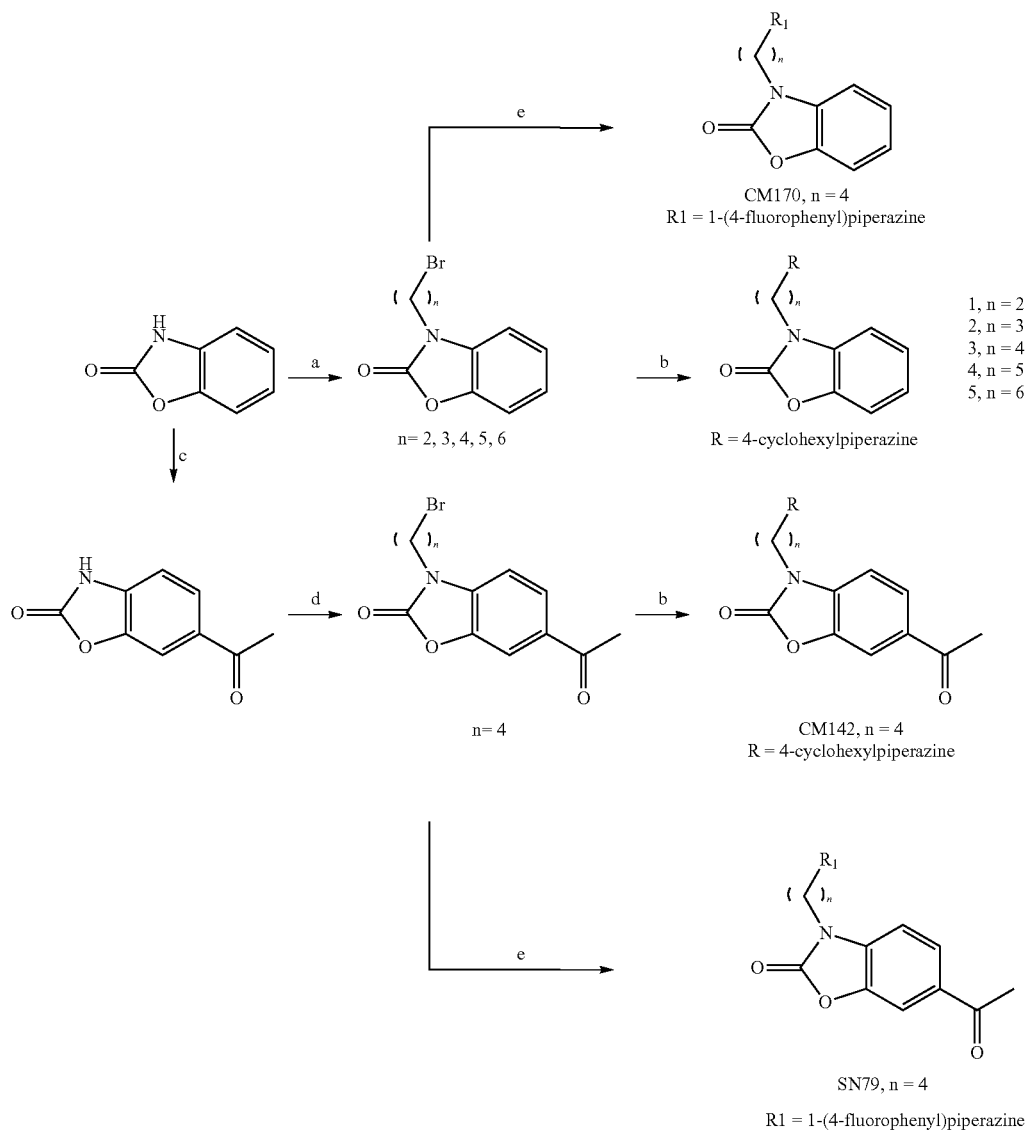
Reagents and conditions: a) Dibromoalkane, K₂CO₃, DMF, 60° C., 2 h; b) 1-cyclohexylpiperazine, K₂CO₃, DMF, 60° C., 3 h; c) (CH₃CO)₂O, AlCl₃, 75° C., 4 h; d) 1,4-dibromobutane, K₂CO₃, DMF, 60° C., 2 h; e) 1-(4-fluorophenyl)piperazine, K₂CO₃, DMF, 60° C., 4 h
Sigma compounds - synthetic scheme
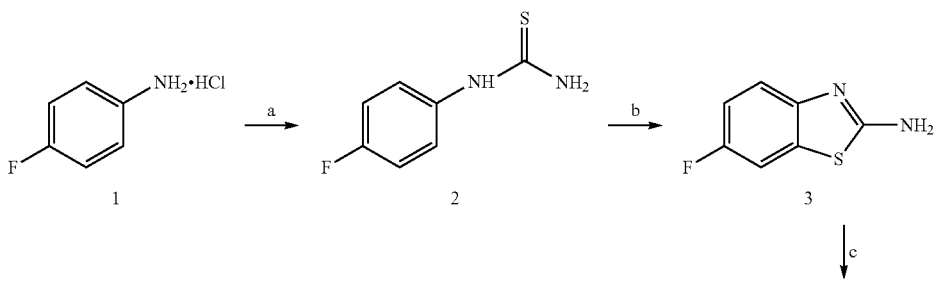

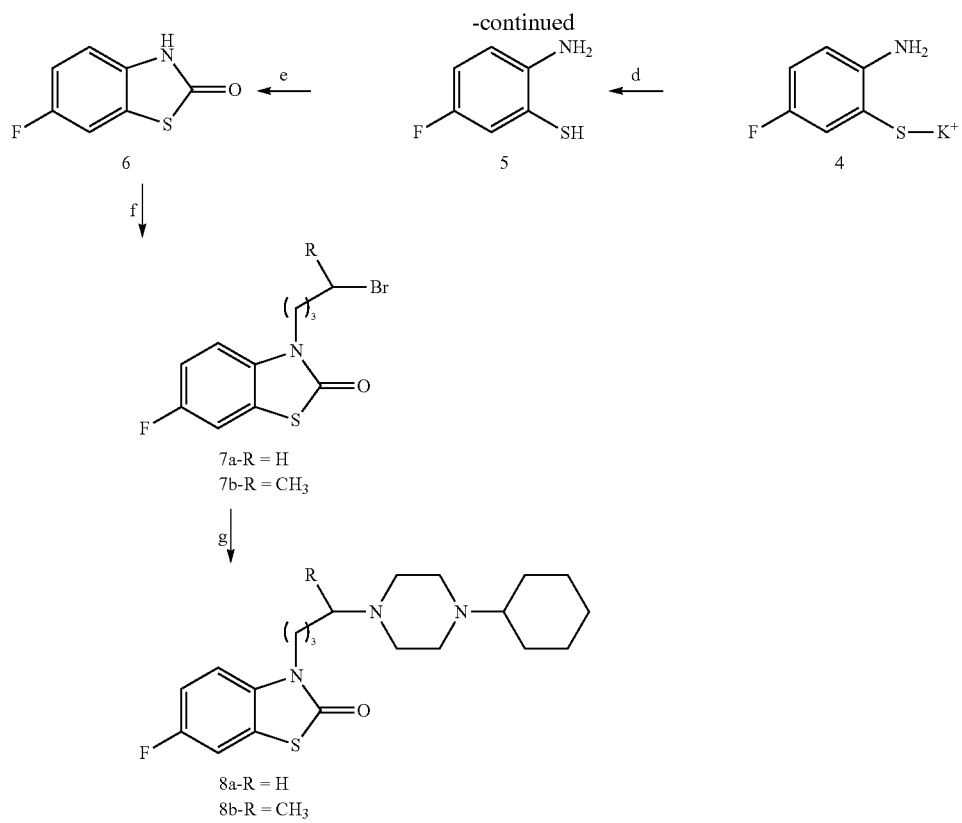

Reagents and conditions: (a) NH₄SCN, H₂O, reflux, 4 h; (b) Br₂, CHCl₃, 1 h at 0° C., reflux, 2 h (c) KOH (d) Gl. acetic acid (e) Carbonyl 1, 1′ diimidazole, THF, reflux, 3 h; (f) 1, 4 dibromoalkane, K₂CO₃, DMF, 60° C., 3 h; (g) cyclohexyl piperazine, K₂CO₃, TBAI, ACN, reflux, 6 h σ Receptor Assays Compounds were evaluated for σ-1 and σ-2 binding in rat brain homogenates. Twelve concentrations of each test ligand (0.001-1,000 nM) were incubated for 120 min at 25° C. in 50 mM Tris-HCl, pH 8.0 with 500 μg membrane protein, and 5 nM [$^3$H](+)-pentazocine (for $\sigma_1$ assays) or 3 nM [$^3$H]DTG plus 300 nM (+)-pentazocine (for $\sigma_2$ assays); non-specific binding was determined in the presence of 10 μM haloperidol. The assays were terminated with ice-cold 10 mM Tris-HCl, pH 8.0, followed by two washes through glass fiber filters that were pre-soaked for at least 30 min in 0.5% polyethyleneimine.

Non-σ Assays

Compounds were tested at various non-σ target sites to evaluate selectivity because cocaine interacts with these sites (dopamine, serotonin and norepinephrine transporters) or historic "sigma" ligands interact with them (opioid, NMDA, dopamine $D_2$, 5-HT$_2$ receptors). The compounds were tested in competition binding assays using rat brain homogenates as previously published. Briefly, the radioligands to label the sites of interest and compounds to define non-specific binding were as follows: dopamine transporters (0.5 nM [$^3$H]WIN35, 428, 50 μM cocaine), serotonin transporters (0.2 nM [$^3$H] paroxetine, 1.5 μM imipramine), norepinephrine transporters (0.5 nM [$^3$H]nisoxetine, 4 μM desipramine), opioid receptors (2 nM [$^3$H]bremazocine, 10 μM levollorphan), NMDA receptors (5 nM [$^3$H]TCP, 10 μM cyclazocine), dopamine $D_2$ receptors (5 nM [$^3$H](−)-sulpiride, 1 μM haloperidol), and 5-HT$_2$ receptors (2 nM [$^3$H]ketanserin, 1 μM mianserin). The results were reported as K, in nM. If after three independent replications of the assay, the 10,000 nM concentration of the compound did not display at least 30% inhibition of the radioligand, the affinity of the compound was reported as >10,000 nM.

Cocaine-Induced Convulsions

Male, Swiss Webster mice were pretreated (i.p.) with saline or compound (0.1-10 mg/kg), then challenged 15 min later with a convulsive dose of cocaine (70 mg/kg, i.p.). Mice were observed for the next 30 min for convulsions, which were defined as a loss of righting reflexes for at least 5 sec combined with the presence of clonic limb movements or popcorn jumping. Fisher's exact test was used to determine whether the effect produced by pretreatment with a particular drug dose differed significantly from pretreatment with the saline control.

Cocaine-Induced Locomotor Activity

Male, Swiss Webster mice were acclimated to the treatment room and then to the chambers of the automated activity monitoring system (San Diego Instruments, San Diego, Calif.). They were injected (i.p.) with saline or compound (0.1-20 mg/kg), then challenged 15 min later with cocaine (20 mg/kg, i.p.) or saline (i.p). The total locomotor activity (ambulatory, fine and rearing movements) of the mice was recorded for the next 30 min as the number of disruptions made by them in the 16×16 photobeam grid of their testing chamber.

Development of Sensitization

Male, Swiss Webster mice were acclimated as detailed above. For five consecutive days (Days 1-5), the mice were pretreated (i.p.) with saline or compound (0.1-20 mg/kg), then challenged 15 min later with cocaine (10 mg/kg, i.p.) or saline (i.p.). The total locomotor activity (ambulatory, fine and rearing movements) of the mice was recorded for the next 30 min as the number of disruptions made by them in the 16×16 photobeam grids of their testing chamber on each of the five days. A 10 day drug-free period followed. On Day 15, all of the mice were pre-administered (i.p.) saline followed by cocaine (10 mg/kg, i.p.), and locomotor activity quantified for the next 30 min.

Expression of Sensitization

Male, Swiss Webster mice were acclimated as detailed above. For five consecutive days (Days 1-5), the mice were pretreated (i.p) with saline, then challenged 15 min later with cocaine (10 mg/kg, i.p.). The total locomotor activity (ambulatory, fine and rearing movements) of the mice was recorded for the next 30 min. A 10 day drug free period followed and on Day 15, the mice were administered saline (i.p.) or compound (0.1-20 mg/kg), followed 15 min later with cocaine (10 mg/kg, i.p.). Locomotor activity was then recorded for the next 30 min.

Methamphetamine-Induced Locomotor Activity

Male, Swiss Webster mice were acclimated as detailed above. They were injected (i.p.) with saline or compound (0.1-20 mg/kg), then challenged 15 min later with methamphetamine (1 mg/kg, i.p.) or saline (i.p). The total locomotor activity (ambulatory, fine and rearing movements) of the mice was recorded for the next 30 min as the number of disruptions made by them in the 16×16 photobeam grids surrouding their testing chambers.

Methamphetamine-Induced Dopamine Depletions

Male, Swiss Webster mice were injected (i.p.) with saline or compound (0-20 mg/kg), followed 15 min later with either saline (−METH) or methamphetamine (5 mg/kg) at 2 hr intervals, a total of four times. Striatal dopamine levels were measured one week later.

The following represents compounds which are within the scope of the invention and which were prepared and tested for activity. Also included are compounds which were prepared but not tested but which are expected to have activity similar to the prepared and tested compounds. Also included in the listing are compounds which can be prepared and which would be expected to have activities similar to those compounds which were prepared and tested.

| Compd. | Structure | Ki (nM) |
|---|---|---|
| SN-48 | 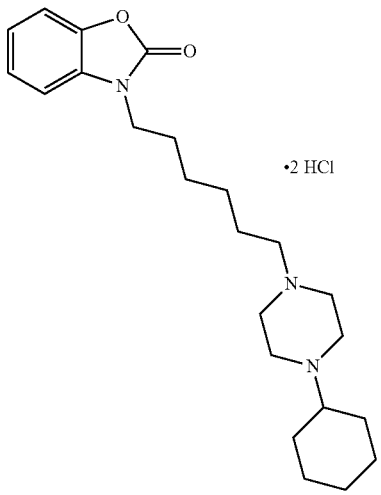 [SMILES: O=c1oc2ccccc2n1CCCCCCN1CCN(C2CCCCC2)CC1] | $\sigma 1 = 4.60 \pm 1.08$<br>$\sigma 2 = 3.06 \pm 0.45$ |
| SN-55 | 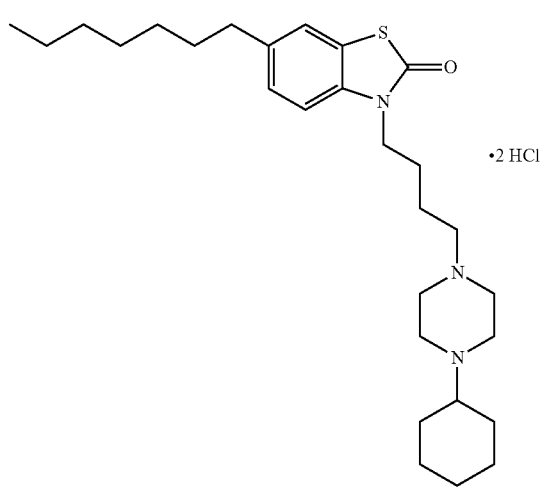 [SMILES: CCCCCCCc1ccc2c(c1)sc(=O)n2CCCCN1CCN(C2CCCCC2)CC1] | $\sigma 1 = 34.12 \pm 8.09$<br>$\sigma 2 = 31.39 \pm 6.87$ |

-continued
| Compd. | Structure | Ki (nM) |
|---|---|---|
| SN-57 | 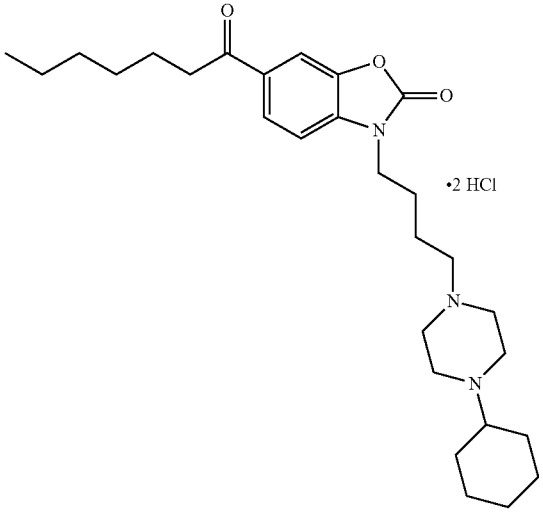 [SMILES: CCCCCCC(=O)c1ccc2c(c1)oc(=O)n2CCCCN1CCN(C2CCCCC2)CC1] •2 HCl | σ1 = 43.76 ± 6.12<br>σ2 = 29.29 ± 2.83 |
| SN-60 | 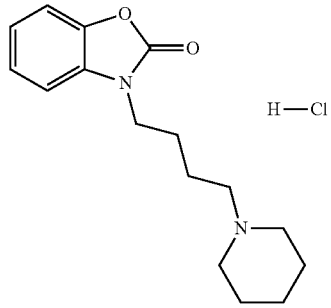 [SMILES: O=c1oc2ccccc2n1CCCCN1CCCCC1 ; Cl] H—Cl | σ1 = 12.06 ± 1.54<br>σ2 = 212.67 ± 11.81 |
| SN-61 | 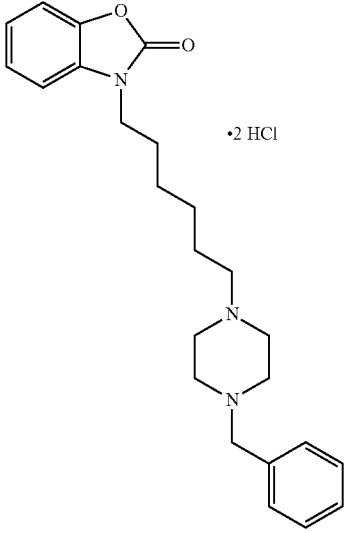 [SMILES: O=c1oc2ccccc2n1CCCCCCN1CCN(Cc2ccccc2)CC1] •2 HCl | σ1 = 4.68 ± 1.37<br>σ2 = 107.1 ± 32.59 |

-continued

| Compd. | Structure | Ki (nM) |
|---|---|---|
| SN-71 | 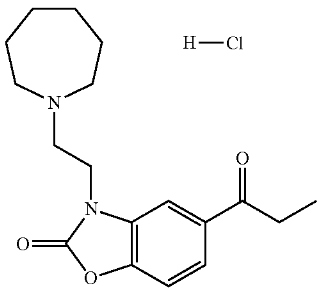 [SMILES: CCC(=O)c1ccc2oc(=O)n(CCN3CCCCCC3)c2c1 ; Cl] | σ1 = 114.74 ± 25.91<br>σ2 = 2342 ± 229.80 |
| SN-72 | 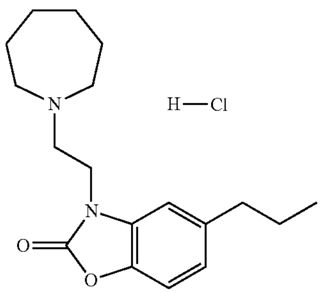 [SMILES: CCCc1ccc2oc(=O)n(CCN3CCCCCC3)c2c1 ; Cl] | σ1 = 3.33 ± 0.41<br>σ2 = 1810.66 ± 83.76 |
| SN-78 | 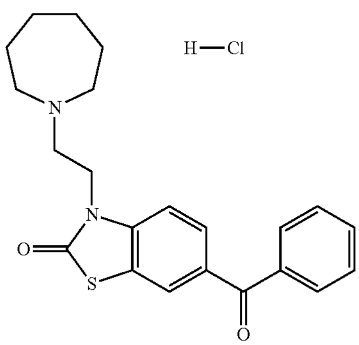 [SMILES: O=C(c1ccccc1)c1ccc2c(c1)sc(=O)n2CCN1CCCCCC1 ; Cl] | σ1 = 88.31 ± 8.59<br>σ2 = 859.66 ± 86.59 |
| SN-79 | 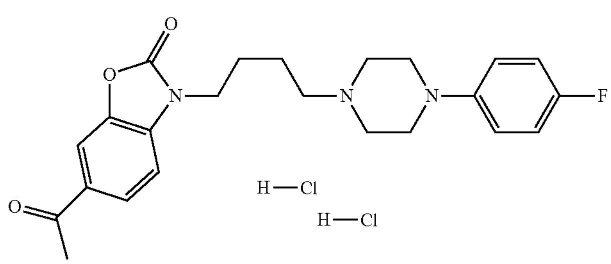 | σ1 = >100,000<br>σ2 = 6.06 ± 0.74 |
| SN-81 | 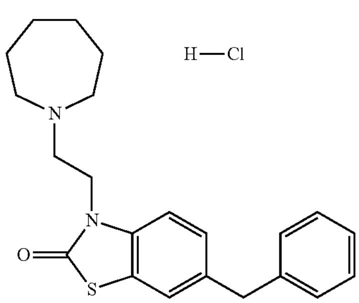 [SMILES: O=c1sc2cc(Cc3ccccc3)ccc2n1CCN1CCCCCC1 ; Cl] | σ1 = 7.42 ± 3.21<br>σ2 = 224.56 ± 46.88 |

-continued
| Compd. | Structure | Ki (nM) |
|---|---|---|
| SN-97 | 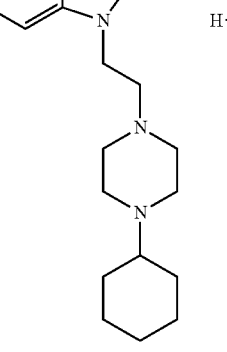 | σ1 = 4.66 ± 0.74<br>σ2 = 2.25 ± 0.37 |
| SN-98 | 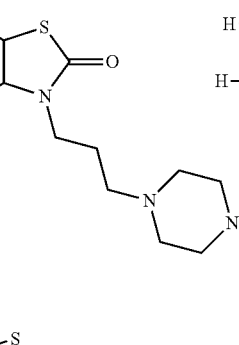 | σ1 = 5.61 ± 0.74<br>σ2 = 3.05 ± 0.41 |
| SN-99 | 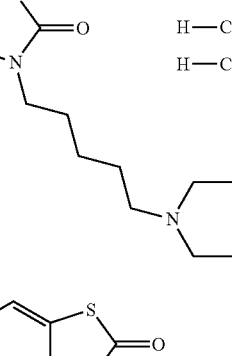 | σ1 = 4.98 ± 0.42<br>σ2 = 2.44 ± 0.26 |
| SN-102 | 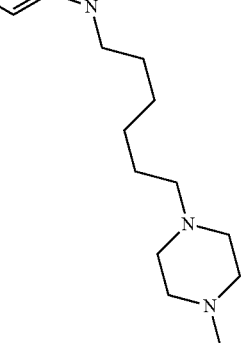 | σ1 = 6.55 ± 0.25<br>σ2 = 1.49 ± 0.18 |

-continued
| Compd. | Structure | Ki (nM) |
|---|---|---|
| SN-123 | 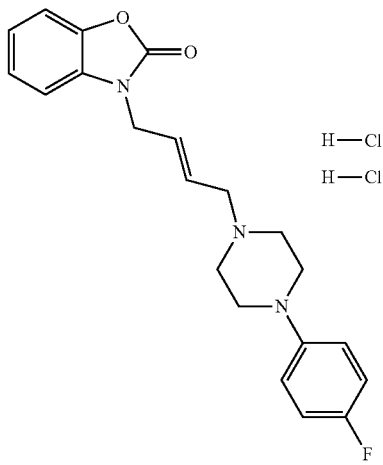 | |
| SN-124 | 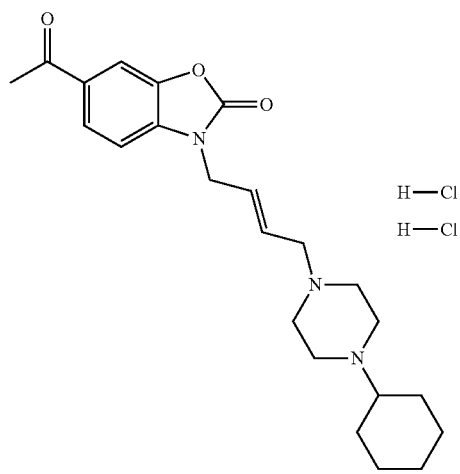 | |
| SN-125 | 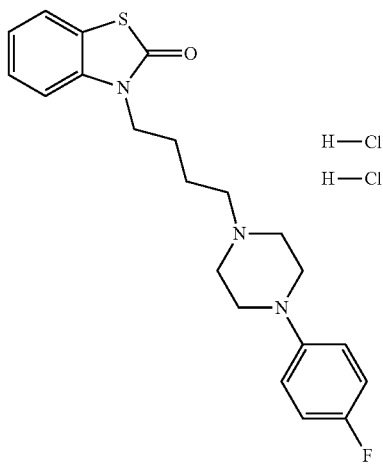 | |

-continued

| Compd. | Structure | Ki (nM) |
|---|---|---|
| SN-126 | 6-acetyl-3-[(2E)-4-[4-(4-fluorophenyl)piperazin-1-yl]but-2-en-1-yl]-1,3-benzoxazol-2(3H)-one · 2HCl | |
| SN-127 | 6-acetyl-3-{3-[4-(4-fluorophenyl)piperazin-1-yl]propyl}-1,3-benzoxazol-2(3H)-one · 2HCl | |
| SN-136 | 6-acetyl-3-{5-[4-(4-fluorophenyl)piperazin-1-yl]pentyl}-1,3-benzoxazol-2(3H)-one · 2HCl | |
| SN-137 | 6-acetyl-3-{4-[4-(4-fluorophenyl)piperazin-1-yl]butyl}-1,3-benzothiazol-2(3H)-one · 2HCl | |

| Compd. | Structure | Ki (nM) |
|---|---|---|
| SN-138 | 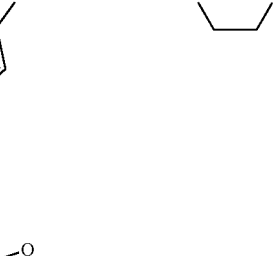 | |
| SN-139 | 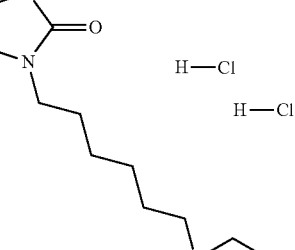 | |
| SN-140 | 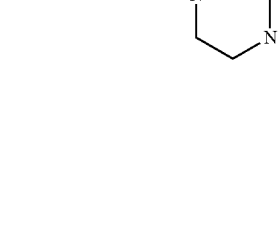 | |
| SN-147 | 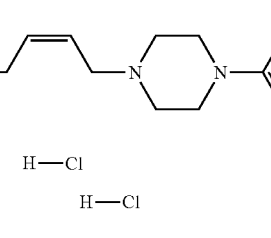 | |

-continued

| Compd. | Structure | Ki (nM) |
|---|---|---|
| SN-148 | 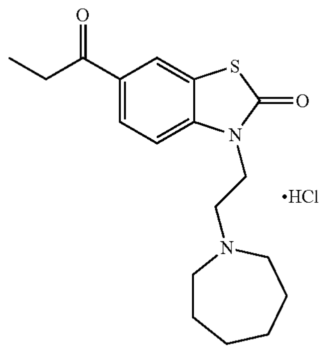 [SMILES: CCC(=O)c1ccc2c(c1)sc(=O)n2CCN1CCCCCC1 ; Cl] | |
| SN-150 | 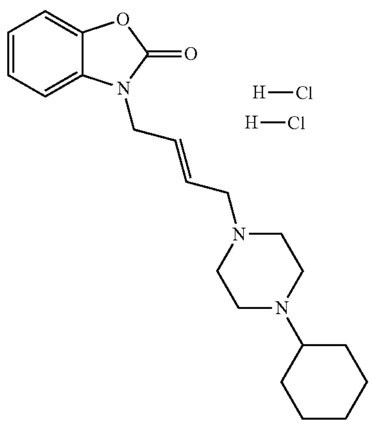 | |
| SN-158 | 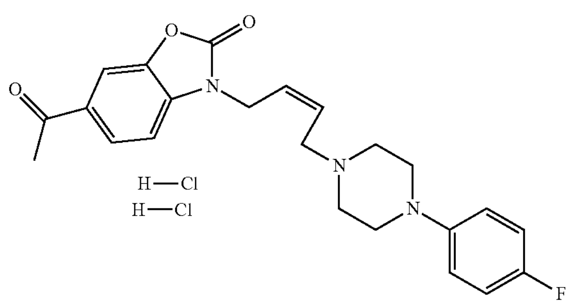 | |
| SN-167 | 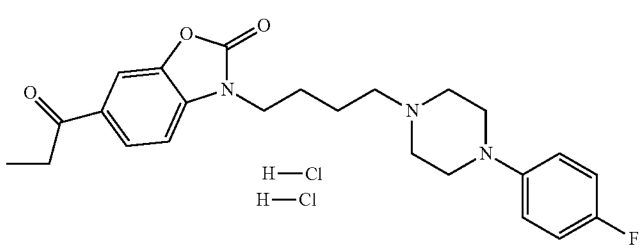 | |
| SN-168 | 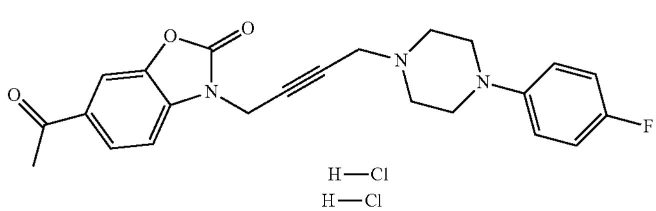 | |

| Compd. | Structure | Ki (nM) |
|---|---|---|
| SN-169 | 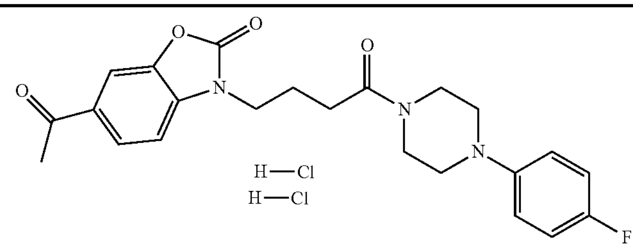 | |
| SN-170 | 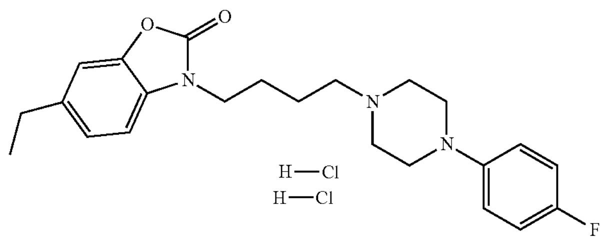 | |
| SN-196 | 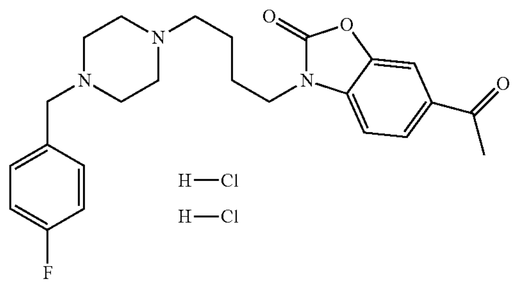 | |
| SN-197 | 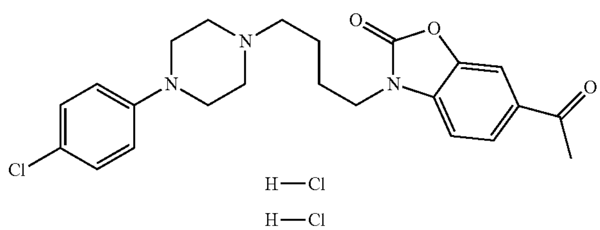 | |
| SN-198 | 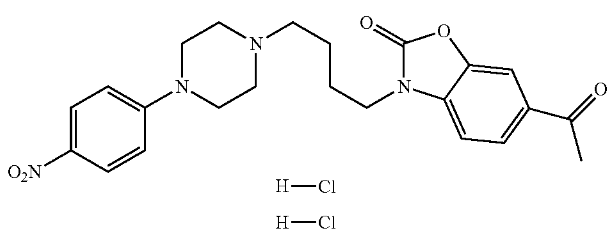 | |
| SN-199 | 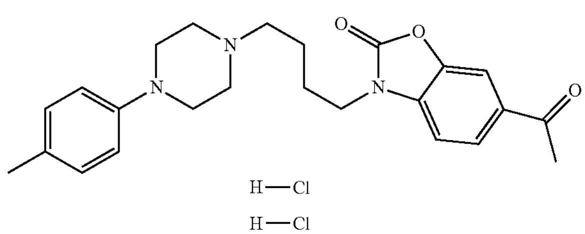 | |

-continued
| Compd. | Structure | Ki (nM) |
|---|---|---|
| SN-203 | 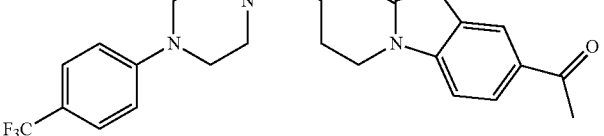 H—Cl H—Cl | |
| SN-204 | 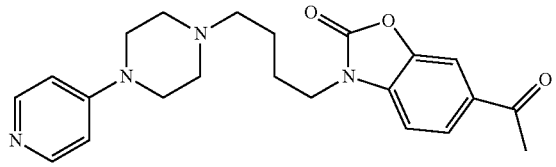 H—Cl H—Cl | |
| SN-205 | 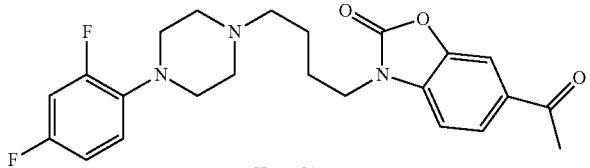 H—Cl H—Cl | |
| SN-212 | 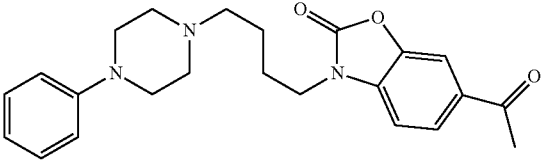 H—Cl H—Cl | |
| SN-213 | 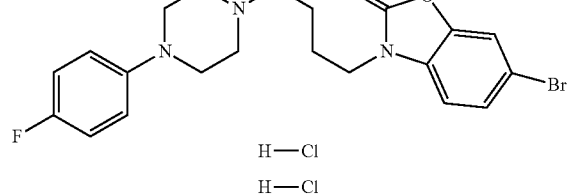 H—Cl H—Cl | |
| SN-214 | 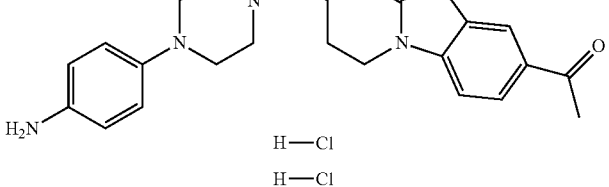 H—Cl H—Cl | |

| Compd. | Structure | Ki (nM) |
|---|---|---|
| SN-230 | | |
| SN-231 | | |
| SN-232 | | |
| CMPD | STRUCTURE | Ki (nM) σ₁ | Ki (nM) σ₂ |
|---|---|---|---|
| CM121 | | 11.26 ± 1.25 | 1.83 ± 0.17 |
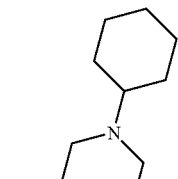

-continued
| CMPD | STRUCTURE | Ki (nM) $\sigma_1$ | Ki (nM) $\sigma_2$ |
|------|-----------|--------------------|--------------------|
| CM124 | 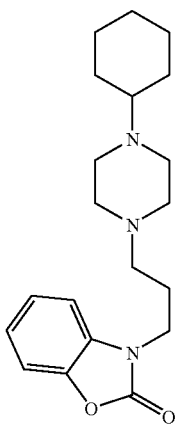 [SMILES: O=c1oc2ccccc2n1CCCN1CCN(C2CCCCC2)CC1] | 5.22 ± 1.11 | 8.74 ± 2.30 |
| CM126 | 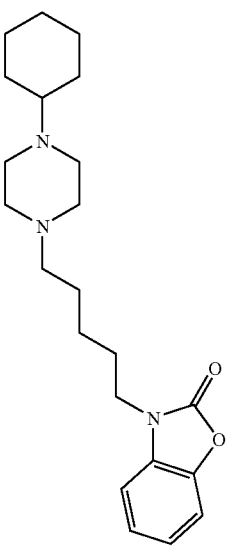 [SMILES: O=c1oc2ccccc2n1CCCCCN1CCN(C2CCCCC2)CC1] | 10.55 ± 2.52 | 5.89 ± 1.31 |
| CM129 | 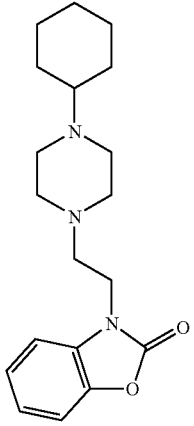 [SMILES: O=c1oc2ccccc2n1CCN1CCN(C2CCCCC2)CC1] | 6.90 ± 0.37 | 5.43 ± 0.78 |

| CMPD | STRUCTURE | Ki (nM) $\sigma_1$ | Ki (nM) $\sigma_2$ |
|---|---|---|---|
| CM135 | 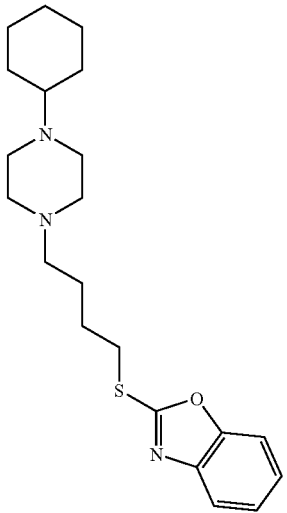 [SMILES: c1ccc2oc(SCCCCN3CCN(C4CCCCC4)CC3)nc2c1] | 3.37 ± 0.28 | 3.77 ± 0.35 |
| CM138 | 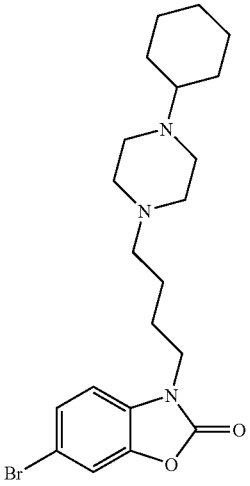 [SMILES: O=c1oc2cc(Br)ccc2n1CCCCN1CCN(C2CCCCC2)CC1] | 7.87 ± 0.19 | 4.47 ± 0.42 |
| CM142 | 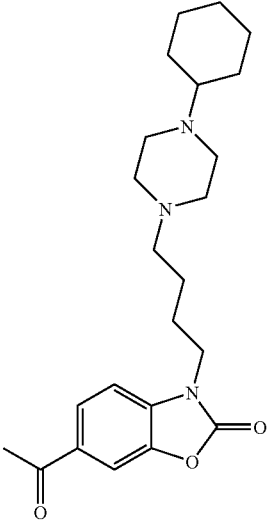 [SMILES: CC(=O)c1ccc2c(c1)oc(=O)n2CCCCN1CCN(C2CCCCC2)CC1] | 46.4 ± 8.06 | 7.04 ± 0.79 |

-continued
| CMPD | STRUCTURE | Ki (nM) $\sigma_1$ | Ki (nM) $\sigma_2$ |
|---|---|---|---|
| CM145 | 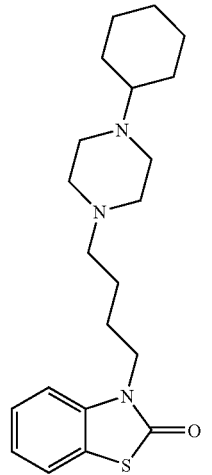 | 4.17 ± 0.62 | 0.39 ± 0.06 |
| CM146 | 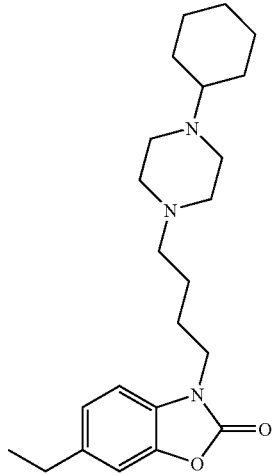 [SMILES: CCc1ccc2c(c1)oc(=O)n2CCCCN1CCN(C2CCCCC2)CC1] | 2.18 ± 0.14 | 2.56 ± 1.22 |
| CM152 | 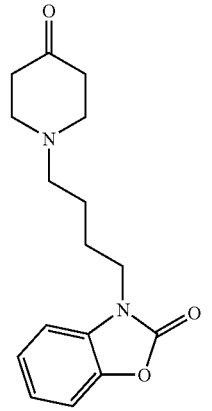 [SMILES: O=C1CCN(CCCCn2c(=O)oc3ccccc32)CC1] | 19.3 ± 0.90 | 78.5 ± 39.6 |

-continued
| CMPD | STRUCTURE | Ki (nM) $\sigma_1$ | Ki (nM) $\sigma_2$ |
|---|---|---|---|
| CM156 | 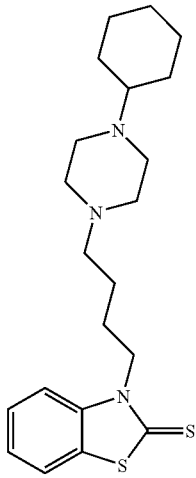 [SMILES: S=c1sc2ccccc2n1CCCCN1CCN(C2CCCCC2)CC1] | 1.28 ± 0.38 | 0.55 ± 0.08 |
| CM159 | 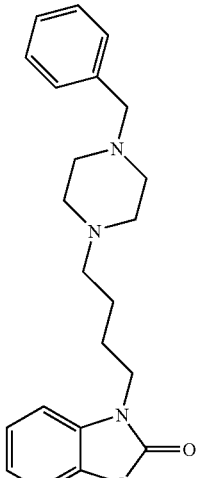 | 4.44 ± 0.88 | 46.41 ± 12.61 |
| CM160 | 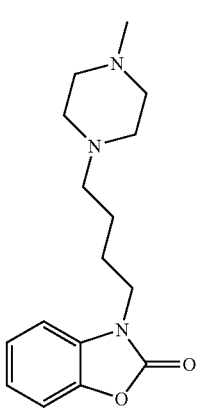 [SMILES: CN1CCN(CCCCn2c(=O)oc3ccccc32)CC1] | 91.69 ± 11.52 | 2382.33 ± 142.94 |

-continued
| CMPD | STRUCTURE | Ki (nM) $\sigma_1$ | Ki (nM) $\sigma_2$ |
| --- | --- | --- | --- |
| CM162 | 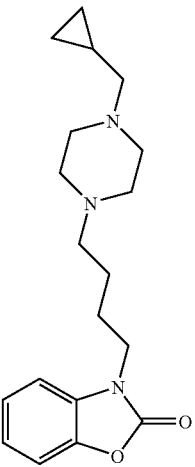 [SMILES: O=c1oc2ccccc2n1CCCCN1CCN(CC2CC2)CC1] | 10.83 ± 1.00 | 46.75 ± 10.18 |
| CM165 | 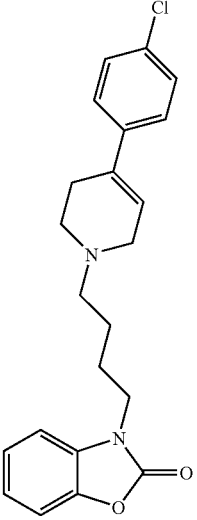 | 2.40 ± 0.38 | 14.44 ± 3.09 |
| CM166 | 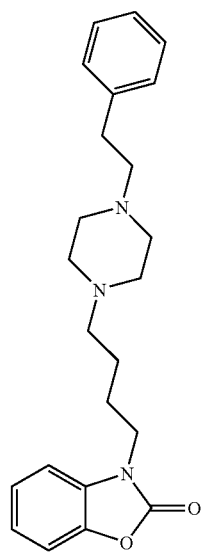 [SMILES: O=c1oc2ccccc2n1CCCCN1CCN(CCc2ccccc2)CC1] | 3.15 ± 0.37 | 92.71 ± 14.14 |

-continued
| CMPD | STRUCTURE | Ki (nM) $\sigma_1$ | Ki (nM) $\sigma_2$ |
|---|---|---|---|
| CM167 | 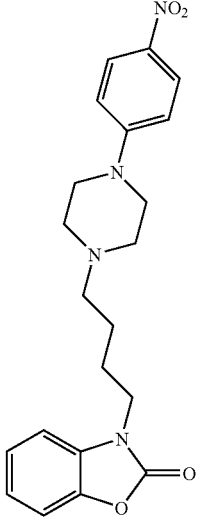 [SMILES: O=c1oc2ccccc2n1CCCCN1CCN(c2ccc([N+](=O)[O-])cc2)CC1] | 259.07 ± 33.45 | 226.00 ± 17.50 |
| CM168 | 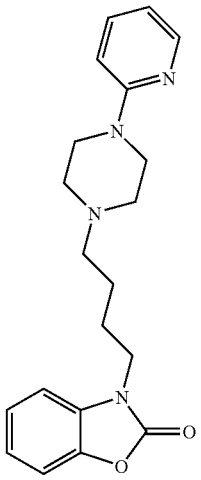 [SMILES: O=c1oc2ccccc2n1CCCCN1CCN(c2ccccn2)CC1] | 311.93 ± 33.22 | 128.10 ± 16.26 |
| CM169 | 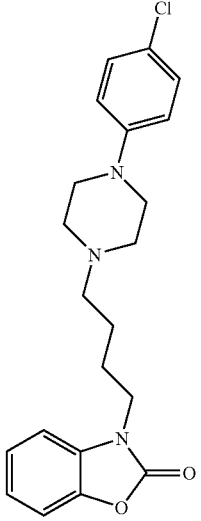 | 25.44 ± 4.72 | 241.5 ± 28.98 |

| CMPD | STRUCTURE | Ki (nM) $\sigma_1$ | Ki (nM) $\sigma_2$ |
|---|---|---|---|
| CM170 | 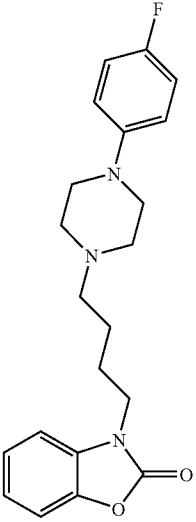 | 7.59 ± 0.08 | 0.70 ± 0.11 |
| CM171 | 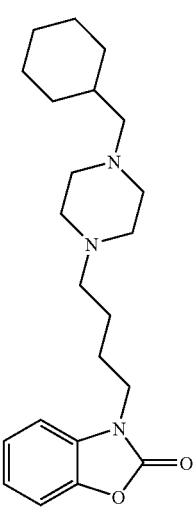 [SMILES: O=c1oc2ccccc2n1CCCCN1CCN(CC2CCCCC2)CC1] | 0.94 ± 0.13 | 13.94 ± 2.86 |
| CM172 | 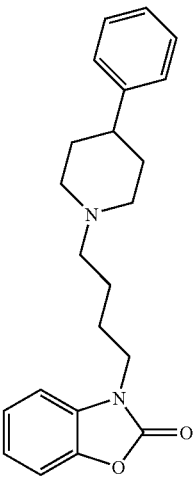 [SMILES: O=c1oc2ccccc2n1CCCCN1CCC(c2ccccc2)CC1] | 0.58 ± 0.22 | 17.22 ± 1.04 |

-continued
| CMPD | STRUCTURE | Ki (nM) $\sigma_1$ | Ki (nM) $\sigma_2$ |
|---|---|---|---|
| CM174 | 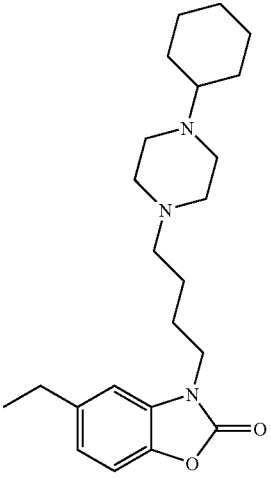 [SMILES: CCc1ccc2oc(=O)n(CCCCN3CCN(C4CCCCC4)CC3)c2c1] | 4.04 ± 0.35 | 58.24 ± 11.48 |
| CM175 | 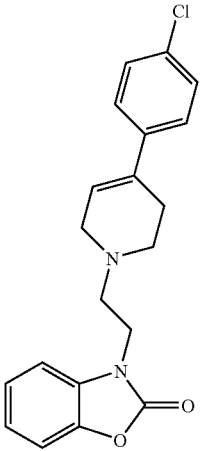 | 21.37 ± 3.68 | 616.33 ± 77.47 |
| CM176 | 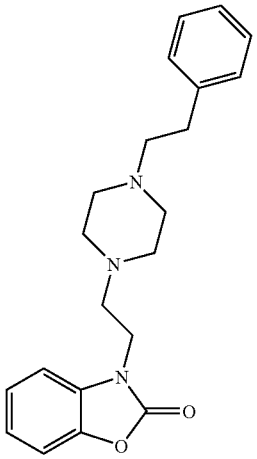 [SMILES: O=c1oc2ccccc2n1CCN1CCN(CCc2ccccc2)CC1] | 1.43 ± 0.26 | 21.73 ± 2.79 |

-continued

| CMPD | STRUCTURE | Ki (nM) $\sigma_1$ | Ki (nM) $\sigma_2$ |
|---|---|---|---|
| CM178 | 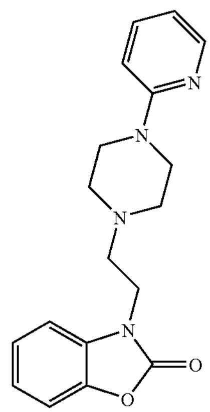 [SMILES: O=c1oc2ccccc2n1CCN1CCN(c2ccccn2)CC1] | >10,000 | >10,000 |
| CM179 | 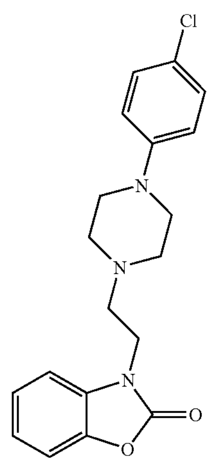 [SMILES: O=c1oc2ccccc2n1CCN1CCN(c2ccc(Cl)cc2)CC1] | 1426.33 ± 185.09 | 2260 ± 96.08 |
| CM181 | 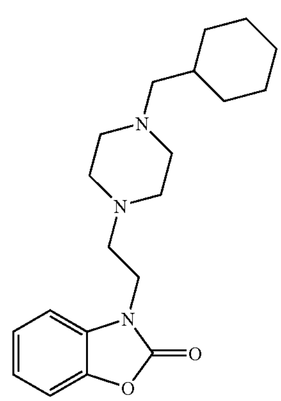 [SMILES: O=c1oc2ccccc2n1CCN1CCN(CC2CCCCC2)CC1] | 2.36 ± 0.38 | 8.83 ± 1.17 |

-continued
| CMPD | STRUCTURE | Ki (nM) σ$_1$ | Ki (nM) σ$_2$ |
|---|---|---|---|
| CM182 | 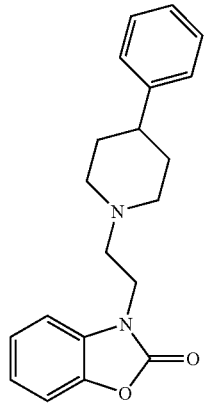 [SMILES: O=c1oc2ccccc2n1CCN1CCC(c2ccccc2)CC1] | 14.08 ± 2.84 | 777.26 ± 72.47 |
| CM184 | 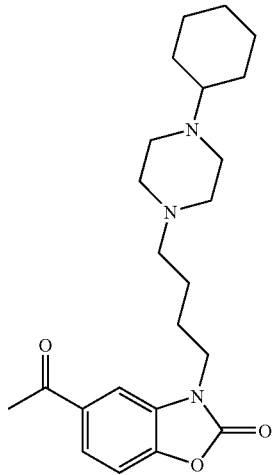 [SMILES: CC(=O)c1ccc2oc(=O)n(CCCCN3CCN(C4CCCCC4)CC3)c2c1] | 40.82 ± 6.21 | 10.41 ± 1.54 |
| CM188 | 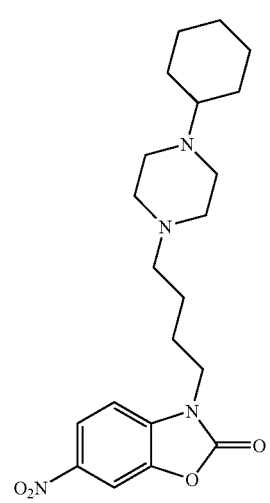 [SMILES: O=c1oc2cc([N+](=O)[O-])ccc2n1CCCCN1CCN(C2CCCCC2)CC1] | 11.11 ± 1.61 | 2.46 ± 0.18 |

-continued
| CMPD | STRUCTURE | Ki (nM) $\sigma_1$ | Ki (nM) $\sigma_2$ |
|---|---|---|---|
| CM191 | 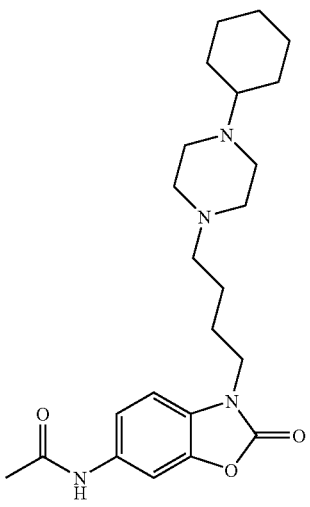 [SMILES: CC(=O)Nc1ccc2c(c1)oc(=O)n2CCCCN1CCN(C2CCCCC2)CC1] | 213.87 ± 55.33 | 77.37 ± 14.22 |
| CM295 | 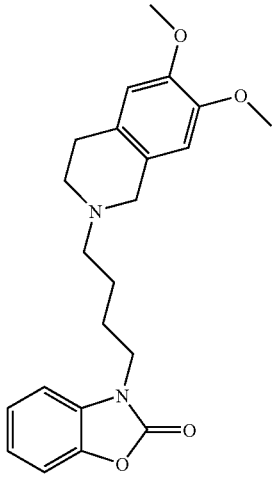 [SMILES: COc1cc2c(cc1OC)CN(CCCCn1c(=O)oc3ccccc31)CC2] | 74.31 ± 3.77 | 1.52 ± 0.64 |
| CM307 | 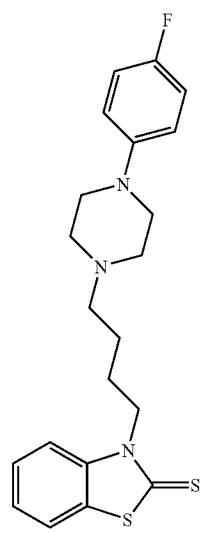 [SMILES: Fc1ccc(N2CCN(CCCCn3c(=S)sc4ccccc43)CC2)cc1] | 6.27 ± 0.78 | 6.61 ± 1.42 |

-continued

| CMPD | STRUCTURE | Ki (nM) σ$_1$ | Ki (nM) σ$_2$ |
|---|---|---|---|
| CM308 | 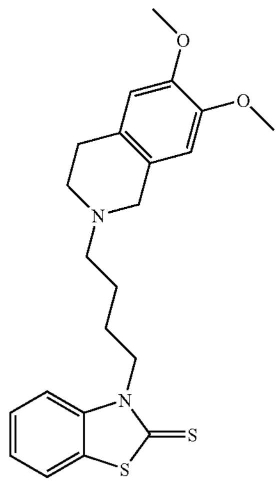 [SMILES: COc1cc2c(cc1OC)CN(CCCCn1c(=S)sc3ccccc31)CC2] | 9.11 ± 1.31 | 0.56 ± 0.12 |
| CM322 | 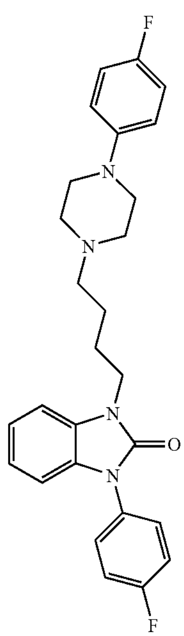 [SMILES: O=c1n(CCCCN2CCN(c3ccc(F)cc3)CC2)c2ccccc2n1-c1ccc(F)cc1] | 118.46 ± 48.37 | 1.67 ± 0.16 |

| CMPD | STRUCTURE | Ki (nM) σ$_1$ | Ki (nM) σ$_2$ |
|---|---|---|---|
| CM325 | 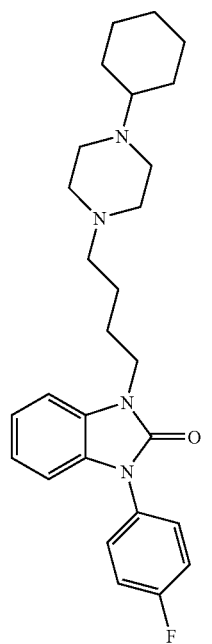 [SMILES: O=c1n(CCCCN2CCN(C3CCCCC3)CC2)c2ccccc2n1-c1ccc(F)cc1] | 5.04 ± 0.66 | 2.12 ± 0.75 |
| CM328 | 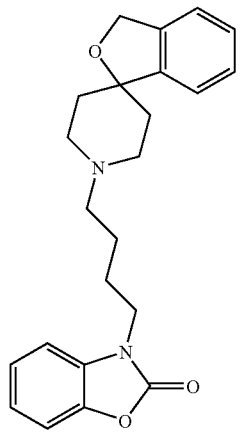 [SMILES: S=c1sc2ccccc2n1CCCCN1CCC2(CC1)OCc1ccccc12] | | |
| CM329 | 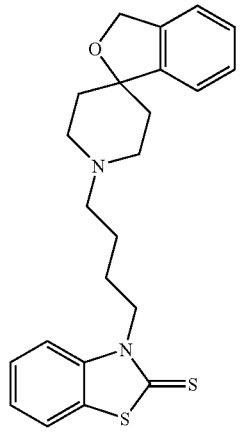 | | |

| CMPD | STRUCTURE | Ki (nM) σ$_1$ | Ki (nM) σ$_2$ |
|---|---|---|---|
| CM330 | 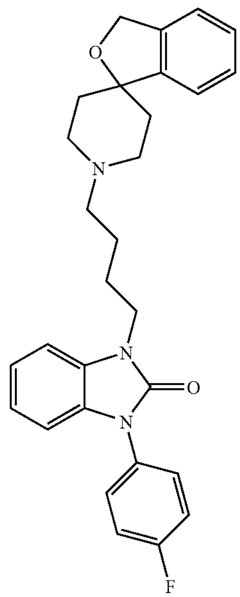 [SMILES: O=c1n(CCCCN2CCC3(CC2)OCc2ccccc23)c2ccccc2n1-c1ccc(F)cc1] | | |
| CM338 | 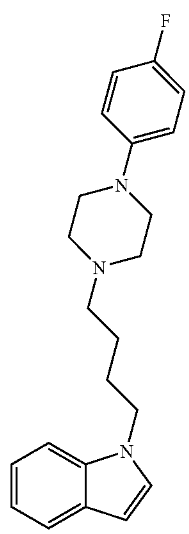 [SMILES: Fc1ccc(N2CCN(CCCCn3ccc4ccccc43)CC2)cc1] | 169.8 ± 5.68 | 1.09 ± 0.03 |
| CM339 | 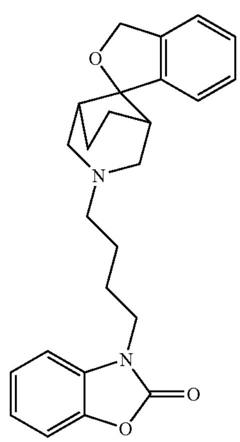 [SMILES: O=c1oc2ccccc2n1CCCCN1CC2CCC(C1)C21OCc2ccccc21] | | |

-continued
| CMPD | STRUCTURE | Ki (nM) σ₁ | Ki (nM) σ₂ |
|---|---|---|---|
| CM341 | 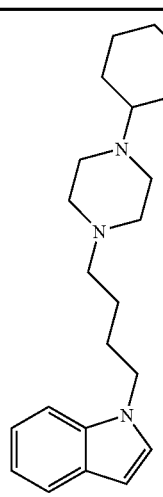 | 3.28 ± 0.32 | 1.90 ± 0.16 |
| CM343 | 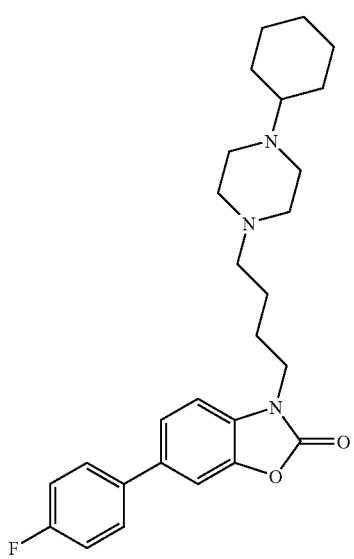 [SMILES: O=c1oc2cc(-c3ccc(F)cc3)ccc2n1CCCCN1CCN(C2CCCCC2)CC1] | 17.6 ± 0.82 | 38.13 ± 1.42 |
| CM347 | 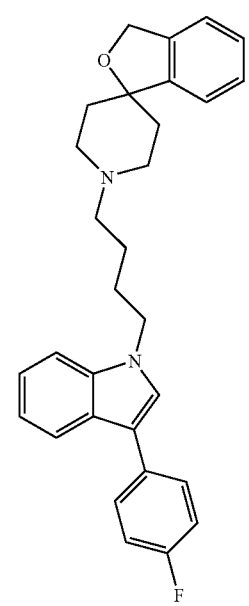 [SMILES: Fc1ccc(-c2cn(CCCCN3CCC4(CC3)OCc3ccccc34)c3ccccc23)cc1] | | |

-continued
| CMPD | STRUCTURE | Ki (nM) σ₁ | Ki (nM) σ₂ |
|---|---|---|---|
| CM349 | 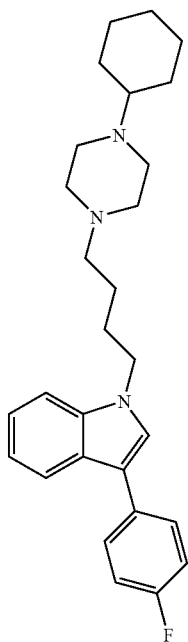 [SMILES: Fc1ccc(-c2cn(CCCCN3CCN(C4CCCCC4)CC3)c3ccccc23)cc1] | 90.87 ± 12.30 | 22.55 ± 1.13 |
| CM350 | 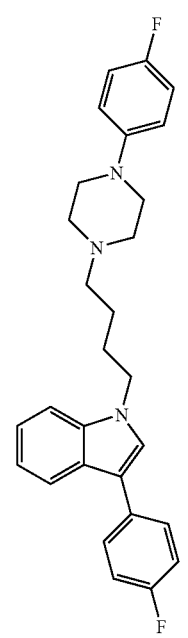 [SMILES: Fc1ccc(-c2cn(CCCCN3CCN(c4ccc(F)cc4)CC3)c3ccccc23)cc1] | 1202 ± 73.89 | 83.33 ± 3.96 |

| CMPD | STRUCTURE | Ki (nM) σ₁ | Ki (nM) σ₂ |
|---|---|---|---|
| CM353 | 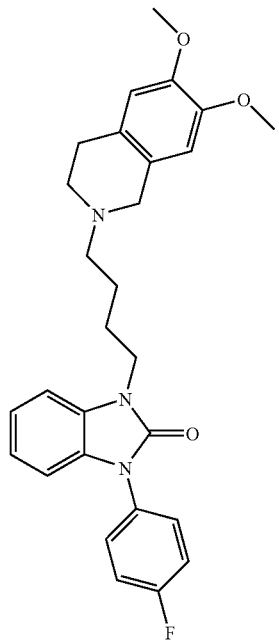 [SMILES: COc1cc2c(cc1OC)CN(CCCCn1c(=O)n(-c3ccc(F)cc3)c3ccccc31)CC2] | | |
| CM355 | 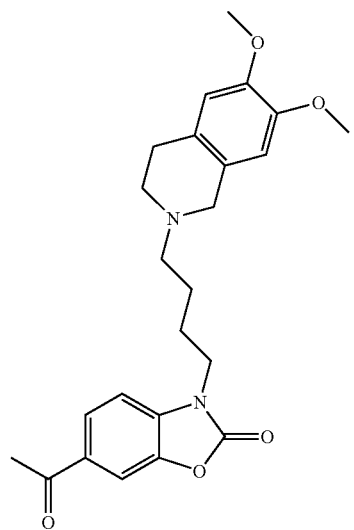 [SMILES: COc1cc2c(cc1OC)CN(CCCCn1c(=O)oc3cc(C(C)=O)ccc31)CC2] | | |

-continued
| CMPD | STRUCTURE | Ki (nM) σ₁ | Ki (nM) σ₂ |
|---|---|---|---|
| CM356 | 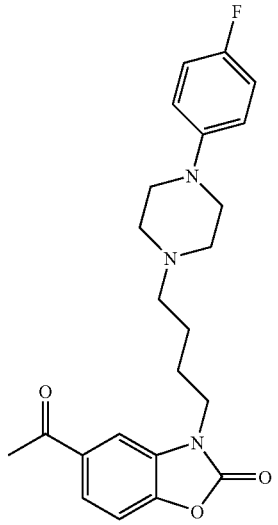 [SMILES: CC(=O)c1ccc2oc(=O)n(CCCCN3CCN(c4ccc(F)cc4)CC3)c2c1] | 27.82 ± 4.14 | 1.21 ± 0.20 |
| CM357 | 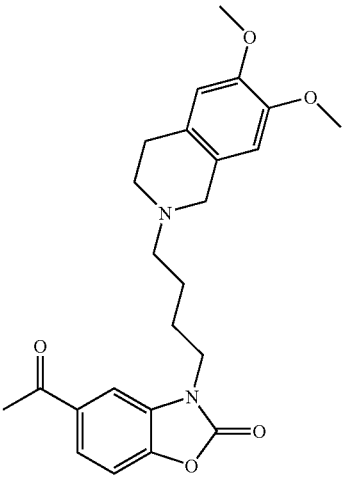 [SMILES: COc1cc2c(cc1OC)CN(CCCCn1c(=O)oc3ccc(C(C)=O)cc31)CC2] | | |
| CM360 | 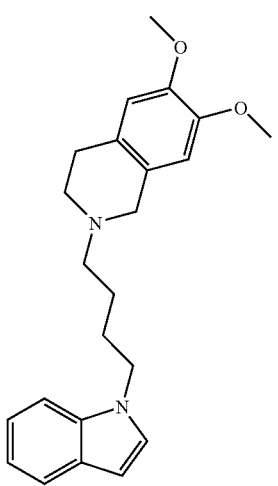 [SMILES: COc1cc2c(cc1OC)CN(CCCCn1ccc3ccccc31)CC2] | 73.25 ± 5.58 | 0.21 ± 0.020 |

-continued
| CMPD | STRUCTURE | Ki (nM) $\sigma_1$ | Ki (nM) $\sigma_2$ |
|---|---|---|---|
| CM361 | 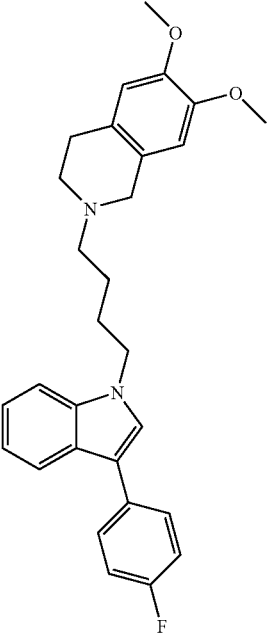 [SMILES: COc1cc2c(cc1OC)CN(CCCCn1cc(-c3ccc(F)cc3)c3ccccc31)CC2] | 4713 ± 449.50 | 4.37 ± 0.33 |
| CM362 | 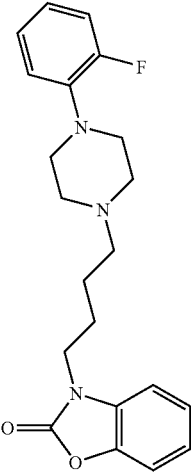 [SMILES: O=c1oc2ccccc2n1CCCCN1CCN(c2ccccc2F)CC1] | 17.64 ± 3.34 | 2.79 ± 0.49 |
| CM365 | 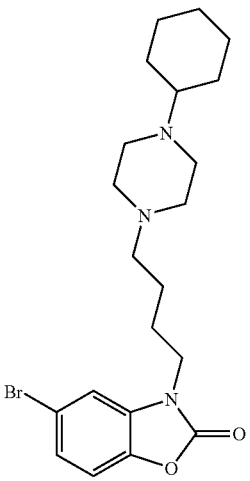 [SMILES: O=c1oc2ccc(Br)cc2n1CCCCN1CCN(C2CCCCC2)CC1] | 5.94 ± 0.35 | 0.055 ± 0.0063 |

-continued
| CMPD | STRUCTURE | Ki (nM) σ₁ | Ki (nM) σ₂ |
|---|---|---|---|
| CM366 | 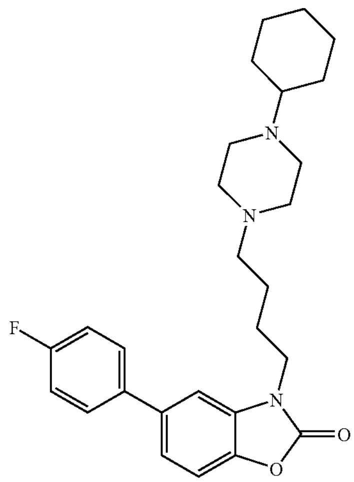 [SMILES: O=c1oc2ccc(-c3ccc(F)cc3)cc2n1CCCCN1CCN(C2CCCCC2)CC1] | 22.55 ± 1.14 | 0.0061 ± 0.00096 |
| CM372 | 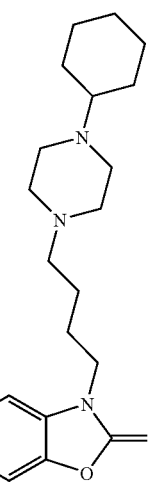 | 4.90 ± 1.70 | 0.77 ± 0.06 |
| CM373 | 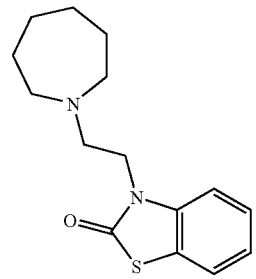 [SMILES: O=c1sc2ccccc2n1CCN1CCCCCC1] | | |
| CM393 | 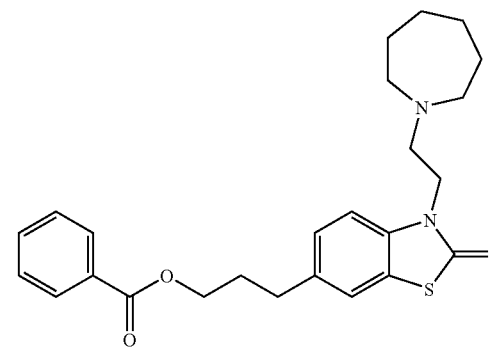 | | |

-continued
| CMPD | STRUCTURE | Ki (nM) $\sigma_1$ | Ki (nM) $\sigma_2$ |
|---|---|---|---|
| CM394 | 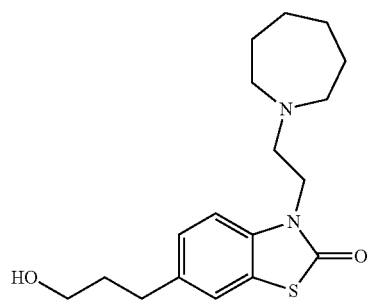 [SMILES: O=c1sc2cc(CCCO)ccc2n1CCN1CCCCCC1] | | |
| CM396 | 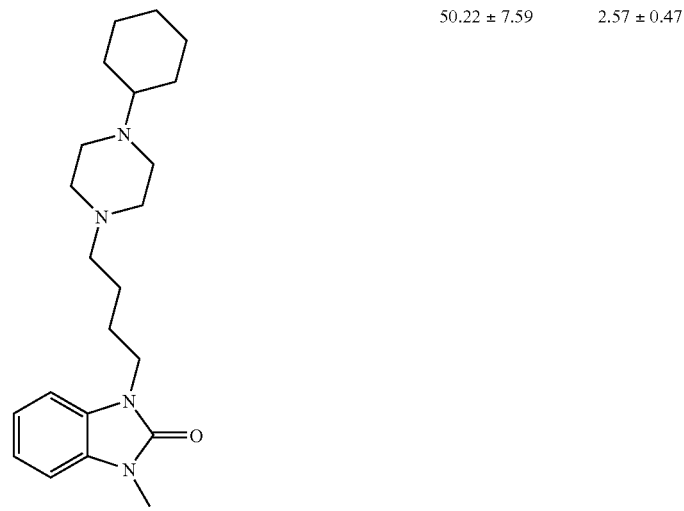 | 50.22 ± 7.59 | 2.57 ± 0.47 |
| CM397 | 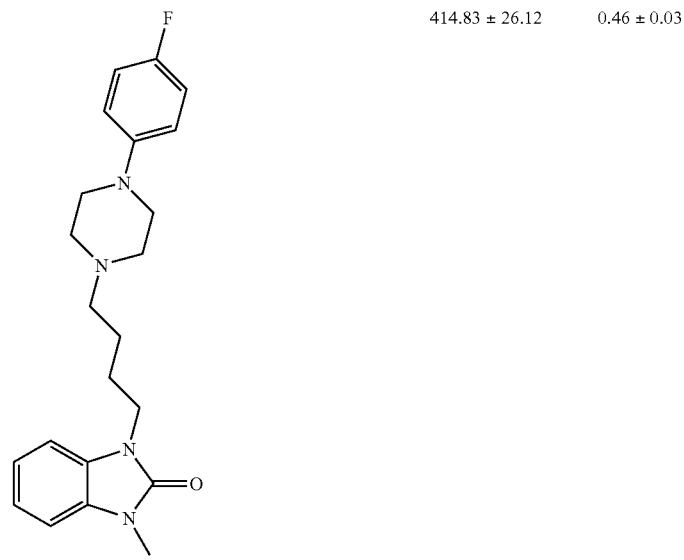 | 414.83 ± 26.12 | 0.46 ± 0.03 |

| CMPD | STRUCTURE | Ki (nM) $\sigma_1$ | Ki (nM) $\sigma_2$ |
|---|---|---|---|
| CM398 | 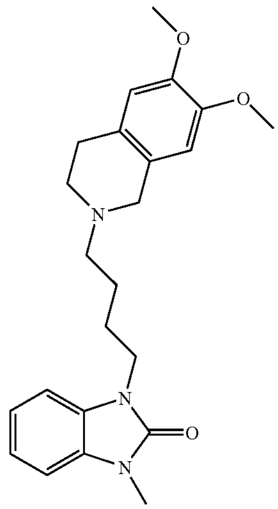 [SMILES: COc1cc2c(cc1OC)CN(CCCCn1c(=O)n(C)c3ccccc31)CC2] | | |
| CM401 | 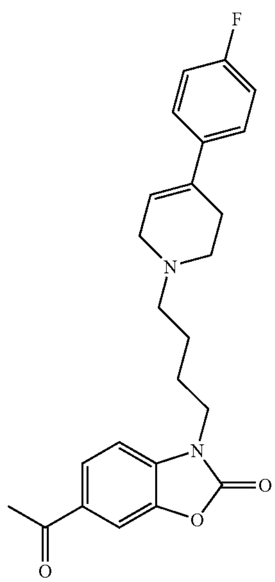 [SMILES: CC(=O)c1ccc2c(c1)oc(=O)n2CCCCN1CC=C(c2ccc(F)cc2)CC1] | 2.89 ± 0.23 | 0.66 ± 0.08 |
| CM406 | 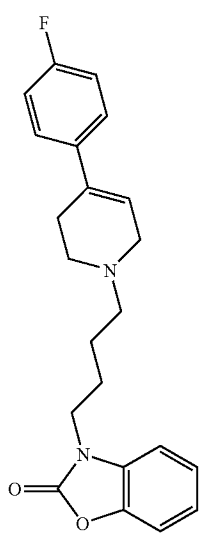 [SMILES: O=c1oc2ccccc2n1CCCCN1CC=C(c2ccc(F)cc2)CC1] | | |

-continued

| CMPD | STRUCTURE | Ki (nM) σ$_1$ | Ki (nM) σ$_2$ |
|---|---|---|---|
| CM407 | 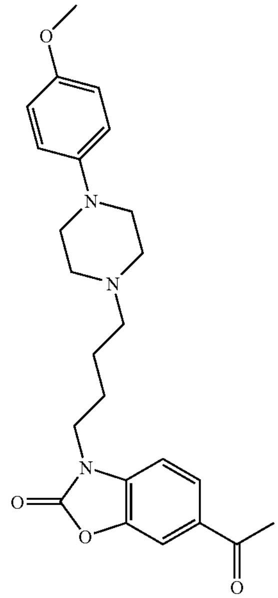 [SMILES: COc1ccc(N2CCN(CCCCn3c(=O)oc4cc(C(C)=O)ccc43)CC2)cc1] | | |
| CM408 | 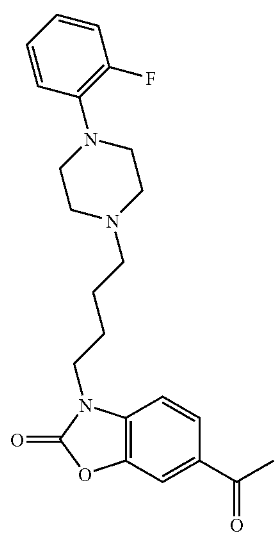 [SMILES: CC(=O)c1ccc2c(c1)oc(=O)n2CCCCN1CCN(c2ccccc2F)CC1] | | |
| CM418 | 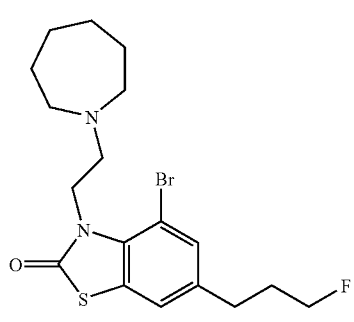 [SMILES: O=c1sc2cc(CCCF)cc(Br)c2n1CCN1CCCCCC1] | | |

| CMPD | STRUCTURE | Ki (nM) σ₁ | Ki (nM) σ₂ |
|---|---|---|---|
| CM422 | 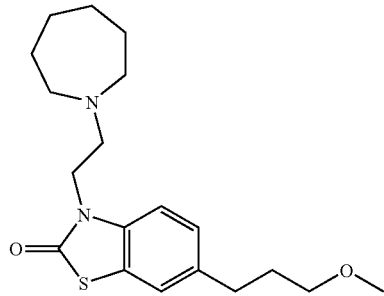 [SMILES: COCCCc1ccc2c(c1)sc(=O)n2CCN1CCCCCC1] | | |
| CM423 | 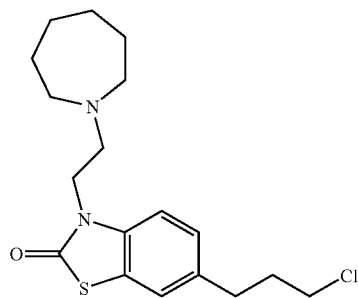 [SMILES: O=c1sc2cc(CCCCl)ccc2n1CCN1CCCCCC1] | | |
| CM433 | 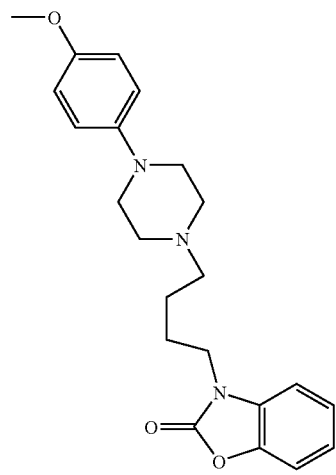 [SMILES: COc1ccc(N2CCN(CCCCn3c(=O)oc4ccccc43)CC2)cc1] | | |
| CM435 | 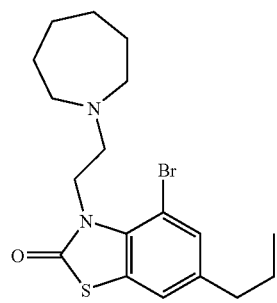 [SMILES: CCCc1cc(Br)c2c(c1)sc(=O)n2CCN1CCCCCC1] | | |

-continued
| CMPD | STRUCTURE | Ki (nM) $\sigma_1$ | Ki (nM) $\sigma_2$ |
|---|---|---|---|
| CM436 | 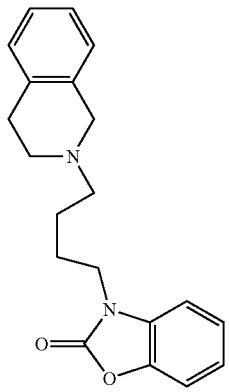 [SMILES: O=c1oc2ccccc2n1CCCCN1CCc2ccccc2C1] | | |
| CM442 | 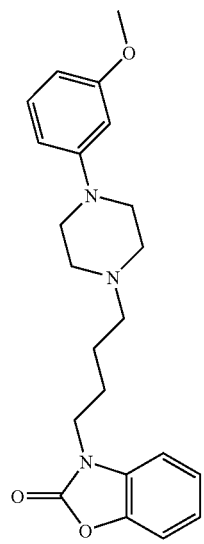 [SMILES: COc1cccc(N2CCN(CCCCn3c(=O)oc4ccccc43)CC2)c1] | | |
| CM444 | 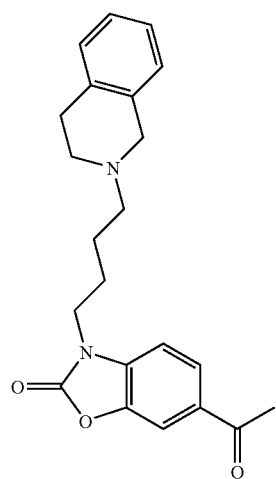 [SMILES: CC(=O)c1ccc2c(c1)oc(=O)n2CCCCN1CCc2ccccc2C1] | | |

-continued
| CMPD | STRUCTURE | Ki (nM) $\sigma_1$ | Ki (nM) $\sigma_2$ |
|---|---|---|---|
| CM449 | 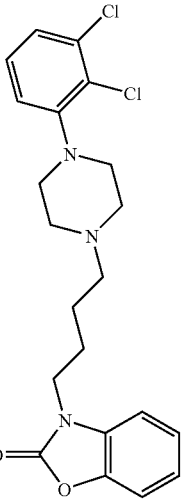 | | |
| CM450 | 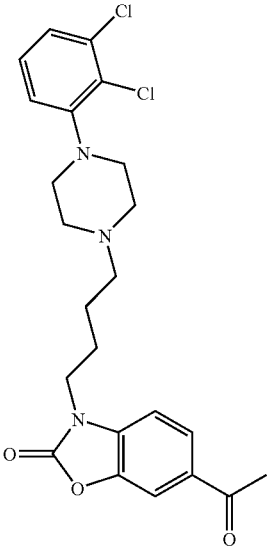 [SMILES: CC(=O)c1ccc2c(c1)oc(=O)n2CCCCN1CCN(c2cccc(Cl)c2Cl)CC1] | | |
| CM454 | 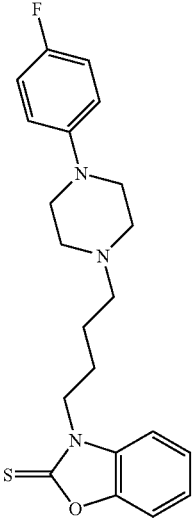 [SMILES: Fc1ccc(N2CCN(CCCCn3c(=S)oc4ccccc43)CC2)cc1] | | |

| CMPD | STRUCTURE | Ki (nM) σ$_1$ | Ki (nM) σ$_2$ |
|---|---|---|---|
| CM458 | 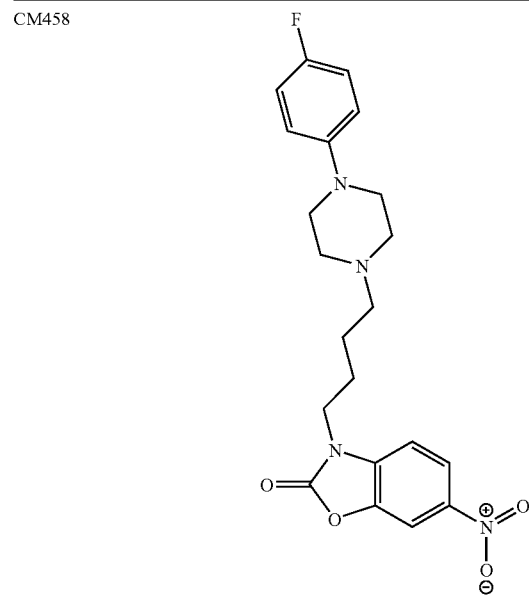 | | |
| CM459 | 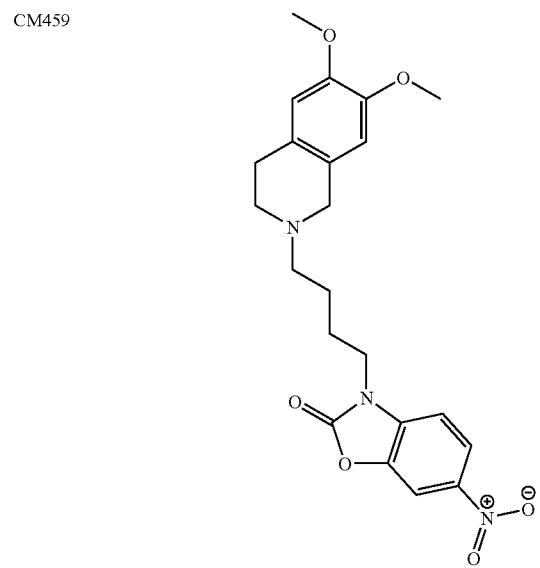 | | |

| CMPD | STRUCTURE | Ki (nM) σ₁ | Ki (nM) σ₂ |
|---|---|---|---|
| CM461 | 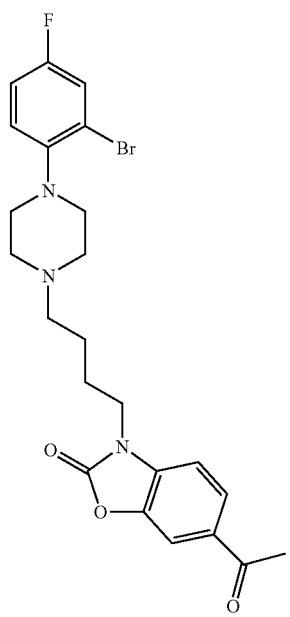 [SMILES: CC(=O)c1ccc2c(c1)oc(=O)n2CCCCN1CCN(c2ccc(F)cc2Br)CC1] | | |
| CM464 | 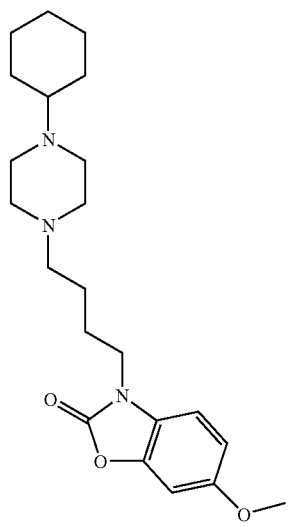 [SMILES: COc1ccc2c(c1)oc(=O)n2CCCCN1CCN(C2CCCCC2)CC1] | | |

-continued
| CMPD | STRUCTURE | Ki (nM) σ₁ | Ki (nM) σ₂ |
|---|---|---|---|
| CM465 | 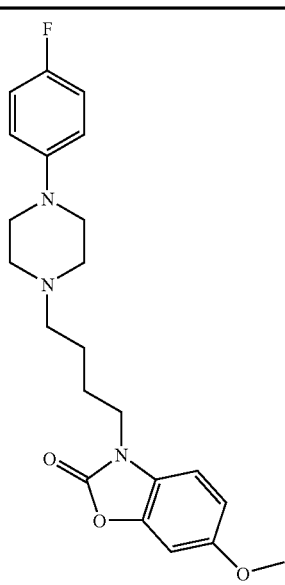 | | |
| CM466 | 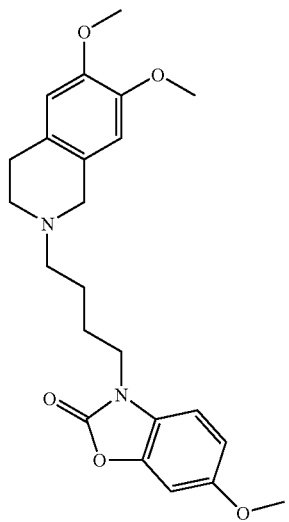 [SMILES: COc1ccc2c(c1)oc(=O)n2CCCCN1CCc2cc(OC)c(OC)cc2C1] | | |
| CM471 | 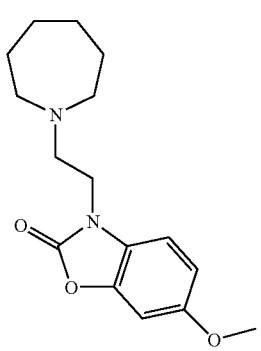 [SMILES: COc1ccc2c(c1)oc(=O)n2CCN1CCCCCC1] | | |

-continued
| CMPD | STRUCTURE | Ki (nM) σ₁ | Ki (nM) σ₂ |
|---|---|---|---|
| CM483 | 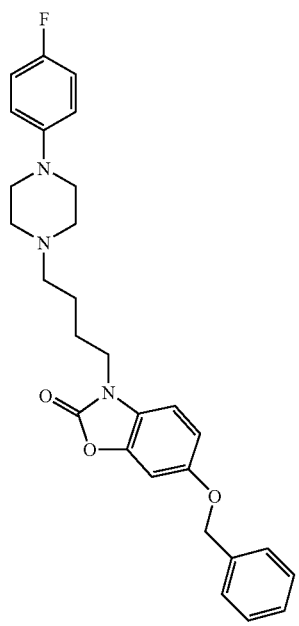 [SMILES: O=c1oc2cc(OCc3ccccc3)ccc2n1CCCCN1CCN(c2ccc(F)cc2)CC1] | | |
| CM484 | 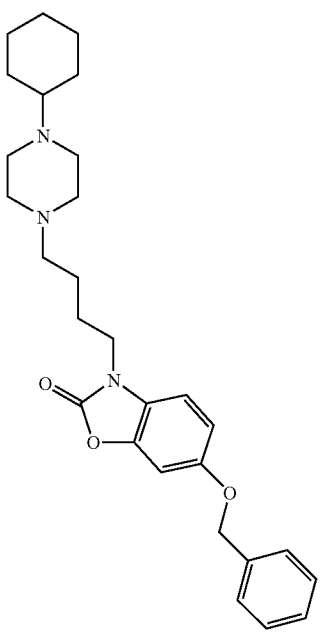 [SMILES: O=c1oc2cc(OCc3ccccc3)ccc2n1CCCCN1CCN(C2CCCCC2)CC1] | | |

| CMPD | STRUCTURE | Ki (nM) $\sigma_1$ | Ki (nM) $\sigma_2$ |
|---|---|---|---|
| CM485 | 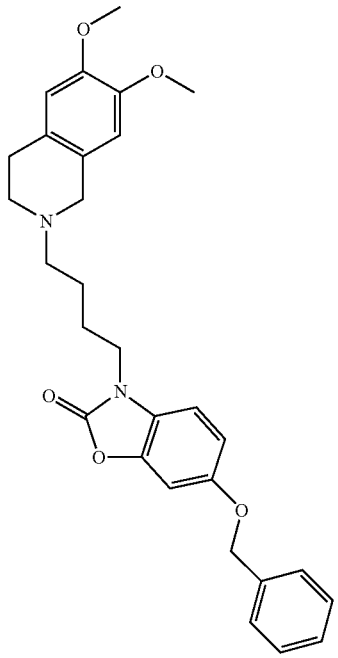 [SMILES: COc1cc2c(cc1OC)CN(CCCCn1c(=O)oc3cc(OCc4ccccc4)ccc31)CC2] | | |
| CM490 | 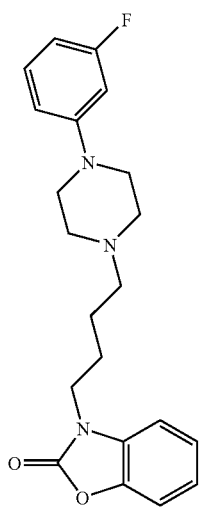 [SMILES: O=c1oc2ccccc2n1CCCCN1CCN(c2cccc(F)c2)CC1] | | |

-continued
| CMPD | STRUCTURE | Ki (nM) $\sigma_1$ | Ki (nM) $\sigma_2$ |
|---|---|---|---|
| CM491 | 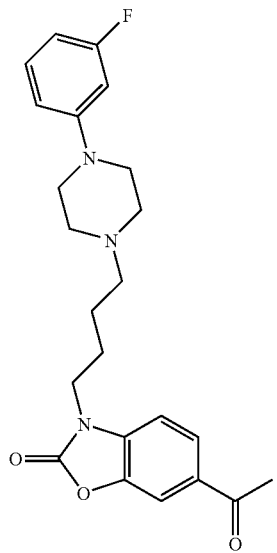 [SMILES: CC(=O)c1ccc2c(c1)oc(=O)n2CCCCN1CCN(c2cccc(F)c2)CC1] | | |
| CM498 | 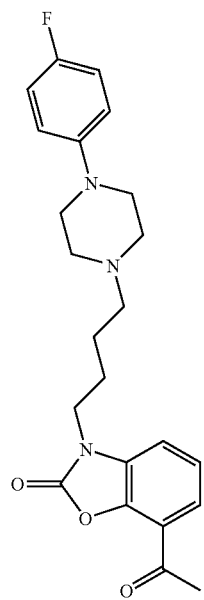 [SMILES: CC(=O)c1cccc2c1oc(=O)n2CCCCN1CCN(c2ccc(F)cc2)CC1] | | |

-continued
| CMPD | STRUCTURE | Ki (nM) σ₁ | Ki (nM) σ₂ |
|---|---|---|---|
| CM500 | 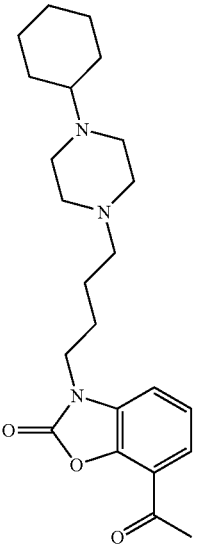 [SMILES: CC(=O)c1cccc2c1oc(=O)n2CCCCN1CCN(C2CCCCC2)CC1] | | |
| CM504 | 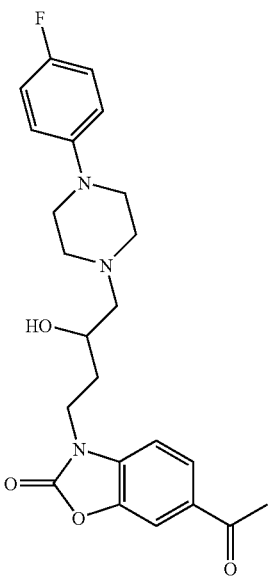 [SMILES: CC(=O)c1ccc2c(c1)oc(=O)n2CCC(O)CN1CCN(c2ccc(F)cc2)CC1] | | |
| CM528 | 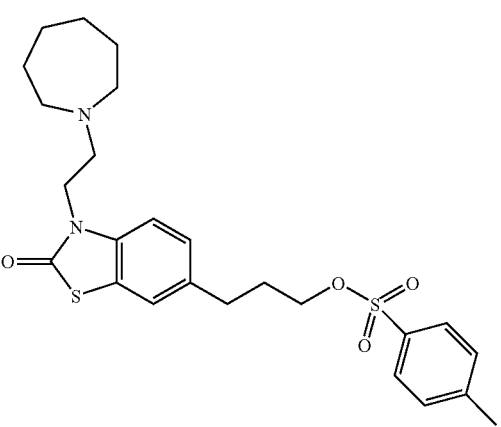 [SMILES: Cc1ccc(S(=O)(=O)OCCCc2ccc3c(c2)sc(=O)n3CCN2CCCCCC2)cc1] | | |

-continued
| CMPD | STRUCTURE | Ki (nM) σ₁ | Ki (nM) σ₂ |
|---|---|---|---|
| CM538 | 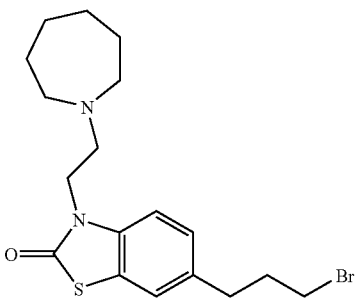 [SMILES: O=c1sc2cc(CCCBr)ccc2n1CCN1CCCCCC1] | | |
| CM539 | 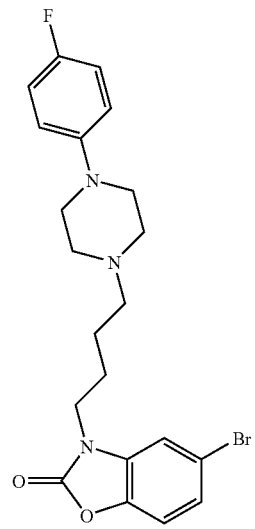 [SMILES: O=c1oc2ccc(Br)cc2n1CCCCN1CCN(c2ccc(F)cc2)CC1] | | |
| CM540 | 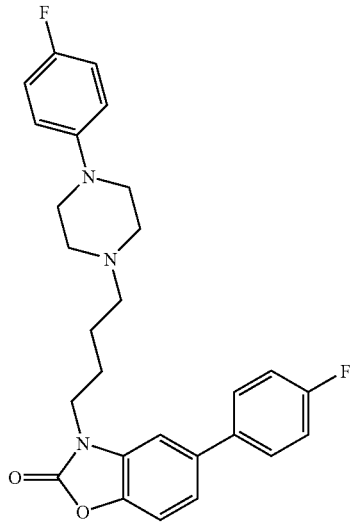 [SMILES: O=c1oc2ccc(-c3ccc(F)cc3)cc2n1CCCCN1CCN(c2ccc(F)cc2)CC1] | | |

-continued
| CMPD | STRUCTURE | Ki (nM) σ₁ | Ki (nM) σ₂ |
|---|---|---|---|
| CM563 | 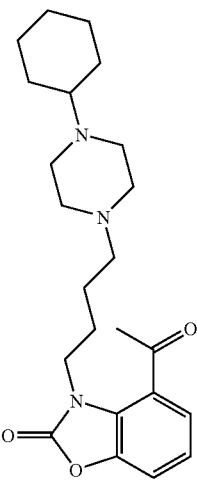 [SMILES: CC(=O)c1cccc2oc(=O)n(CCCCN3CCN(C4CCCCC4)CC3)c12] | | |
| CM564 | 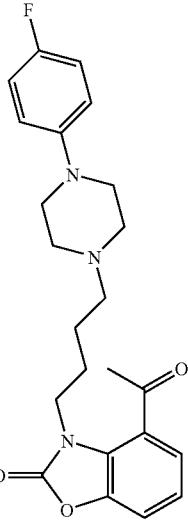 | | |
| CM566 | 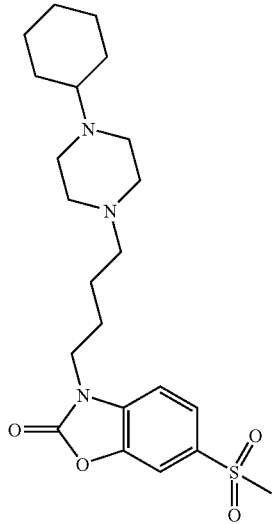 [SMILES: CS(=O)(=O)c1ccc2c(c1)oc(=O)n2CCCCN1CCN(C2CCCCC2)CC1] | | |

-continued
| CMPD | STRUCTURE | Ki (nM) $\sigma_1$ | Ki (nM) $\sigma_2$ |
| --- | --- | --- | --- |
| CM567 | 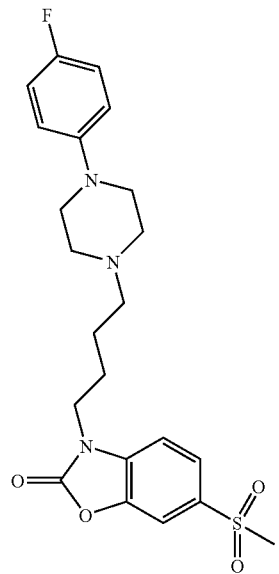 [SMILES: CS(=O)(=O)c1ccc2c(c1)oc(=O)n2CCCCN1CCN(c2ccc(F)cc2)CC1] | | |
| CM569 | 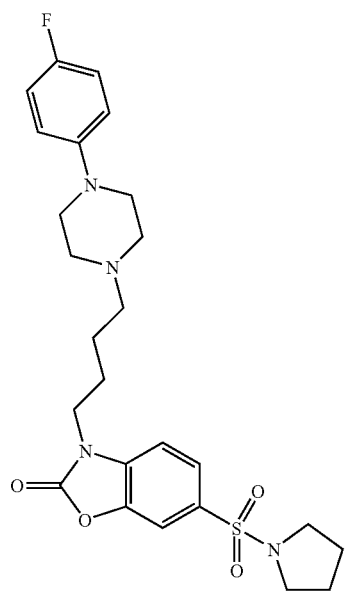 [SMILES: O=c1oc2cc(S(=O)(=O)N3CCCC3)ccc2n1CCCCN1CCN(c2ccc(F)cc2)CC1] | | |

-continued
| CMPD | STRUCTURE | Ki (nM) σ₁ | Ki (nM) σ₂ |
|---|---|---|---|
| CM571 | 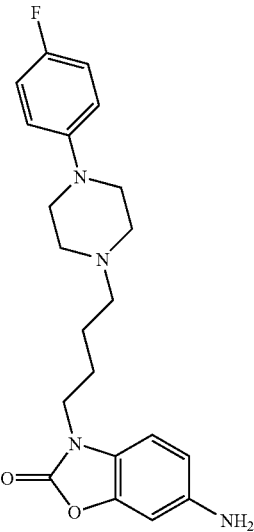 [SMILES: Nc1ccc2c(c1)oc(=O)n2CCCCN1CCN(c2ccc(F)cc2)CC1] | | |
| CM572 | 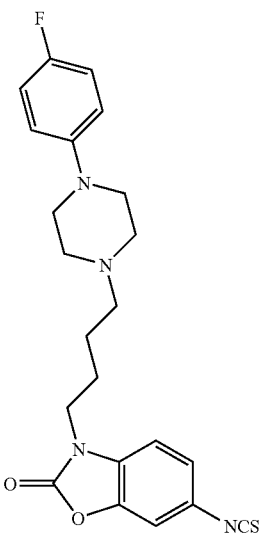 | | |
| CM585 | 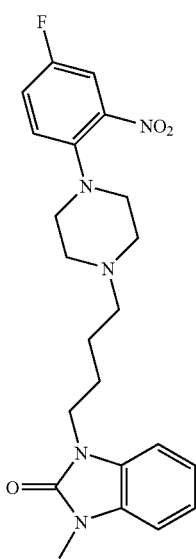 [SMILES: Cn1c(=O)n(CCCCN2CCN(c3ccc(F)cc3[N+](=O)[O-])CC2)c2ccccc21] | | |

-continued
| CMPD | STRUCTURE | Ki (nM) σ₁ | Ki (nM) σ₂ |
|------|-----------|------------|------------|
| CM592 | 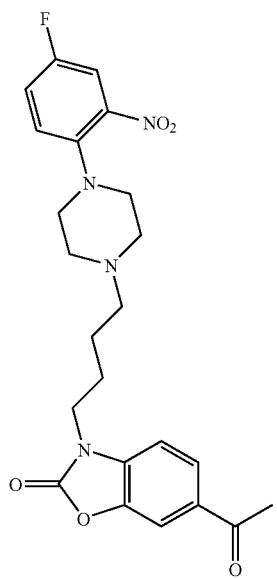 [SMILES: CC(=O)c1ccc2c(c1)oc(=O)n2CCCCN1CCN(c2ccc(F)cc2[N+](=O)[O-])CC1] | 369.1 ± 14.2 | 6.30 ± 0.39 |
| CM599 | 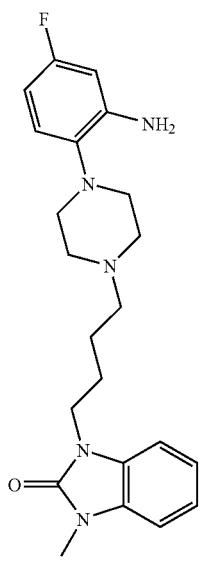 | 215.7 ± 11.8 | 3.59 ± 0.12 |

| CMPD | STRUCTURE | Ki (nM) $\sigma_1$ | Ki (nM) $\sigma_2$ |
| --- | --- | --- | --- |
| CM600 | 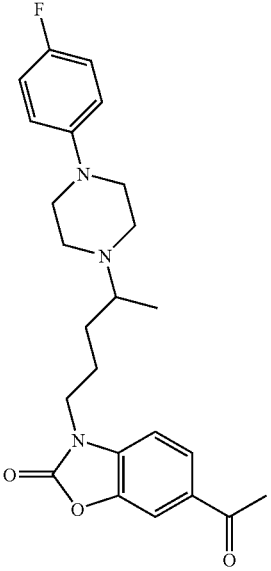 [SMILES: CC(=O)c1ccc2c(c1)oc(=O)n2CCCC(C)N1CCN(c2ccc(F)cc2)CC1] | 27.1 ± 2.32 | 2.15 ± 0.09 |
| CM608 | 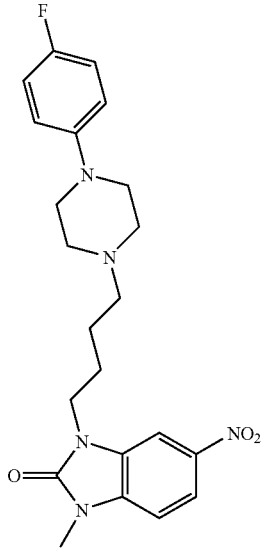 [SMILES: Cn1c(=O)n(CCCCN2CCN(c3ccc(F)cc3)CC2)c2cc([N+](=O)[O-])ccc21] | 15.5 ± 1.75 | 4.72 ± 0.42 |

-continued
| CMPD | STRUCTURE | Ki (nM) $\sigma_1$ | Ki (nM) $\sigma_2$ |
|---|---|---|---|
| CM609 | 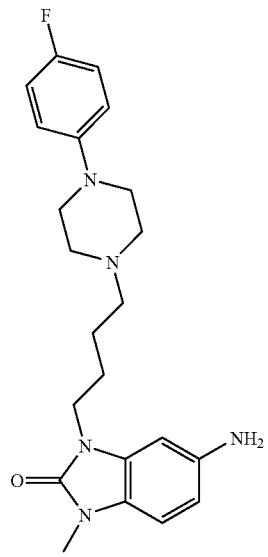 [SMILES: Cn1c(=O)n(CCCCN2CCN(c3ccc(F)cc3)CC2)c2cc(N)ccc21] | 23.4 ± 2.63 | 26.6 ± 2.74 |
| CM617 | 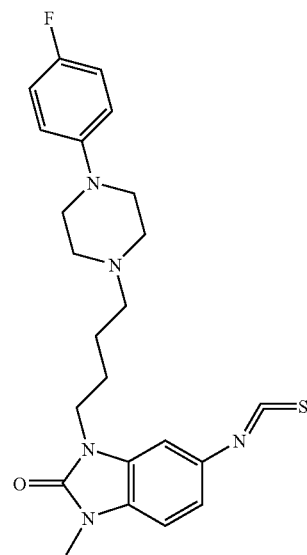 [SMILES: Cn1c(=O)n(CCCCN2CCN(c3ccc(F)cc3)CC2)c2cc(N=C=S)ccc21] | 97.4 ± 6.20 | 30.1 ± 3.42 |

-continued
| CMPD | STRUCTURE | Ki (nM) $\sigma_1$ | Ki (nM) $\sigma_2$ |
|---|---|---|---|
| CM621 | 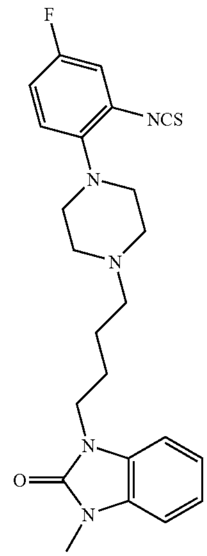 | 96.5 ± 5.80 | 12.60 ± 1.01 |
| CM623 | 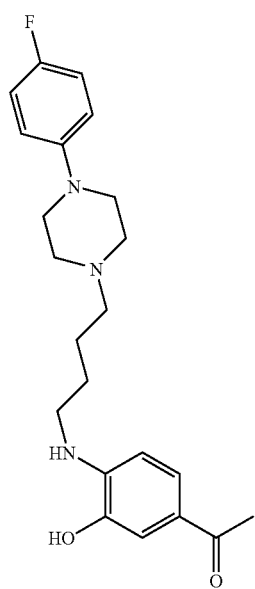 [SMILES: CC(=O)c1ccc(NCCCCN2CCN(c3ccc(F)cc3)CC2)c(O)c1] | 29.4 ± 3.93 | 44.1 ± 3.40 |

| CMPD | STRUCTURE | Ki (nM) σ₁ | Ki (nM) σ₂ |
|---|---|---|---|
| CM624 | 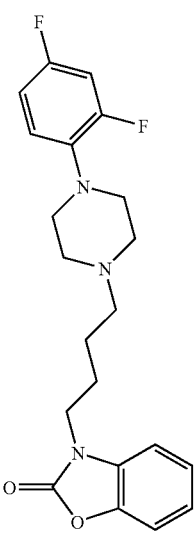 [SMILES: O=c1oc2ccccc2n1CCCCN1CCN(c2ccc(F)cc2F)CC1] | 14.8 ± 0.71 | 1.96 ± 0.11 |
| CM625 | 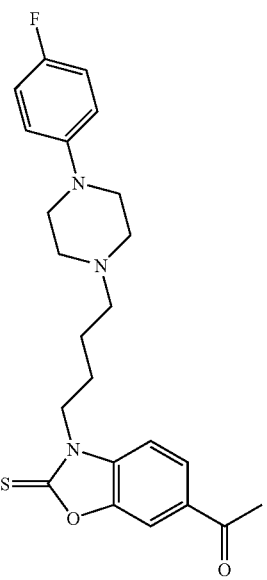 [SMILES: CC(=O)c1ccc2c(c1)oc(=S)n2CCCCN1CCN(c2ccc(F)cc2)CC1] | 10.8 ± 0.78 | 1.88 ± 0.13 |

-continued

| CMPD | STRUCTURE | Ki (nM) $\sigma_1$ | Ki (nM) $\sigma_2$ |
|---|---|---|---|
| CM627 | 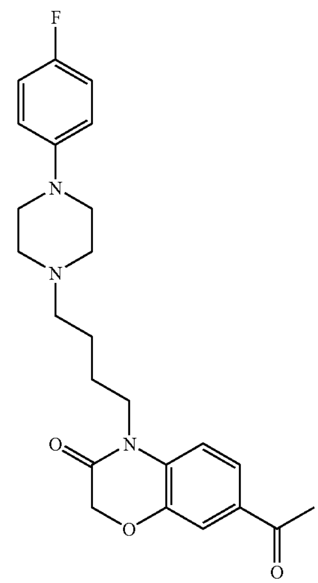 [SMILES: CC(=O)c1ccc2c(c1)OCC(=O)N2CCCCN1CCN(c2ccc(F)cc2)CC1] | 25.5 ± 1.11 | 6.34 ± 0.17 |
| CM657 | 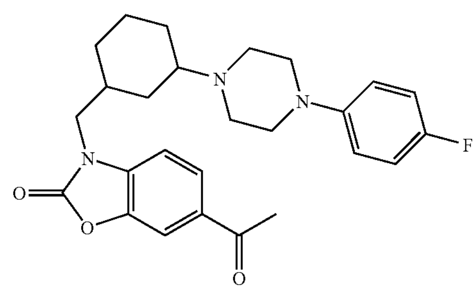 [SMILES: CC(=O)c1ccc2c(c1)oc(=O)n2CC1CCCC(N2CCN(c3ccc(F)cc3)CC2)C1] | 12.7 ± 1.06 | 5.99 ± 0.59 |
| CM666 | 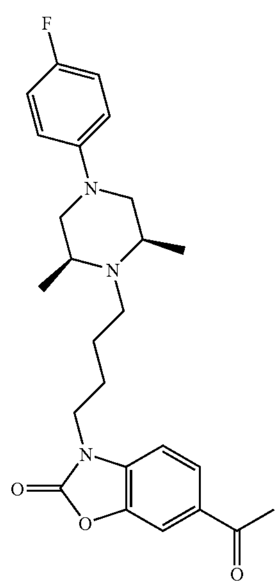 [SMILES: CC(=O)c1ccc2c(c1)oc(=O)n2CCCCN1[C@H](C)CN(c2ccc(F)cc2)C[C@@H]1C] | 21.2 ± 2.34 | 14.9 ± 0.52 |

-continued
| CMPD | STRUCTURE | Ki (nM) σ₁ | Ki (nM) σ₂ |
|---|---|---|---|
| CM673 | 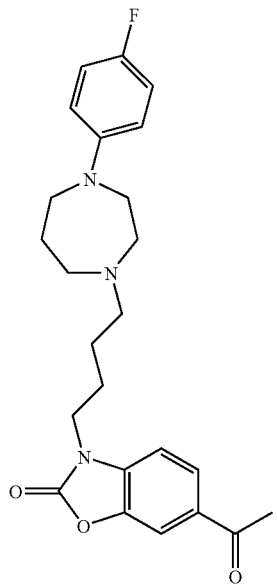 [SMILES: CC(=O)c1ccc2c(c1)oc(=O)n2CCCCN1CCCN(c2ccc(F)cc2)CC1] | 104.1 ± 8.06 | 50.6 ± 4.32 |
| CM697 | 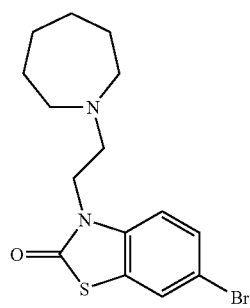 [SMILES: O=c1sc2cc(Br)ccc2n1CCN1CCCCCC1] | | |
| CM699 | 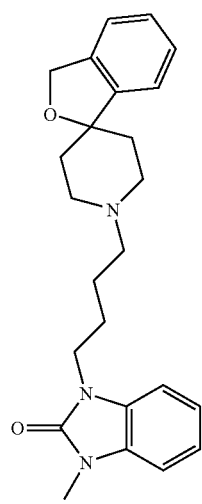 [SMILES: Cn1c(=O)n(CCCCN2CCC3(CC2)OCc2ccccc23)c2ccccc21] | | |

-continued

| CMPD | STRUCTURE | Ki (nM) $\sigma_1$ | Ki (nM) $\sigma_2$ |
|---|---|---|---|
| CM711 | 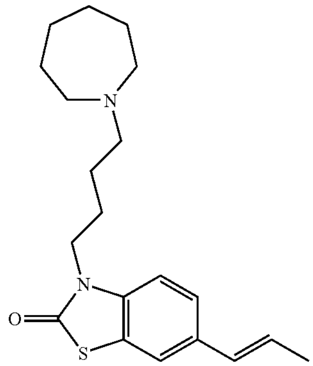 [SMILES: C/C=C/c1ccc2c(c1)sc(=O)n2CCCCN1CCCCCC1] | | |
| CM728 | 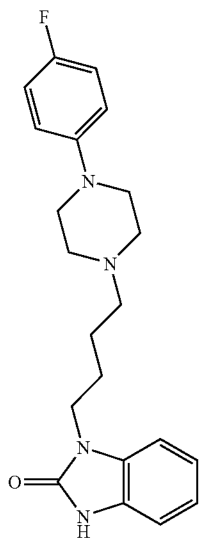 [SMILES: O=c1[nH]c2ccccc2n1CCCCN1CCN(c2ccc(F)cc2)CC1] | $186.2 \pm 11.8$ | $29.6 \pm 1.51$ |
| CM764 | 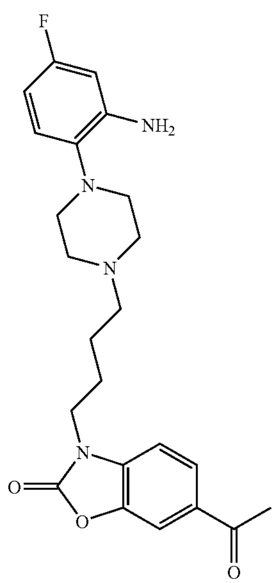 [SMILES: CC(=O)c1ccc2c(c1)oc(=O)n2CCCCN1CCN(c2ccc(F)cc2N)CC1] | | |

| CMPD | STRUCTURE | Ki (nM) σ₁ | Ki (nM) σ₂ |
|---|---|---|---|
| CM768 | 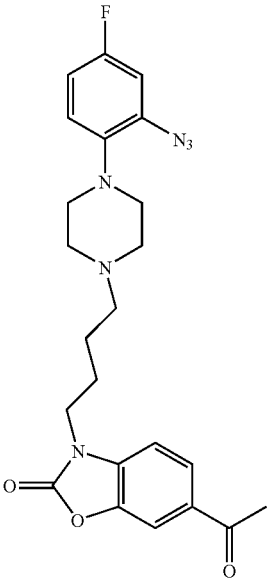 [SMILES: CC(=O)c1ccc2c(c1)oc(=O)n2CCCCN1CCN(c2ccc(F)cc2N=[N+]=[N-])CC1] | | |
| CM769 | 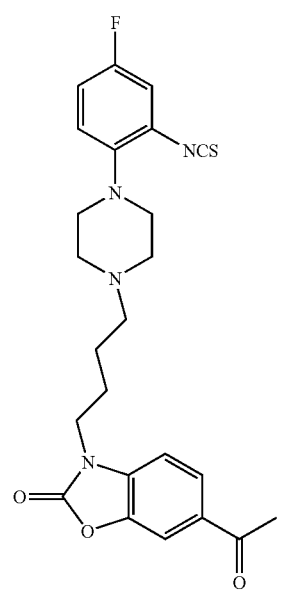 | | |

| CMPD | STRUCTURE | Ki (nM) σ$_1$ | Ki (nM) σ$_2$ |
|---|---|---|---|
| CM775 | 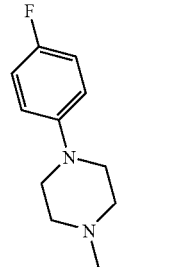 | | |
| CM777 | 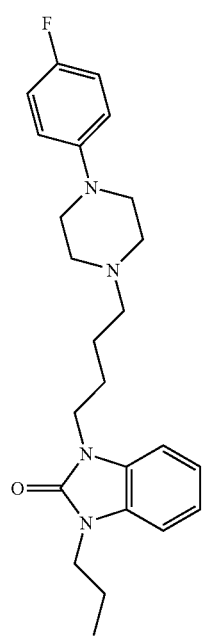 [SMILES: CCCn1c(=O)n(CCCCN2CCN(c3ccc(F)cc3)CC2)c2ccccc21] | | |

| CMPD | STRUCTURE | Ki (nM) $\sigma_1$ | Ki (nM) $\sigma_2$ |
|---|---|---|---|
| CM778 | 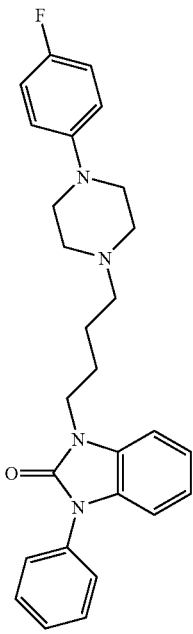 [SMILES: O=c1n(CCCCN2CCN(c3ccc(F)cc3)CC2)c2ccccc2n1-c1ccccc1] | | |
| CM781 | 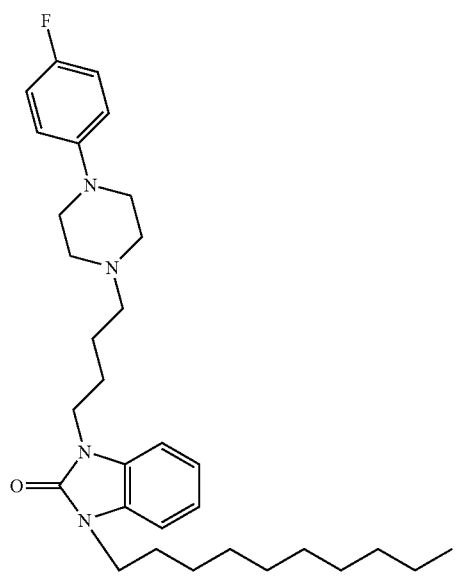 [SMILES: CCCCCCCCCCn1c(=O)n(CCCCN2CCN(c3ccc(F)cc3)CC2)c2ccccc21] | | |

| CMPD | STRUCTURE | Ki (nM) $\sigma_1$ | Ki (nM) $\sigma_2$ |
|---|---|---|---|
| CM782 | 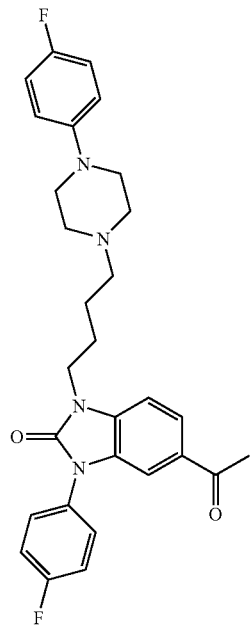 [SMILES: CC(=O)c1ccc2c(c1)n(-c1ccc(F)cc1)c(=O)n2CCCCN1CCN(c2ccc(F)cc2)CC1] | | |
| NF6 | 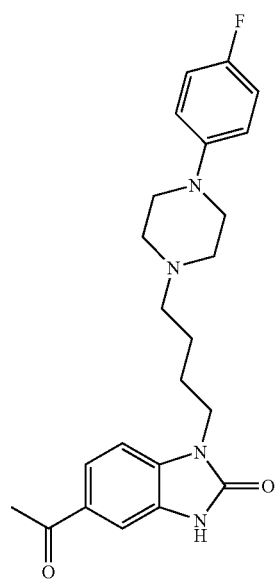 [SMILES: CC(=O)c1ccc2c(c1)[nH]c(=O)n2CCCCN1CCN(c2ccc(F)cc2)CC1] | | |

| CMPD | STRUCTURE | Ki (nM) σ$_1$ | Ki (nM) σ$_2$ |
|---|---|---|---|
| NF7 | 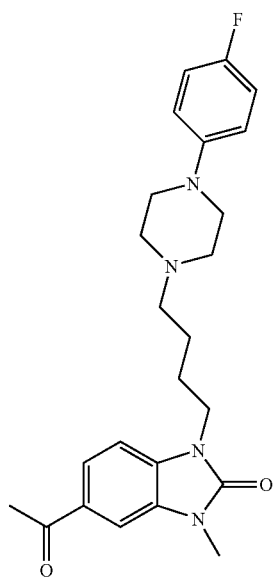 [SMILES: CC(=O)c1ccc2c(c1)n(C)c(=O)n2CCCCN1CCN(c2ccc(F)cc2)CC1] | | |
| NF8 | 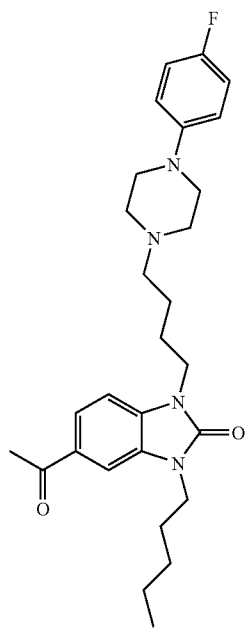 [SMILES: CCCCCn1c(=O)n(CCCCN2CCN(c3ccc(F)cc3)CC2)c2ccc(C(C)=O)cc21] | | |

| CMPD | STRUCTURE | Ki (nM) $\sigma_1$ | Ki (nM) $\sigma_2$ |
|---|---|---|---|
| NF9 | 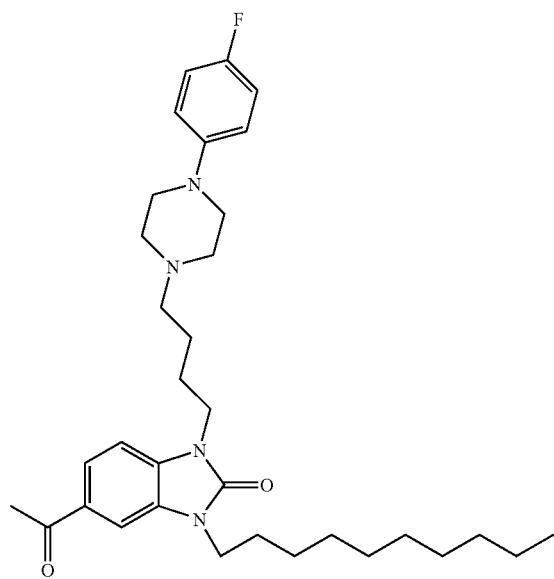 [SMILES: CCCCCCCCCCn1c(=O)n(CCCCN2CCN(c3ccc(F)cc3)CC2)c2ccc(C(C)=O)cc21] | | |
| NF10 | 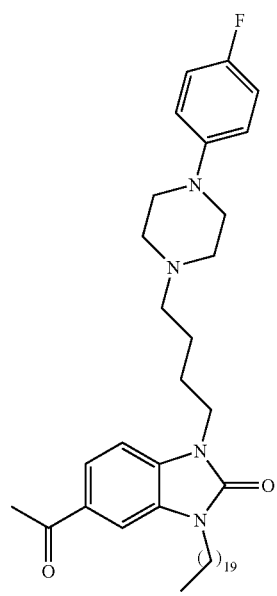 [SMILES: CCn1c(=O)n(CCCCN2CCN(c3ccc(F)cc3)CC2)c2ccc(C(C)=O)cc21] | | |

| CMPD | STRUCTURE | Ki (nM) σ₁ | Ki (nM) σ₂ |
|---|---|---|---|
| NF12 | 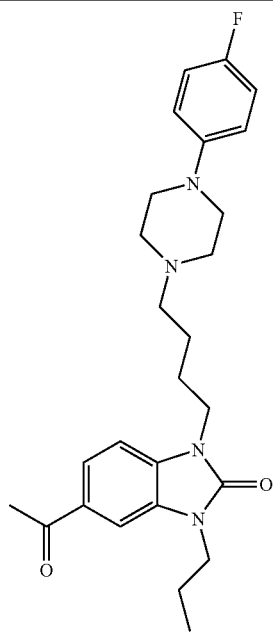 | | |
| EA2 | 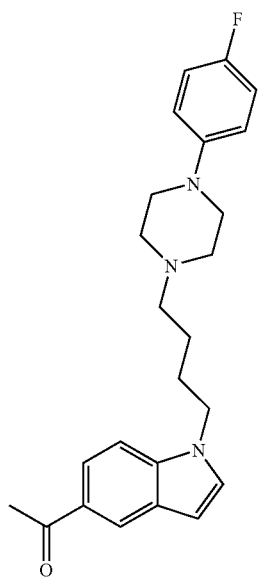 [SMILES: CC(=O)c1ccc2c(ccn2CCCCN2CCN(c3ccc(F)cc3)CC2)c1] | | |

| CMPD | STRUCTURE | Ki (nM) $\sigma_1$ | Ki (nM) $\sigma_2$ |
|---|---|---|---|
| EA6 | 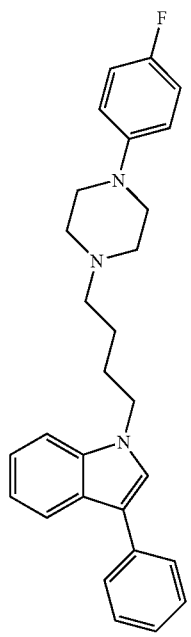 [SMILES: Fc1ccc(N2CCN(CCCCn3cc(-c4ccccc4)c4ccccc43)CC2)cc1] | | |
| EA7 | 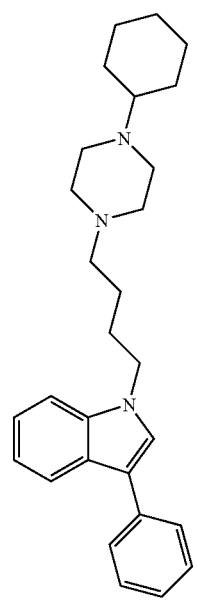 [SMILES: c1ccc(-c2cn(CCCCN3CCN(C4CCCCC4)CC3)c3ccccc23)cc1] | | |

-continued
| CMPD | STRUCTURE | Ki (nM) $\sigma_1$ | Ki (nM) $\sigma_2$ |
|---|---|---|---|
| EA8 | 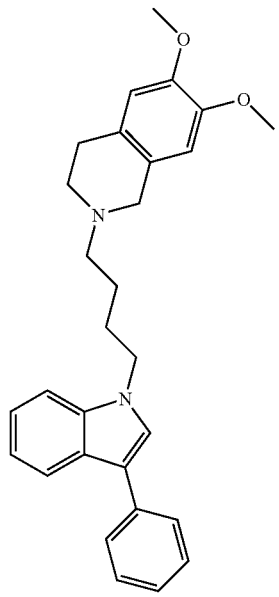 [SMILES: COc1cc2c(cc1OC)CN(CCCCn1cc(-c3ccccc3)c3ccccc31)CC2] | | |
| EA12 | 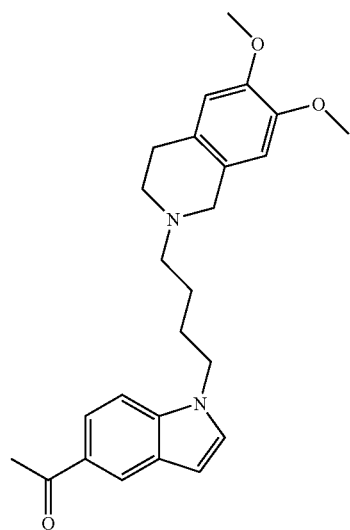 [SMILES: COc1cc2c(cc1OC)CN(CCCCn1ccc3cc(C(C)=O)ccc31)CC2] | | |

| CMPD | STRUCTURE | Ki (nM) σ₁ | Ki (nM) σ₂ |
|---|---|---|---|
| EA13 | 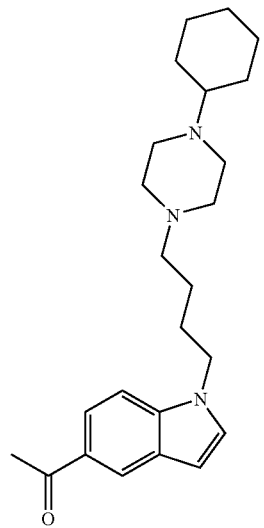 [SMILES: CC(=O)c1ccc2c(ccn2CCCCN2CCN(C3CCCCC3)CC2)c1] | | |
| EA14 | 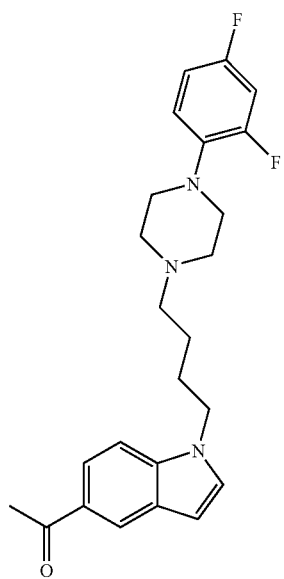 [SMILES: CC(=O)c1ccc2c(ccn2CCCCN2CCN(c3ccc(F)cc3F)CC2)c1] | | |

-continued
| CMPD | STRUCTURE | Ki (nM) σ$_1$ | Ki (nM) σ$_2$ |
|---|---|---|---|
| EA18 | 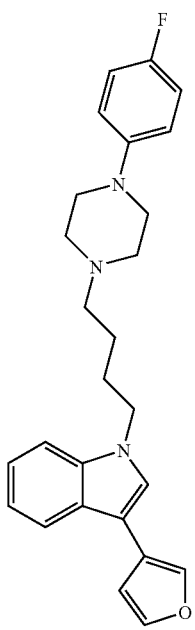 [SMILES: Fc1ccc(N2CCN(CCCCn3cc(-c4ccoc4)c4ccccc43)CC2)cc1] | | |
| EA21 | 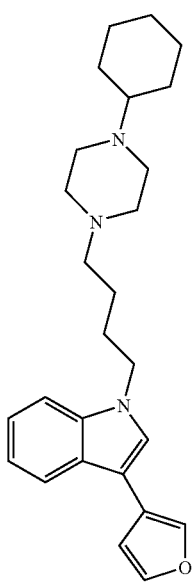 [SMILES: c1ccc2c(c1)c(-c1ccoc1)cn2CCCCN1CCN(C2CCCCC2)CC1] | | |
| SN-228 | 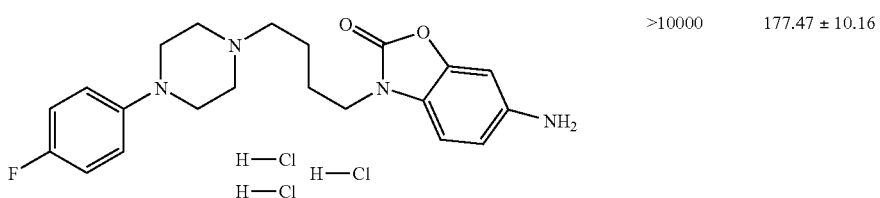 | >10000 | 177.47 ± 10.16 |

-continued

| CMPD | STRUCTURE | Ki (nM) $\sigma_1$ | Ki (nM) $\sigma_2$ |
|---|---|---|---|
| SN-248 | 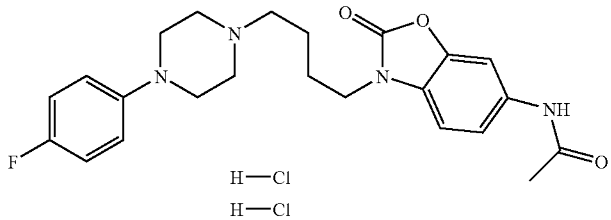 | 88.43 ± 12.72 | 48.13 ± 5.68 |
| SN-249 | 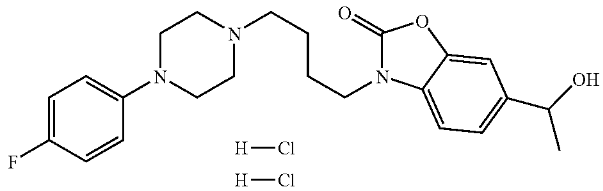 | 608.9 ± 39.75 | 8.68 ± 0.57 |
| SN-250 | 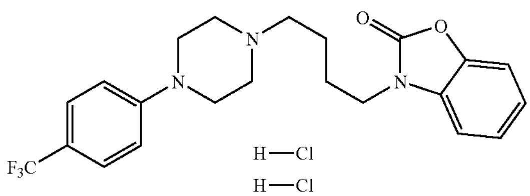 | 87.58 ± 8.77 | 98.81 ± 1.08 |
| SN-251 | 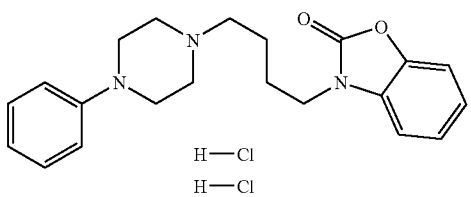 | 18.35 ± 1.46 | 11.44 ± 1.15 |
| SN-252 | 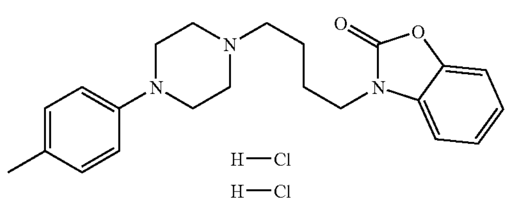 | 212.8 ± 22.24 | 107.02 ± 8.21 |
| SN-253 | 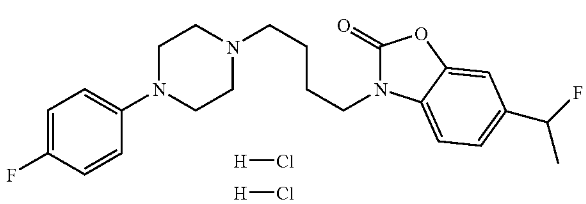 | 162.3 ± 11.45 | 6.12 ± 0.37 |

-continued
| CMPD | STRUCTURE | Ki (nM) $\sigma_1$ | Ki (nM) $\sigma_2$ |
|---|---|---|---|
| SC-5 | 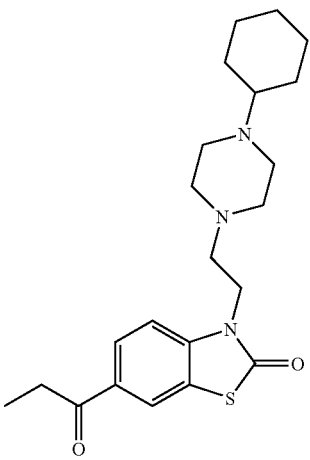 [SMILES: CCC(=O)c1ccc2c(c1)sc(=O)n2CCN1CCN(C2CCCCC2)CC1] | 6.75 ± 0.6 | 3.73 ± 0.43 |
| SC-6 | 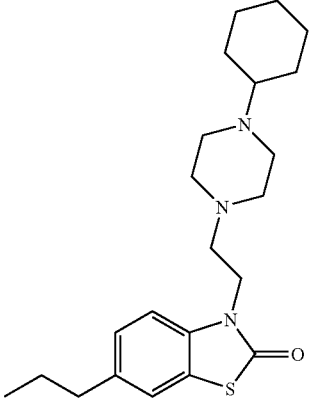 [SMILES: CCCc1ccc2c(c1)sc(=O)n2CCN1CCN(C2CCCCC2)CC1] | 2.15 ± 0.25 | 2.43 ± 0.09 |
| SC-10 | 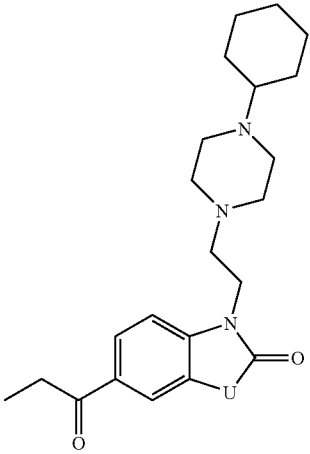 | 14.3 ± 0.34 | 4.85 ± 0.31 |

-continued

| CMPD | STRUCTURE | Ki (nM) $\sigma_1$ | Ki (nM) $\sigma_2$ |
|---|---|---|---|
| SC-12 | (cyclohexyl-piperazine-ethyl linked to N of 6-propyl-benzoxazol-2(3H)-one) | 7.50 ± 0.59 | 4.02 ± 0.23 |
| AZ-57 | (benzothiazol-2(3H)-one with N-butyl chain bearing methyl, piperazine-cyclohexyl) 2HCl<br>Chemical Formula: $C_{22}H_{35}Cl_2N_3OS$<br>Exact Mass: 459.19 | 8.73 ± 1.32 | 3.15 ± 0.19 |
| AZ-59 | (benzothiazole-2(3H)-thione with N-butyl chain bearing methyl, piperazine-cyclohexyl) 2HCl<br>Chemical Formula: $C_{22}H_{35}Cl_2N_3S_2$<br>Exact Mass: 475.16 | 8.94 ± 1.64 | 0.99 ± 0.178 |
| AZ-60 | (benzothiazin-3(4H)-one with N-butyl chain bearing methyl, piperazine-cyclohexyl) 2HCl<br>Chemical Formula: $C_{23}H_{37}Cl_2N_3OS$<br>Exact Mass: 473.20 | 92.36 ± 9.76 | 5.49 ± 1.10 |
| AZ-66 | (6-fluoro-benzothiazol-2(3H)-one with N-butyl chain bearing methyl, piperazine-cyclohexyl) 2HCl<br>Chemical Formula: $C_{22}H_{34}Cl_2FN_3OS$<br>Exact Mass: 477.18 | 0.31 ± 0.09 | 1.76 ± 0.34 |

-continued

| CMPD | STRUCTURE | Ki (nM) σ₁ | Ki (nM) σ₂ |
|---|---|---|---|
| AZ-68 | 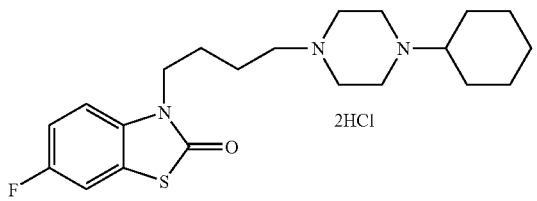<br>2HCl<br>Chemical Formula: $C_{21}H_{32}Cl_2FN_3OS$<br>Exact Mass: 463.16 | 2.01 ± 0.44 | 0.22 ± 0.09 |
| AZ-70 | 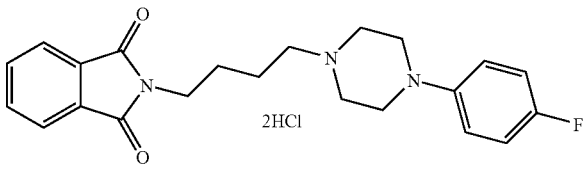<br>2HCl<br>Chemical Formula: $C_{22}H_{26}Cl_2FN_3O_2$<br>Exact Mass: 453.14 | | |
| AZ-71 | 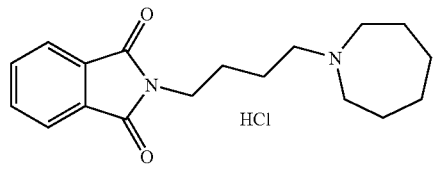<br>HCl<br>Chemical Formula: $C_{18}H_{25}ClN_2O_2$<br>Exact Mass: 336.16 | | |
| AZ-72 | 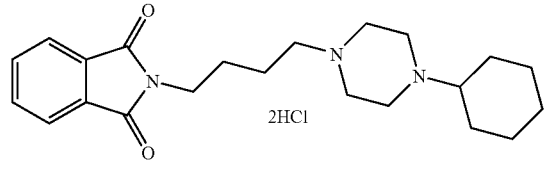<br>2HCl<br>Chemical Formula: $C_{22}H_{33}Cl_2N_3O_2$<br>Exact Mass: 441.19 | | |
| AZ-73 | 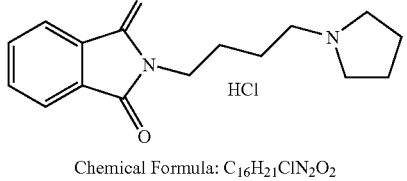<br>HCl<br>Chemical Formula: $C_{16}H_{21}ClN_2O_2$<br>Exact Mass: 308.13 | | |
| AZ-74 | 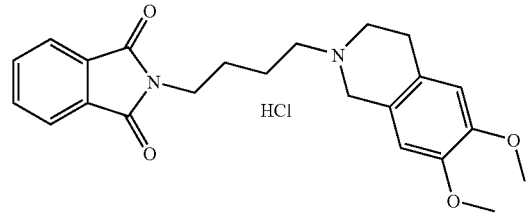<br>HCl<br>Chemical Formula: $C_{23}H_{27}ClN_2O_4$<br>Exact Mass: 430.17 | | |

-continued
| CMPD | STRUCTURE | Ki (nM) σ$_1$ | Ki (nM) σ$_2$ |
|---|---|---|---|
| AZ-77 | 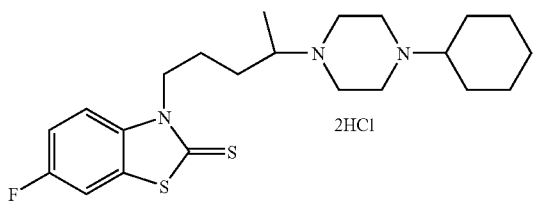<br>Chemical Formula: C$_{22}$H$_{34}$Cl$_2$FN$_3$S$_2$<br>Exact Mass: 493.16 | | |
| AZ-78 | 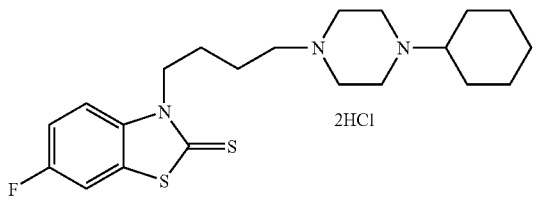<br>Chemical Formula: C$_{21}$H$_{32}$Cl$_2$FN$_3$S$_2$<br>Exact Mass: 479.14 | 7.21 ± 1.20 | 0.50 ± 0.30 |
| AZ-81 | 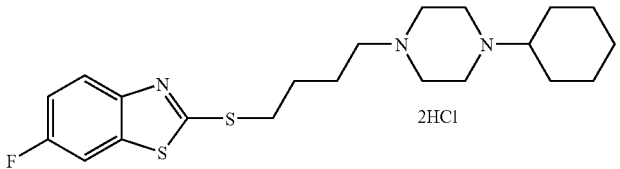<br>Chemical Formula: C$_{21}$H$_{32}$Cl$_2$FN$_3$S$_2$<br>Exact Mass: 479.14 | 14.3 ± 1.35 | 13.8 ± 1.34 |
| AZ-87 | 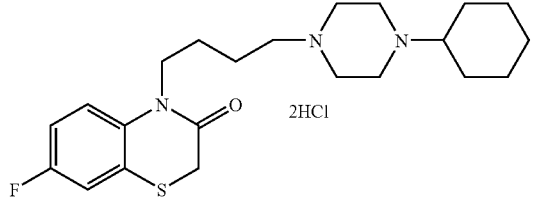<br>Chemical Formula: C$_{22}$H$_{34}$Cl$_2$FN$_3$OS<br>Exact Mass: 477.18 | 6.24 ± 1.97 | 6.45 ± 0.94 |
| AZ-93 | 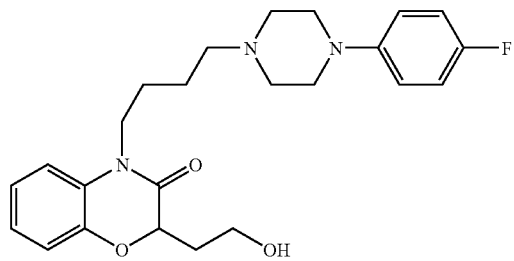<br>Chemical Formula: C$_{24}$H$_{30}$FN$_3$O$_3$<br>Exact Mass: 427.23 | | |

| CMPD | STRUCTURE | Ki (nM) σ₁ | Ki (nM) σ₂ |
|---|---|---|---|
| AZ-94 | 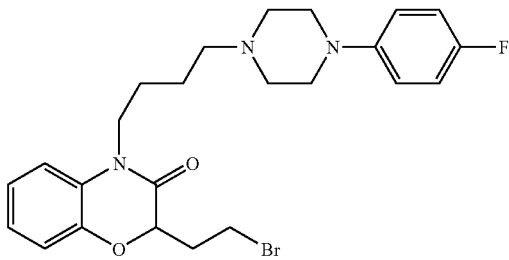<br>Chemical Formula: $C_{24}H_{29}BrFN_3O_2$<br>Exact Mass: 489.14 | | |
| AZ-95 | 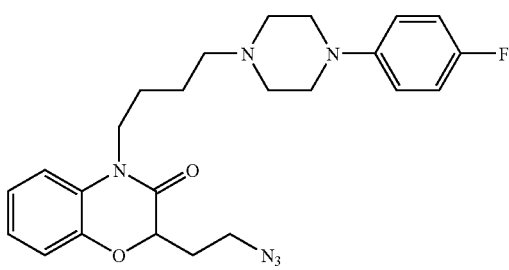<br>Chemical Formula: $C_{24}H_{29}FN_6O_2$<br>Exact Mass: 452.23 | | |
| AZ-96 | 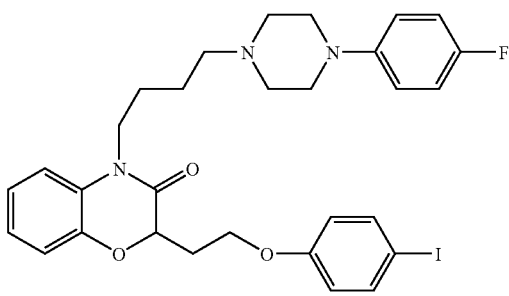<br>Chemical Formula: $C_{30}H_{33}FIN_3O_3$<br>Exact Mass: 629.16 | | |
| AZ-97 | 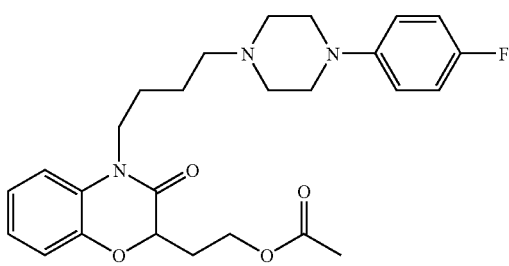<br>Chemical Formula: $C_{26}H_{32}FN_3O_4$<br>Exact Mass: 469.24 | | |

| CMPD | STRUCTURE | Ki (nM) σ₁ | Ki (nM) σ₂ |
|---|---|---|---|
| AZ-98 | 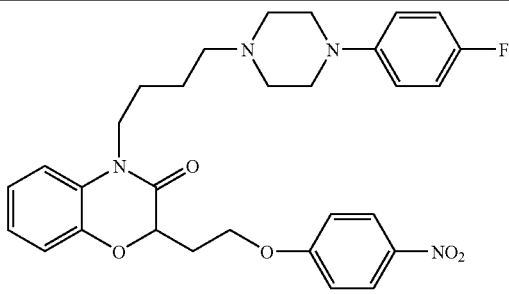<br>Chemical Formula: $C_{30}H_{33}FN_4O_5$<br>Exact Mass: 548.24 | | |
| AZ-99 | 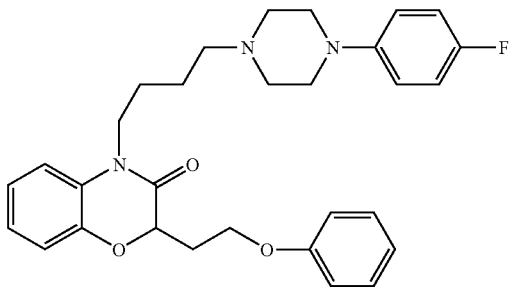<br>Chemical Formula: $C_{30}H_{34}FN_3O_3$<br>Exact Mass: 503.26 | | |
| AZ-100 | 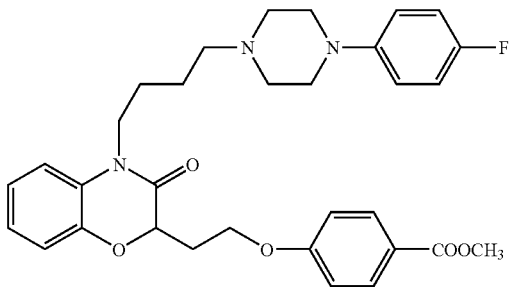<br>Chemical Formula: $C_{32}H_{36}FN_3O_5$<br>Exact Mass: 561.26 | | |
| AZ-101 | 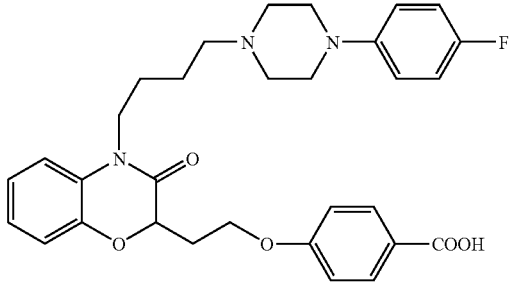<br>Chemical Formula: $C_{31}H_{34}FN_3O_5$<br>Exact Mass: 547.25 | | |

| CMPD | STRUCTURE | Ki (nM) σ₁ | Ki (nM) σ₂ |
|---|---|---|---|
| AZ-102 | 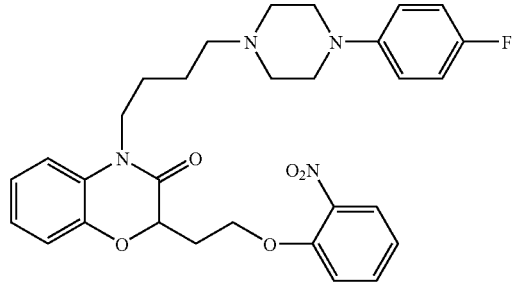<br>Chemical Formula: $C_{30}H_{33}FN_4O_5$<br>Exact Mass: 548.24 | | |
| AZ-103 | 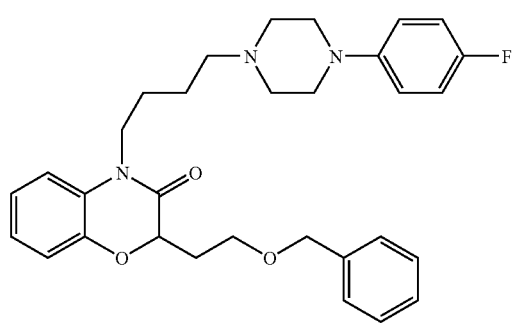<br>Chemical Formula: $C_{31}H_{36}FN_3O_3$<br>Exact Mass: 517.27 | | |
| AZ-104 | 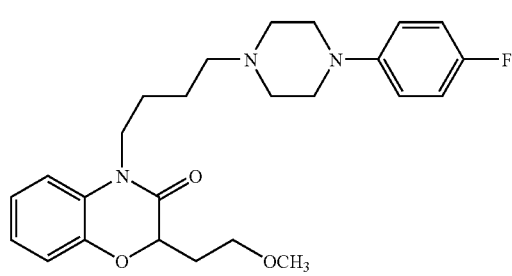<br>Chemical Formula: $C_{25}H_{32}FN_3O_3$<br>Exact Mass: 441.24 | | |
| AZ-105 | 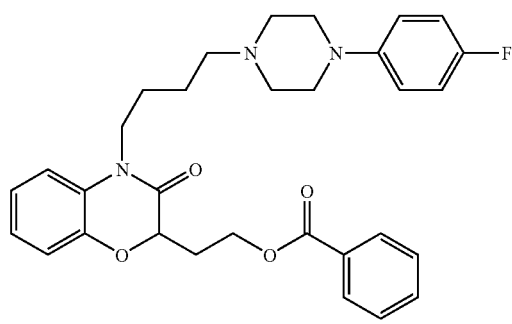<br>Chemical Formula: $C_{31}H_{34}FN_3O_4$<br>Exact Mass: 531.25 | | |

| CMPD | STRUCTURE | Ki (nM) σ₁ | Ki (nM) σ₂ |
|---|---|---|---|
| AZ-106 | 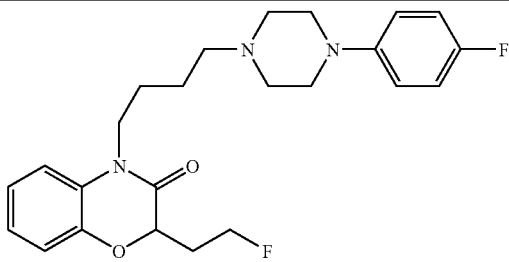<br>Chemical Formula: $C_{24}H_{29}F_2N_3O_2$<br>Exact Mass: 429.22 | | |
| AZ-107 | 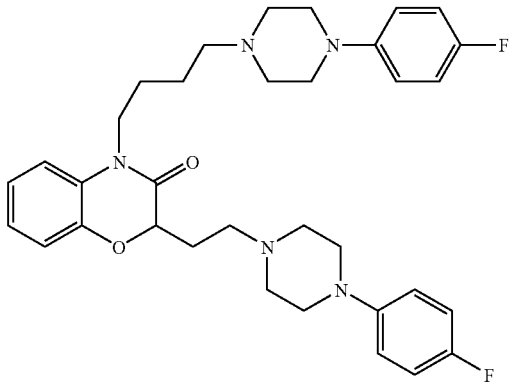<br>Chemical Formula: $C_{34}H_{41}F_2N_5O_2$<br>Exact Mass: 589.32 | | |
| AZ-108 | 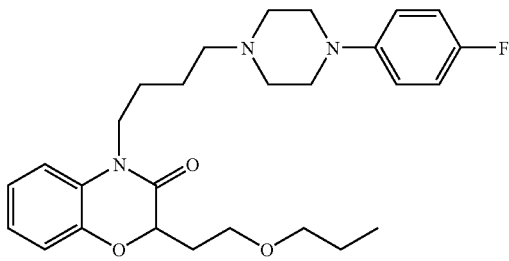<br>Chemical Formula: $C_{27}H_{36}FN_3O_3$<br>Exact Mass: 469.27 | | |
| AZ-109 | 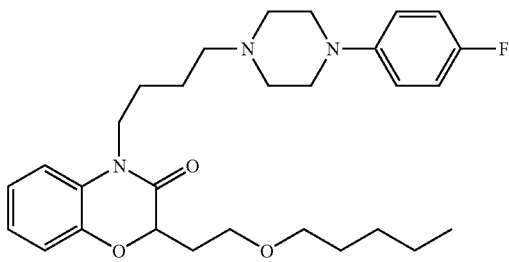<br>Chemical Formula: $C_{29}H_{40}FN_3O_3$<br>Exact Mass: 497.31 | | |

-continued
| CMPD | STRUCTURE | Ki (nM) σ₁ | Ki (nM) σ₂ |
|---|---|---|---|
| AZ-110 | 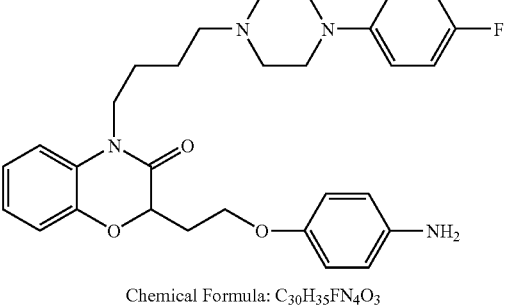<br>Chemical Formula: $C_{30}H_{35}FN_4O_3$<br>Exact Mass: 518.27 | | |
| AZ-112 | 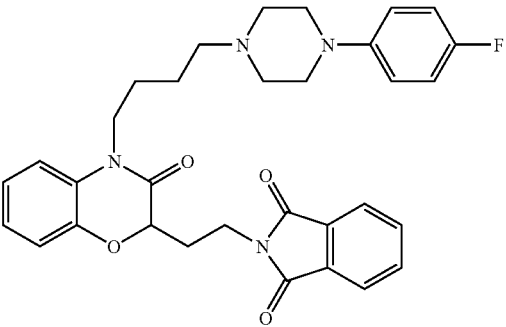<br>Chemical Formula: $C_{32}H_{33}FN_4O_4$<br>Exact Mass: 556.25 | | |
| AZ-113 | 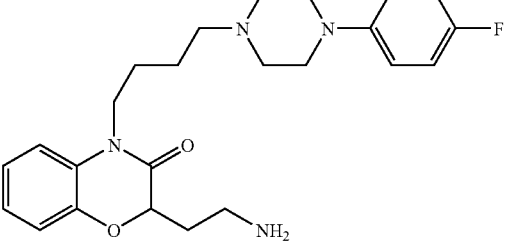<br>Chemical Formula: $C_{24}H_{31}FN_4O_2$<br>Exact Mass: 426.24 | | |
| AZ-114 | 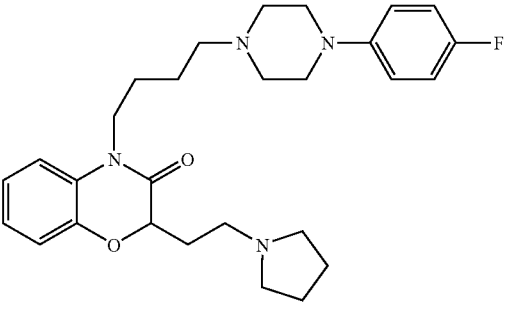<br>Chemical Formula: $C_{28}H_{37}FN_4O_2$<br>Exact Mass: 480.29 | | |

| CMPD | STRUCTURE | Ki (nM) σ₁ | Ki (nM) σ₂ |
|---|---|---|---|
| AZ-115 | 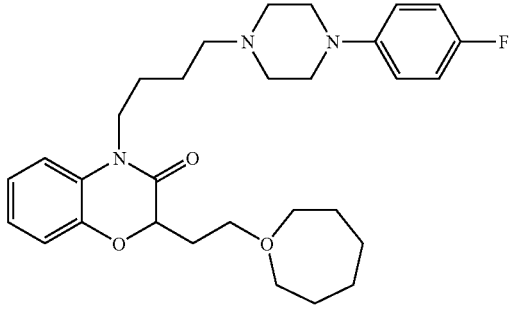<br>Chemical Formula: $C_{30}H_{41}FN_4O_2$<br>Exact Mass: 508.32 | | |
| AZ-116 | 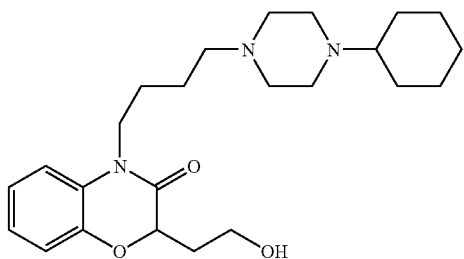<br>Chemical Formula: $C_{24}H_{37}N_3O_3$<br>Exact Mass: 415.28 | | |
| AZ-117 | 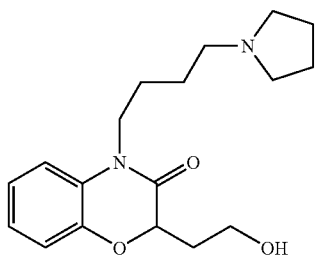<br>Chemical Formula: $C_{18}H_{26}N_2O_3$<br>Exact Mass: 318.19 | | |
| AZ-118 | 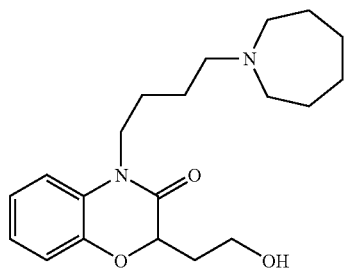<br>Chemical Formula: $C_{20}H_{30}N_2O_3$<br>Exact Mass: 346.23 | | |

-continued
| CMPD | STRUCTURE | Ki (nM) σ₁ | Ki (nM) σ₂ |
|---|---|---|---|
| AZ-119 | 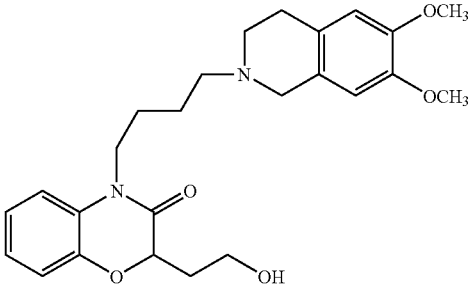 Chemical Formula: $C_{25}H_{32}N_2O_5$<br>Exact Mass: 440.23 | | |
| AZ-120 | 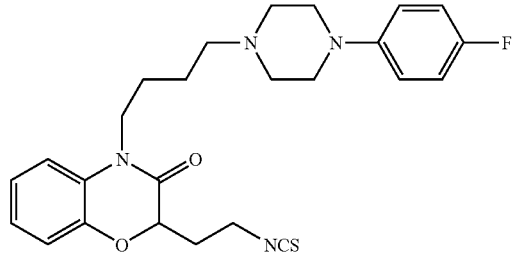 Chemical Formula: $C_{25}H_{29}FN_4O_2S$<br>Exact Mass: 468.20 | | |
| AZ-121 | 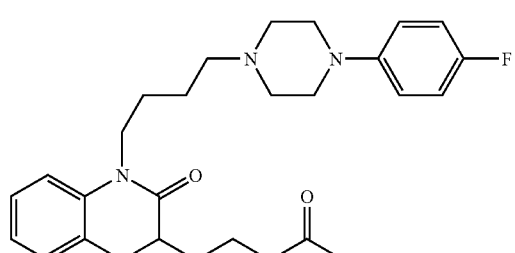 Chemical Formula: $C_{26}H_{33}FN_4O_3$<br>Exact Mass: 468.25 | | |
| AZ-122 | 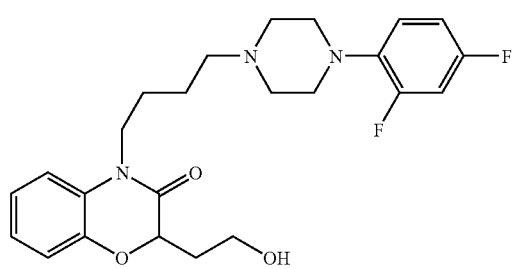 Chemical Formula: $C_{24}H_{29}F_2N_3O_3$<br>Exact Mass: 445.22 | | |

AZ-9

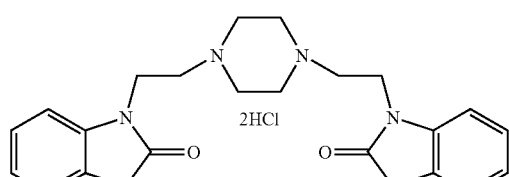

Chemical Formula: $C_{22}H_{26}Cl_2N_4O_4$
Exact Mass: 480.13

AZ-8

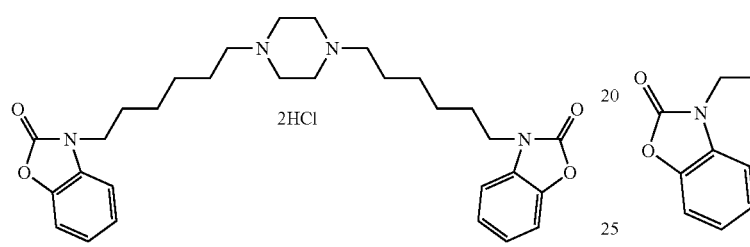

Chemical Formula: $C_{30}H_{42}Cl_2N_4O_4$
Exact Mass: 592.26

AZ-10

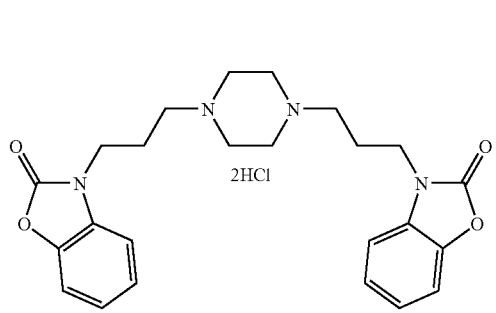

Chemical Formula: $C_{24}H_{30}Cl_2N_4O_4$
Exact Mass: 508.16

AZ-16

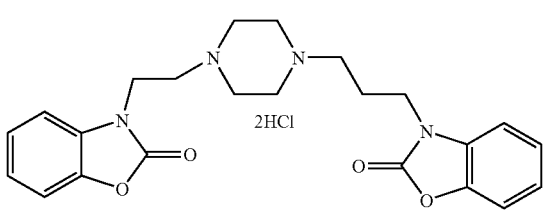

Chemical Formula: $C_{23}H_{28}Cl_2N_4O_4$
Exact Mass: 494.15

AZ-2

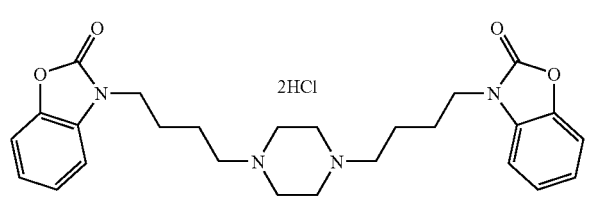

Chemical Formula: $C_{26}H_{34}Cl_2N_4O_4$
Exact Mass: 536.20

AZ-17

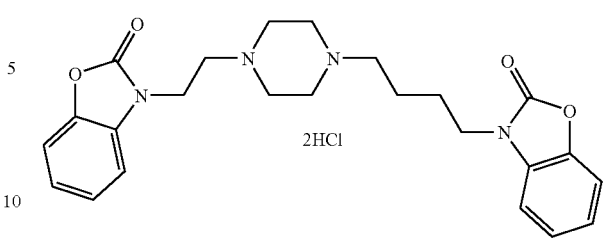

Chemical Formula: $C_{24}H_{30}Cl_2N_4O_4$
Exact Mass: 508.16

AZ-7

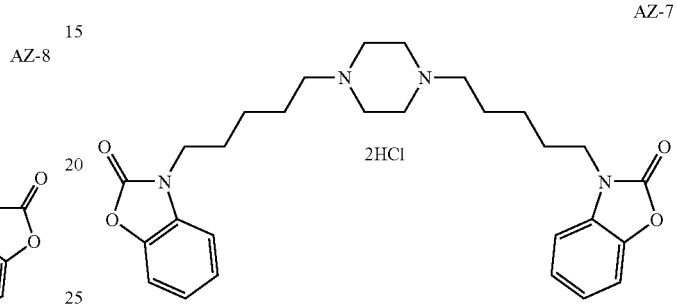

Chemical Formula: $C_{28}H_{38}Cl_2N_4O_4$
Exact Mass: 564.23

AZ-18

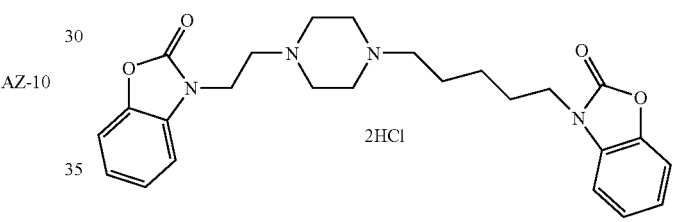

Chemical Formula: $C_{25}H_{32}Cl_2N_4O_4$
Exact Mass: 522.18

The present invention comprises a method of treating a subject for alleviation of affects in the subject resulting from drug intake or drug abuse by the subject comprising administering to the subject a therapeutically effective amount of at least one compound according to the invention.

The drug abuse or drug intake can result from methamphetamine intake or methamphetamine abuse by the subject or from cocaine abuse or cocaine intake by the subject.

The present invention further comprises a method of treating a subject having a need for therapy involving sigma receptors comprising administering to the subject an effective amount of at least one compound of the present invention and additionally comprises treating a subject to prevent neurotoxic effects resulting from drug abuse or drug intake by the subject comprising administering to the subject a therapeutically effective amount of at least one compound according to the invention.

The invention further comprises radioligand compositions comprising at least one compound according to the invention wherein at least one compound contains a radioactive element.

Pharmaceutical compositions according to the invention are those which are suitable for enteral, such as oral, administration and for parenteral, such as subcutaneous, administration to warm-blooded animals, especially humans, and which contain the pharmacologically active substance on its own or together with a pharmaceutically acceptable carrier.

The dosage of the active substance depends on the species of warm-blooded animal and on the age and individual condition, the illness to be treated and also on the mode of administration. Such dosage can be readily determined by those practicing in the relevant art area.

The novel pharmaceutical preparations contain from approximately 10% to approximately 95%, and preferably from approximately 20% to approximately 90%, of the active substance. Pharmaceutical compositions according to the invention can, for example, be in unit dose form, such as dragees, tablets, capsules, suppositories or ampoules.

The pharmaceutical compositions of the present invention are manufactured in a manner known per se, for example, by means of conventional mixing, granulating, confectioning, dissolving or lyophilizing processes. Pharmaceutical compositions for oral use can be obtained by combining the active substance with one or more solid carriers, if desired, granulating a resulting mixture and processing the mixture or granulate, if desired or necessary after the addition of suitable adjuncts, to form tablets or dragee cores. In so doing, they can also be incorporated into plastics carriers which release the active substances or allow them to diffuse in controlled amounts.

Suitable carriers are especially fillers such as sugars, for example, lactose, saccharose, mannitol or sorbitol, cellulose preparations and/or calcium phosphates, for example, tricalcium phosphate or calcium hydrogen phosphate, also binders such as starches, for example, corn, wheat, rice or potato starch, gelatine, tragacanth, methylcellulose, hydroxypropylmethylcellulose, sodium carboxymethylcellulose and/or polyvinylpyrrolidone, and/or, if desired, disintegrators such as the above-mentioned starches, also carboxymethyl starch, cross-linked polyvinylpyrrolidone, agar, alginic acid or a salt thereof such as sodium alginate. Adjuncts are especially flow-regulating and lubricating agents, for example, silica, talc, stearic acid or salts thereof such as magnesium or calcium stearate, and/or polyethylene glycol. Dragee cores are provided with suitable coatings that are, if desired, resistant to gastric juice, there being used, inter alia, concentrated sugar solutions which optionally contain gum arabic, talc, polyvinylpyrrolidone, polyethylene glycol and/or titanium dioxide, lacquer solutions in suitable organic solvents or solvent mixtures or, for the manufacture of coatings that are resistant to gastric juice, solutions of suitable cellulose preparations such as acetylcellulose phthalate or hydroxypropylmethylcellulose phthalate. Coloring substances or pigments can be added to the tablets or dragee coatings, for example for the purpose of identification or for indicating different doses of active substance.

Other orally administrable pharmaceutical compositions are dry-filled capsules made of gelatin and also soft, sealed capsules made of gelatin and a plasticizer such as glycerol or sorbitol. The dry-filled capsules may contain the active ingredient in the form of a granulate, for example, in admixture with fillers such as corn starch, binders and/or glidants such as talc or magnesium stearate and optionally stabilizers. In soft capsules, the active ingredient is preferably dissolved or suspended in suitable liquids or wax-like substances such as fatty oils, paraffin oil or polyethylene glycols, it being possible also for stabilizers to be added.

Other forms of oral administration are, for example, syrups prepared in a customary manner that contain the active ingredient in, for example, suspended form in a concentration that provides a suitable single dose when administered.

Further suitable dosage forms for parenteral administration are sterile aqueous solutions of an active ingredient in water-soluble form, for example, a water-soluble salt, or sterile aqueous injection suspensions which contain substances increasing the viscosity, for example, sodium, carboxymethyl cellulose, sorbitol and/or dextran, and optionally stabilizers. In addition, the active ingredient, with or without adjuvants, can also be in lyophilized form and brought into solution prior to parenteral administration by the addition of suitable solvents.

The invention also relates to a method of treatment of pathological conditions in a mammal, especially human, which as has been described hereinabove, which method comprises administering, a therapeutically effective amount of a compound of the formula I or of a pharmaceutically acceptable salt thereof.

The examples provided in the present application serve to illustrate the invention, but should not be construed as a limitation thereof.

REFERENCES CITED

1. Matsumoto, R. R. et. al. *Eur. J. Pharmacol.* 2001, 411, 261-273.
2. Maurice, T. et. al. *Prog. Neuropsychopharmacol. Biol. Psychiatry* 1997, 21, 69-102.
3. Sigma receptors: chemistry, cell biology and clinical implications. Edited by Rae R. Matsumoto, Wayne D. Bowen and Tsung Ping Su, New York, Springer 2007.
4. Harmer, M. et. al. *Proc. Natl. Acad Sci. USA.* 1996, 93, 8072-8077.
5. Kekuda, R. Y., et. al. *Biochem. Biophys. Res. Commun.* 1996, 229, 553-558.
6. Seth, P. et. al. *Biochem. Biophys. Res. Commun.* 1997, 41, 535-540.
7. Seth, P. et. al. *J. Neurochem,* 1998, 70, 922-931.
8. Mei, J and Pasternak G W, *Biochem Pharmacol.* 2001, 62, 349-355
9. Perrine, D M (1996) The Chemistry of Mind-Altering Drugs, American Chemical Society. Washington, D.C.
10. Wohler, V. (1862) Fortsetzung der Untersuchungen uber die Coca und das Cocain. Justus Liebigs Annalen der Chemie 121: 372.
11. National Survey on Drug Use and Health—http://www.samhsa.gov
12, Carroll F I., Howell L L, Kuhar M J (1999) Pharmacotherapies for treatment of cocaine abuse: preclinical aspects. J. Med. Chem. 42: 2721-2736.
13, Sharkey J, Glen K A, Wolfe S, Kuhar M J. Cocaine binding at sigma receptors. Eur. J. Pharmacol. 1988, 149: 171-174.
14. Mittlenian R, Wetli C V. Death caused by recreational cocaine use: an update. J. Am. Med. Assoc. 1984, 252: 1889-1893.

The invention claimed is:

1. A compound having the formula XIV

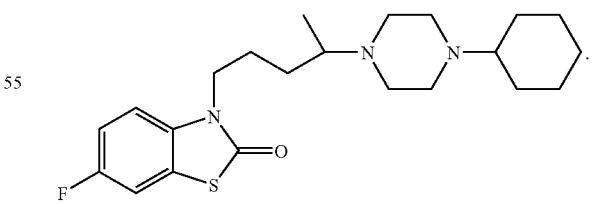

2. A pharmaceutical composition comprising the compound according to claim 1 and an acceptable carrier or excipient.

* * * * *